US010017535B2

(12) United States Patent
Kudova et al.

(10) Patent No.: US 10,017,535 B2
(45) Date of Patent: Jul. 10, 2018

(54) AMPHIPHILIC COMPOUNDS WITH NEUROPROTECTIVE PROPERTIES

(71) Applicants: USTAV ORGANICKE CHEMIE A BIOCHEMIE AV CR, v.v.i., Praha (CZ); FYZIOLOGICKY USTAV AV ČR, v.v.i., Praha (CZ)

(72) Inventors: Eva Kudova, Praha (CZ); Hana Chodounska, Praha (CZ); Vojtech Kapras, Praha (CZ); Ladislav Vyklicky, Kamenice (CZ); Karel Vales, Praha (CZ); Ullrich Jahn, Praha (CZ)

(73) Assignees: USTAV ORGANICKE CHEMIE A BIOCHEMIE AV CR, V.V.I., Praha (CZ); FYZIOLOGICKY USTAV AV CR, V.V.I., Praha (CZ)

( * ) Notice: Subject to any disclaimer, the term of this patent is extended or adjusted under 35 U.S.C. 154(b) by 0 days.

(21) Appl. No.: 15/506,318

(22) PCT Filed: Aug. 25, 2015

(86) PCT No.: PCT/CZ2015/000096
§ 371 (c)(1),
(2) Date: Feb. 24, 2017

(87) PCT Pub. No.: WO2016/029888
PCT Pub. Date: Mar. 3, 2016

(65) Prior Publication Data
US 2017/0240588 A1 Aug. 24, 2017

(30) Foreign Application Priority Data
Aug. 26, 2014 (CZ) .............................. PV 2014-575

(51) Int. Cl.
| | | |
|---|---|---|
| *C07D 213/18* | (2006.01) | |
| *C07J 43/00* | (2006.01) | |
| *C07J 53/00* | (2006.01) | |
| *C07J 9/00* | (2006.01) | |
| *C07J 41/00* | (2006.01) | |
| *C07C 305/20* | (2006.01) | |
| *C07C 59/80* | (2006.01) | |

(52) U.S. Cl.
CPC ............. *C07J 43/003* (2013.01); *C07C 59/80* (2013.01); *C07C 305/20* (2013.01); *C07D 213/18* (2013.01); *C07J 9/005* (2013.01); *C07J 41/0033* (2013.01); *C07J 53/001* (2013.01); *C07C 2603/26* (2017.05)

(58) Field of Classification Search
None
See application file for complete search history.

(56) References Cited

U.S. PATENT DOCUMENTS

| | | |
|---|---|---|
| 5,888,996 A | 3/1999 | Farb |
| 2004/0204490 A1 | 10/2004 | Farb |

FOREIGN PATENT DOCUMENTS

| | | |
|---|---|---|
| WO | 97/03677 A1 | 2/1997 |
| WO | 2010/136000 A2 | 12/2010 |
| WO | 2012/019106 A2 | 2/2012 |
| WO | 2012/110010 A1 | 8/2012 |

OTHER PUBLICATIONS

Costa B. M. et al: N-Methyl-D-aspartate (NMDA) Receptor NR2 Subunit Selectivity of a Series of Novel Piperazine-2,3-dicarboxylate Derivatives: Preferential Blockade of Extrasynaptic NMDA Receptors in the Rat Hippocampal CA3-CA1 Synapse, Journal of Pharmacology and Experimental Therapeutics, vol. 331, No. 2, Nov. 2009, pp. 618-626.
Irvine Mark W. et al: Piperazine-2,3-dicarboxylic Acid Derivatives as Dual Antagonists of NMDA and GluKI-Containing Kainate Receptors, Journal of Medicinal Chemistry, vol. 55, No. 1, Jan. 2012, pp. 327-341, US.
Borovska Jirina et al: Access of inhibitory neurosteroids to the NMDA receptor, British Journal of Pharmacology, vol. 166, No. 3, May 2012, pp. 1069-1083, Basingstoke, Hants; GB.
Kyung Ah Koo et al: A New Neuroprotective Pinusolide Derivative from the Leaves of Biota orientalis, Chemical and Pharmaceutical Bulletin, vol. 50, No. 6, Jan. 2002, pp. 834-836, JP.
Atkinson R M et al: Action of some steroids on the centtral nervous system of the mouse. II. Pharmacology, Journal of Medicinal Chemistry, American Chemical Society, vol. 8, No. 4, Jul. 1965, pp. 426-432, US.
Bolger M B et al: In Vitro and in Vivo Activity of 16,17-dehydro-epipregnanolones: 17,20-bond Torsional Energy Analysis and D-ring Conformation, Pharmaceutical Research, Springer New York LLC, vol. 13, No. 10, Jan. 1996, pp. 1488-1494, US.
O'Dell Le et al: Epipregnanolone and a novel synthetic neuroactive steroid reduce alcohol self-administration in rats, Pharmacology Biochemistry and Behavior, Elsevier, vol. 81, No. 3, Jul. 2005, pp. 543-550, US.
Stastna E et al: Synthesis of C3, C5, and C7 pregnane derivatives and their effect on NMDA receptor responses in cultured rat hippocampal neurons, Steroids, Elsevier Science Publishers, vol. 74, No. 2, Feb. 2009, pp. 256-263,New York, NY, US.
Kudova Eva et al: -Aspartate Receptor Inhibitors: Sulfated Neuroactive Steroids with Lipophilic D-Ring Modifications, Journal of Medicinal Chemistry, vol. 58, No. 15, Jul. 2015, pp. 5950-5966, US.

(Continued)

*Primary Examiner* — Paul V Ward
(74) *Attorney, Agent, or Firm* — Notaro, Michalos & Zaccaria P.C.

(57) ABSTRACT

Amphiphilic compounds with tetradecahydrophenanthrene skeleton and their enantiomers, exhibiting neuroprotective effects, their use in methods of treatment of neuropsychiatric disorders associated with an imbalance in glutamatergic neurotransmitter system, such as ischemic damage of CNS, neurodegenerative changes and disorders of CNS, affective disorders, depression, post-traumatic stress disorder and diseases related to stress, anxiety, schizophrenia and psychotic disorders, pain, addiction, multiple sclerosis, epilepsy, glioma, and a pharmaceutical composition containing compound.

6 Claims, No Drawings

(56) References Cited

OTHER PUBLICATIONS

International Search Report for PCT Application No. PCT/CZ2015/000096 Filed on Aug. 25, 2015.
International Written Opinion for PCT Application No. PCT/CZ2015/000096 Filed on Aug. 25, 2015.

AMPHIPHILIC COMPOUNDS WITH NEUROPROTECTIVE PROPERTIES

FIELD OF INVENTION

The present invention is in the field of pharmaceutical chemistry. The objective is a set of compounds which inhibit excessively activated modulate NMDA receptors, and thus protect the tissue of the central nervous system (CNS) against excessive action of glutamate.

BACKGROUND ART

NMDA receptors are multiprotein tetrameric complexes, which are composed of two NR1 subunits and two NR2A-2D subunits that form the ion channel for positive ions (Nature 438, 185-192 (2005)).

Glutamate is the major excitatory neurotransmitter in the central nervous system of mammals. Responses of the post synaptic neuron are generated during synaptic transmission via ionotropic and metabotropic glutamate receptors. N-Methyl-D-aspartate receptors (NMDA), AMPA and kainite receptors belong to the family of ionotropic glutamate receptors.

Although current evidence suggests the role of different subtypes of glutamate receptors in glutamate induced excitotoxicity, ionotropic receptors are considered to be a key player in these processes. Activation of ionotropic glutamate receptors leads to changes in intracellular concentration of ions, especially calcium and sodium. Toxicity of higher levels of glutamate is generally associated with an increase in intracellular $Ca^{2+}$ levels. Currently, it is relatively well established that there is a direct relationship between the excessive influx of calcium into the cells and glutamate-induced neuronal damage. Glutamate-induced pathological increase in intracellular calcium is attributed to prolonged activation of ionotropic glutamate receptors. Increases in intracellular calcium may trigger a cascade of neurotoxicity.

A number of preclinical studies have documented striking ability of NMDA antagonists to prevent an excessive action of glutamate on nerve cells and thereby reduce the impairment of the function of CNS. However, from the clinical point of view their neuroprotective potential is small. Due to the fact that NMDA receptors are one of the most widespread types of receptors in the CNS, their administration lead usually to a number of serious side effects (e.g. distortion, induction of motoric psychoses of the schizophrenic type, etc.).

On the other hand, a great variety of NMDA receptors and their different distribution at synapses and in the brain and various functional states of this receptor offers great possibility of seeking for agents that selectively affect only a specific group of NMDA receptors and thereby reduce the occurrence of unanticipated and undesirable effects while maintaining the neuroprotective activity (Pharmacol. Rev. 51, 7-61 (1999); Semin. Cell Dev. Biol. 17, 592-604 (2006); Top. Med. Chem. 6, 749-770 (2006); Anesth. Analg. 97, 1108-1116 (2003); Curr. Opin. Pharmacol. 6, 53-60 (2006); Curr. Opin. Investig. Drugs 4, 826-832 (2003).

Previous results showed that naturally occurring 3alpha, 5beta-pregnanolone sulfate affects the activity of NMDA receptors by the use-dependent manner. Due to this mechanism of action, pregnanolone sulfate has pronounced inhibitory action on NMDA receptors tonically activated by glutamate than phasically activated NMDA receptors during synaptic transmission. The activation of tonically activated extrasynaptic NMDA receptors is essential for the excitotoxic action of glutamate (J. Neurosci. 25, 8439-50 (2005)).

Therefore, we have started a development and testing of novel NMDA antagonists derived from neurosteroids. These newly synthesized compounds exhibit affinity for extrasynaptic NMDA receptors. Moreover, our previous electrophysiological studies have shown that this type of compounds binds only to the long-term opened-NMDA receptors. The supposed mechanism of the neuroprotective effect is blocking of excessive penetration of calcium into cells through the open NMDA receptors. As these compounds do not have affinity to other types of NMDA receptors, it is believed that they would minimally affect the signal transmission between neurons.

In the last decade, the biomedical research has been focused on research of the role of neurosteroids in the pathophysiology of many neuropsychiatric disorders and to assess therapeutic potential of these compounds. Mechanism of action of neurosteroids is associated with their activity on the NMDA and GABA receptors. Experimental studies with animal models suggest potential of neurosteroids to treat a variety of central nervous disorders, particularly neurodegenerative diseases, multiple sclerosis, affective disorders, alcoholism, pain, insomnia or schizophrenia (J. Pharm. Exp. Ther. 116, 1-6 (2007); J. Pharm. Exp. Ther. 293, 747 (2000)).

Neurosteroids play a crucial role in the regulation of stress and the related CNS disorders. The level of neurosteroids temporarily after exposure to stress increases, as it is an adaptive mechanism. On contrary, experimental models of chronic stress and depression on laboratory rodents show long-term reduced concentration of neurosteroids in the brain and in plasma, due to their reduced biosynthesis.

Similar findings are found in patients suffering from depression or premenstrual syndrome. These findings point to, a violation of homeostatic mechanisms in the CNS of neuropsychiatric disorders related to stress.

Among well-known neurosteroids belong pregnenolone, progesterone, dehydroepiandrosterone (DHEA) and its reduced metabolite, and sulfate esters. The regulation of the synthesis of neurosteroids in the CNS is not well known, but it is generally believed that the crutial is interaction of various types of cells. For example, progesterone synthesis by Schwann cells in peripheral nerves is regulated by diffuse signals from neurons.

Neurotrophic and neuroprotective effects of neurosteroids were shown both in cell cultures and by in vivo experiments. Progesterone plays an important role in neurological recovery from traumatic brain injury and spinal cord through mechanisms involving protection against excitotoxic cell damage, lipid peroxidation and induction of specific enzymes. For example, after spinal cord transection in rats progesterone increases the number of astrocytes expressing NO synthase just above and below the site of transection.

Neurosteroids thus significantly modulate the function of membrane receptors for neurotransmitters, in particular the $GABA_A$ receptor, NMDA receptor, and sigmal receptors. These mechanisms are responsible for psychopharmacological effects of steroids and partly explain their anticonvulsant, anxiolytic, sedative and neuroprotective effects as well as their influence on learning and memory processes.

For instance, pregnanolone sulfate was shown to be capable of reversing cognitive deficit in aged animals and exerting a protective effect on memory in several amnesia models of amnesia. Current studies have demonstrated direct effect of neurosteroids on intracellular receptors. Despite absence of direct evidence for binding of neurosteroids to corticoid receptors, they may obviously modulate their function indirectly, by interaction with protein kinases C and A, MAP-kinase or CaMKII. Moreover, pregnanolone and pregnanolone sulfate were shown to affect microtubule-associated proteins and increase the rate of microtubule polymeration, which may in turn affect neuronal plasticity. These newly described neurosteroid effects are still poorly understood, however, it can be assumed that they affect neuroprotectivity.

Sulfated and thus amphiphilic steroid compounds generally do not penetrate the blood-brain barrier, but it was demonstrated that intravenously administered pregnanolone sulfate reach the brain (Neuropharmacology 61, 61-68 (2011)). The transport of sulfated analogs is probably mediated by active exchange mechanisms associated with so-called organic anion transport protein (OATP), which is expressed in the cells of brain tissue.

Inhibitors of the NMDA receptor are also some steroid derivatives and in particular reduced derivatives of progesterone. Its neuroprotective properties are also described in the patent literature (US2012/71453 A1, 2012; WO 2009/108804 A and WO 2009/108809).

These drugs act only under specific conditions of certain structural prerequisites (J. Pharmacol. Exp. Ther. 293, 747-754 (2000)). An essential structural requirement is bent shape of the molecule; this requirement is accomplished by derivatives 3alpha, 5beta-configuration of the steroid skeleton, and also to a lesser extent derivatives with 3alpha, 5alpha-configuration. In addition, the activity is dependent on the presence of ionisable groups within a convenient distance from steroid skeleton, i.e. 2 to 8 atoms. This group may be positively or negatively charged. In previously published articles and patent literature was also always mentioned as essential structural element of the acetyl substituent in position 17 of the steroid skeleton. This structural element appears in progesterone, pregnenolone and pregnanolone (Br. J. Pharmacol. 166, 1069-1083 (2012); Steroids 76, 1409-1418, (2011); WO 2009 108 804 and J. Med. Chem. 8, 426-432 (1965)).

The exception is the patent application U.S. Pat. No. 3,132,160 (1964 patent was not granted) on derivatives of androstane with anesthetic and tranquility action. For the described compounds, however, is characteristic an oxygen atom at position C-11, analogously to clinically used pregnanolone analogue—alfaxalone. Due to the fact that the results of biological tests verifying biological properties of these compounds were never disclosed, we consider the activity specified in this patent to be speculative.

Neuroprotective effect of steroid derivatives with a charged substituent at the C-3 also claimed by two patent applications: WO2010003391 (Anionic pregnane compounds, method for Their Producing and Use of Them) and WO2012/110010 (Pregnanolone derivatives substituted in 3alpha-position with the cationic group, Their method of production, usage and pharmaceutical preparation Involving Them). Both documents claim pregnane derivatives (polar substituent at C-20), substituted at C-3 of an anionic or cationic group of the formula

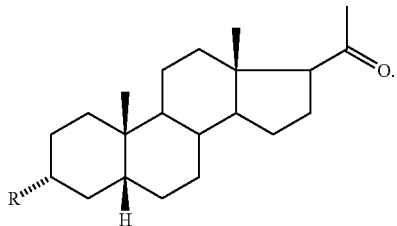

Derivatives claimed in the present application are not pregnanolone derivatives (these compounds do not have a keto group at the C-20). In case that the claimed compound has a carbonyl group, for the structure-activity reasons at position C-17 and thus, these compounds are androstane derivatives. In case of other polar modification, these derivatives have oxygen substituent in a lower oxidation state (ether) than the C-20 keto group.

Removal of polar substituent at position C-20, modifications and substitution of a D-ring at C-17 or C-16 with non-polar or lipophilic substituents, as well as complete removal of the steroidal D-ring, is likely to lead to better solubility of these derivatives in the membrane and a higher affinity to the NMDA receptor, resulting in some cases in multiple reduction of $IC_{50}$ values in comparison with the reference compound (3alpha, 5beta-pregnanolone sulfate). Our claimed compounds show that a higher degree of inhibition and $IC_{50}$ values lower than the reference compound can not generally be predicted, since the substitution or modification at the C- or D-ring in combination with the size and composition of the substituent at C-3 is always unique and it is not possible to predict in advance and to suggest structure by an additive approach. The above mentioned claims are illustrated by examples of substances (Table II) with an $IC_{50}$ value lower than the reference compound.

DESCRIPTION OF THE INVENTION

The present invention relates to compounds with a protective effect on the nervous system the structure of which comprises a substituted tetradecahydrophenanthrene formula I.

They are useful in the treatment of traumatic brain injury, ischaemia, Alzheimer's and Parkinson's disease, inflammatory processes of the nervous system, vascular dementia, ischemia of fetuses and neonatals, neuropathic pain, or in similar processes in human and veterinary medicine.

The invention also includes therapeutics composed from described compounds.

Tetradecahydrophenanthrene skeleton can have following configuration:
(2R,4aS,4bS,8aR,10aR)-tetradecahydrophenanthrene
(2S,4aS,4bS,8aR,10aR)-tetradecahydrophenanthrene
(2S,4aR,4bR,8aS,10aS)-tetradecahydrophenanthrene,

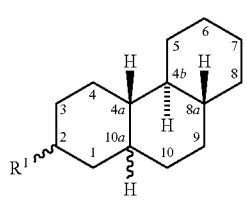

(4aS,4bS,8aR,10aR)-tetradecahydrophenantrene.

The invention thus covers amphiphilic compounds with tetradecahydrophenanthrene skeleton of general formula I,

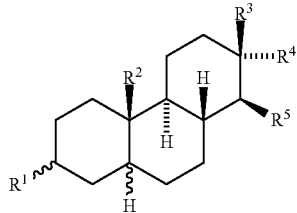

(I)

where $R^1$ is selected from group of (—$OSO_3pyH$), (—$OSO_3Na$), (—$OSO_3H$), NaOOC—$R^6$—C($R^7$)—$R^8$—, HOOC—$R^6$—C($R^7$)—$R^8$—, HOOC—C($R^7$)—$R^8$—, or $R^9$—$R^{10}$—C($R^{11}$)—$R^{12}$—, where $R^6$ means straight or branched chain of $C_1$ to $C_6$ alkylene or $C_2$ to $C_6$ alkenylene, any of them unsubstituted or substituted with one or more halogen atoms or amino group or amino group protected by protecting groups, preferably by tert-butylcarbonyl, or $R^6$ means trivalent —CH(CH$_2$—)$_2$ alkylene that forms with the carbon carrying $R^7$ and with $R^8$ being nitrogen a five-membered ring;

$R^7$ means atom of oxygen, nitrogen or sulphur bound by double bond or two atoms of hydrogen, $R^8$ means any at least divalent atom, preferably nitrogen, oxygen or carbon, $R^9$ means a cationic group selected from groups of guanidinyl formula,

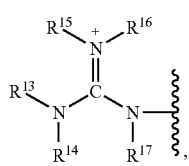

(a)

or quaternary ammonium groups of the formula

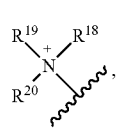

(b)

where $R^{13}$ to $R^{20}$ are hydrogen atoms or $C_1$ to $C_6$ alkyl or $C_2$ to $C_6$ alkenyl group with direct or branched chain, $R^{10}$ means straight or branched $C_1$ to $C_6$ alkylene or $C_2$ to $C_6$, both unsubstituted or substituted by one to 10 halogen atoms or by amino group which is primary or substituted by $C_1$ to $C_4$ alkyl with direct or branched chain;

$R^{11}$ is formed by atom of oxygen, nitrogen or sulphur bound by double bond or by two atoms of hydrogen, and $R^{12}$ is chosen from group of oxygen, nitrogen or carbon and when $R^{12}$ is carbon or nitrogen, its next valences are occupied by hydrogen or hydrogens, while any of hydrogen can be substituted by $C_1$ to $C_4$ alkyl or $C_2$ to $C_4$ alkenyl;

$R^2$ means hydrogen atom or methyl;

$R^3$ means a) hydrogen atom and then i) $R^4$ and $R^5$ are independently hydrogen atoms, or ii) one of $R^4$ and $R^5$ means hydrogen atom and the other one means straight or branched chain $C_1$ to $C_6$ alkyl or $C_2$ to $C_6$ alkenyl, which is optionally substituted by 1 to 13 halogen atoms in case of alkyl and by 1 to 9 halogen atoms in case of alkenyl, or by atom of oxygen or sulphur bound by a double bond, while one of the ethylene groups in the chain is optionally substituted by oxygen or sulphur atom, b) straight or branched $C_1$ to $C_6$ alkyl or $C_2$ to $C_6$ alkenyl, which is optionally substituted by 1 to 13 halogen atoms in case of alkyl or by 1 to 9 halogen atoms in case of alkenyl, or by atom of oxygen or sulphur bound by a double bond, while one of the methylene groups in the chain is optionally substituted by oxygen or sulphur atom, and then $R^4$ and $R^5$ are independently to each other hydrogen atoms, or c) $C_5$ or $C_6$ alicyclic or aromatic substituent, while carbon atoms can be functionalized by 1 to 8 atoms of halogen in case of five-membered alicyclic ring, or 1 to 10 halogen atoms in case of six-membered alicyclic ring or by 1 to 4 halogen atoms in case of five-membered aromatic ring or 1-5 halogen atoms in case of six-membered aromatic ring; and then i) $R^5$ is selected from group of hydrogen atom, or $C_1$ to $C_6$ alkyl or $C_2$ to $C_6$ alkenyl with direct or branched chain, which is optionally substituted by 1 to 13 halogen atoms in case of alkyl and by 1 to 9 halogen atoms in case of alkenyl, or by double bond bound atom of oxygen or sulphur, while one of the methylene groups in the chain is optionally substituted by oxygen or sulphur atom, or ii) $R^4$ and $R^5$ means alkylene or alkenylene substituent —(CH$_m$)$_n$—, where n=3-4, m=1-2, forming with parent carbon atoms of the skeleton at position 7 and 8 saturated or unsaturated 5- or 6-membered cycle, where hydrogen atoms of the alkenylen substituent are optionally substituted at least by one halogen atom or $C_1$ to $C_4$ alkyl or $C_2$ to $C_4$ alkenyl, both with direct or branched chain; or one methylene group of the alkylen substituent forming the ring can be replaced by carbonyl group and the carbon atom at the adjoining position can be substituted by another methylene group, or it can be replaced by oxygen or sulphur atom, while in case of sulphur atom, this can be further functionalized by oxygen atom; or the hydrogens of one methylene group of alkylen substituent can be replaced by —O—CH$_2$—, to form an oxirane ring;

d) substituent —CH$_2$—O—CH(CH$_3$)—, then together with the first carbon of alkylen group formed by $R^4$ and $R^5$, where $R^4$ and $R^5$ means alkylen substituent —(CH$_2$)$_3$— forms saturated and methylated heterocycle;

and enantiomers of compound of general formula I, with the proviso that in formula I are excluded compounds, where $R^1$ means HO$_2$C—$R^6$CR$^7$—$R^8$—, $R^6$ means —(CH$_2$)$_2$—, $R^7$ means oxygen atom bound by double bond and $R^8$ means oxygen atom, while $R^2$ and $R^3$ mean methyls, $R^4$ and $R^5$ together forms group —(CH$_2$)$_3$— forming with parent carbon atoms of tetradecahydrophenanthrene skeleton at position 7 and 8 saturated five-membered ring; with absolute configuration 3R,5S,8S,9S,10S,13S,14S.

Halogen is chosen from group of —F, —Cl, —Br, —I.

Alkyl is straight or branched saturated hydrocarbon substituent, in one embodiment containing one to six carbon atoms, in another embodiment from one to four carbon atoms, selected from methyl, ethyl, n-propyl, iso-propyl, n-butyl, sec-butyl, tert-butyl, isobutyl, amyl, t-amyl, iso-amyl, n-pentyl, n-hexyl and similarly; removal of one hydrogen atom from the terminal alkyl $CH_3$ group will form corresponding alkylene.

Alkenyl is an unsaturated hydrocarbon substituent comprising dienes and trienes of straight or branched chains containing 2 to 6 carbon atoms, or 2 to 4 carbon atoms, preferably selected from vinyl, allyl, 1-butenyl, 2-butenyl, 1-pentenyl, 2-pentenyl, 3-pentenyl, 1-hexenyl, 2-hexenyl, 3-hexenyl and similarly; removal of one hydrogen atom of the end group CH or $CH_2$ form the corresponding alkenylene.

Cycloalkyl or alicyclic group is selected from saturated cyclic hydrocarbon radicals containing 3 to 6 carbon atoms, preferably cyclopropyl, cyclobutyl, cyclopentyl, cyclohexyl.

The cycloalkenyl group is preferably selected from cyclopropenyl, 1-cyclobutenyl, 2-cyclobutenyl, 1-cyclopentenyl, 2-cyclopentenyl, 3-cyclopentenyl, 1-cyclohexenyl, 2-cyclohexenyl, 3-cyclohexenyl.

An aromatic group with six carbon atoms, either alone or in combination with other radicals, is preferably selected from phenyl.

Heterocycle or heterocyclic group is selected from $C_3$ to $C_6$ non-aromatic cyclic hydrocarbons containing one or more heteroatoms selected from O, N and S. Non-aromatic hydrocarbons containing the above heteroatoms, may be saturated or partially saturated monocyclic radicals. Abbreviation pyH means pyridinium salt of particular sulfate.

In a preferred embodiment the present invention are the following compounds of Formula I:
pyridinium (2R,4aS,8aR,10aR)-4a-methyltetradecahydrophenanthren-2-yl 2-sulfate (8),
pyridinium (2R,4aS,4bS,7S,8S,8aS,10aR)-7-(meth oxymethyl)-4a,7,8-trimethyltetradecahydrophenanthren-2-yl 2-sulfate (18),
4-(((2R,4aS,4bS,7S,8aS,10aR)-7-(methoxymethyl)-4a,7,8-trimethyltetradecahydrophenanthren-2-yl)oxy)-4-oxobutanoic acid (19),
pyridinium (2R,4aS,7S,8S,10aR)-7-(methoxycarbonyl)-4a,7,8-trimethyltetradecahydrophenanthren-2-yl 2-sulfate (22),
4-(((2R,4aS,4bS,7R,8aS,10aR)-4a,7-dimethyltetradecahydrophenanthren-2-yl)oxy)-4-oxobutanoic acid (34),
pyridinium (2R,4aS,4bS,7R,8aS,10aR)-4a,7-dimethyltetradecahydrophenanthren-2-yl 2-sulfate (35), methyl (2S,4aS,4bS,7R,8aR,10aS)-2,4b-dimethyl-7-(sulfooxy)tetradecahydrophenanthren-2-carboxylate (40),
pyridinium (3R,5R,8S,9S,10S,13S,14S)-10,13-dimethylhexadecahydro-1H-cyclopenta-[a]phenanthren-3-yl 3-sulfate (49),
2-(((3R,5R,8S,9S,10S,13S,14S)-10,13-dimethylhexadecahydro-1H-cyclopenta[a]phenanthren-3-yl)oxy)-2-oxoacetic acid (50),
2-(((3R,5R,8S,9S,10S,13S,14S)-10,13-dimethylhexadecahydro-1H-cyclopenta[a]phenanthren-3-yl)oxy)-2-oxopropanoic acid (51),
2-(((3R,5R,10S,13S,14S)-10,13-dimethylhexadecahydro-1H-cyclopenta[a]phenanthren-3-yl)amino)-2-oxoacetic acid (59),
((3R,5R,8S,9S,10S,13S,14S)-10,13-dimethylhexadecahydro-1H-cyclopenta[a]phenanthren-3-yl)amino)-3-oxopropanoic acid (61),
4-(((3R,5R,8S,9S,10S,13S,14S)-10,13-dimethylhexadecahydro-1H-cyclopenta[a]phenanthren-3-yl)oxy)-N,N,N-trimethyl-4-oxobutan-1-ammonium chloride (62),
4-(((3R,5R,8R,9S,10S,13R,14S)-10,13-dimethyl-2,3,4,5,6,7,8,9,10,11,12,13,14,15-tetradecahydro-1H-cyclopenta[a]phenanthren-3-yl)oxy)-4-oxobutanoic acid (64),
3-(((3R,5R,8R,9S,10S,13R,14S)-10,13-dimethyl-2,3,4,5,6,7,8,9,10,11,12,13,14,15-tetradecahydro-1H-cyclopenta[a]phenanthren-3-yl)oxy)-3-oxopropanoic acid (65),
3-(((3R,5R,8R,10S,13S,14S)-10,13-dimethyl-17-methylenehexadecahydro-1H-cyclopenta[a]phenanthren-3-yl)oxy)-3-oxopropanoic acid (67),
4-(((3R,5R,8R,9S,10S,13S,14S)-10,13-dimethyl-17-methylenehexadecahydro-1H-cyclopenta[a]phenanthren-3-yl)oxy)-4-oxobutanoic acid (68),
4-(((3R,5R,8R,9S,10S,13S,14S)-10,13-dimethyl-17-methylenehexadecahydro-1H-cyclopenta[a]phenanthren-3-yl)oxy)-4-oxopentanoic acid (69),
2-(((3R,5R,8R,9S,10S,13S,14S)-10,13-dimethyl-17-oxohexadecahydro-1H-cyclopenta[a]phenanthren-3-yl)acetic acid (74),
2-(((3R,5R,8R,9S,10S,13S,14S)-10,13-dimethyl-17-methylenehexadecahydro-1H-cyclopenta[a]phenanthren-3-yl)oxy)-N,N,N-trimethyl-2-oxoethan-1-ammonium chloride (76),
3-(((3R,5R,8R,9S,10S,13S,14S,Z)-17-ethylidene-10,13-dimethylhexadecahydro-1H-cyclopenta[a]phenanthren-3-yl)oxy)-3-oxopropanoic acid (83),
5-(((3R,5R,8R,9S,10S,13S,14S,Z)-17-ethylidene-10,13-dimethylhexadecahydro-1H-cyclopenta[a]phenanthren-3-yl)oxy)-5-oxopentanoic acid (85),
3-(((3R,5R,8R,9S,10S,13S,14S,17R)-10,13-dimethyl-17-(prop-1-en-2-yl)hexadecahydro-1H-cyclopenta[a]phenanthren-3-yl)oxy)-3-oxopropanoic acid (88),
pyridinium (3R,5R,8R,9S,10S,13S,14S,17 S)-17-iodo-10,13-dimethylhexadecahydro-1H-cyclopenta[a]phenanthren-3-yl 3-Sulfate (93),
pyridinium (3R,5R,8R,9S,10S,13S,14S)-17,17-difluoro-10,13-dimethylhexadecahydro-1H-cyclopenta[a]phenanthren-3-yl 3-Sulfate (95),
pyridinium (3R,5R,8R,9S,10S,13S,14S,17S)-10,13-dimethylhexadecahydrospiro[cyclopenta-[a]phenanthren-17,2'-oxiran]-3-yl 3-Sulfate (97),
pyridinium (2R,4aS,4bS,6aS,10bS,6aS,12aR)-4a,6a-dimethyloctadecahydrochrysen-2-yl 2-sulfate (101), (4S)-4-amino-5-(((2R,4aS,4bS,6aS,10bS,12aR)-4a,6a-dimethyloctadecahydrochrysen-2-yl)oxy)-5-oxopentanoic acid (106),
pyridinium (3R,5R,8S,9S,10S,13R,14S)-10,13-dimethyl-16-methylenehexadecahydro-1H-cyclopenta[a]phenanthren-3-yl 3-sulfate (114),
pyridinium (3R,5R,8R,9S,10S,13S,14S)-10,13-dimethyl-17-methylenehexadecahydro-1H-cyclopenta[a]phenanthren-3-yl 3-sulfate (116),
pyridinium (3R,5R,8S,9S,10S,13R,14S,17S)-10,13,17-trimethylhexadecahydro-1H-cyclopenta[a]phenanthren-3-yl 3-sulfate (117),
pyridinium (3R,5R,8S,9S,10S,13R,14R,17R)-10,17-dimethylhexadecahydro-1H-cyclopenta[a]phenanthren-3-yl 3-sulfate (118),
pyridinium (3R,5R,8S,9S,10S,13R,14R,17S)-10,17-dimethylhexadecahydro-1H-cyclopenta[a]phenanthren-3-yl 3-sulfate (119), pyridinium (3R,5R,8S,9S,10S,13R,14S,17S)-17-ethyl-10,13-dimethylhexadecahydro-1H-cyclopenta[a]phenanthren-3-yl 3-sulfate (120),
pyridinium (3R,5R,8R,9S,10S,13S,14S,17R)-10,13-dimethyl-17-(prop-1-en-2-yl)hexadecahydro-1H-cyclopenta[a]phenanthren-3-yl 3-sulfate (121),
pyridinium (3R,5R,8R,9S,10S,13R,14S,17R)-17-isopropyl-10,13-dimethylhexadecahydro-1H-cyclopenta[a]phenanthren-3-yl 3-sulfate (122),
pyridinium (3R,5R,8R,9S,10S,13R,14S,17R)-17-((R)-sec-butyl)-10,13-dimethylhexadecahydro-1H-cyclopenta[a]phenanthren-3-yl 3-sulfate (123),
pyridinium (3S,3aS,5bR,7aR,9R,11aS,11bS,13aR)-3,11a-dimethylhexadecahydro-1H,3H-naphtho[2',1':4,5]indeno[1,7a-c]furan-9-yl 9-sulfate (124),
pyridinium (3R,5R,8R,9R,10S,13S,14S)-13-methylhexadecahydro-1H-cyclopenta[a]phenanthren-3-yl 3-sulfate (126),
pyridinium (3R,5S,8R,9R,10S,13S,14S)-10,13-dimethylhexadecahydro-1H-cyclopenta[a]phenanthren-3-yl 3-sulfate (127),
pyridinium (2S,4aR,4bR,8aS,10aS)-4a-methyltetradecahydrophenanthren-2-yl 2-sulfate (128), (4S)-4-amino-5-(((3R,5R,8S,9S,10S,13S,14S)-10,13-dimethylhexadecahydro-1H-cyclopenta[a]phenanthren-3-yl)oxy)-5-oxopentanoic acid (130),
1-((3R,5R,8S,9S,10S,13S,14S)-10,13-Dimethylhexadecahydro-1H-cyclopenta[a]phenanthren-3-yl)-5-oxopyrrolidine-3-carboxylic acid (131), mixture of isomers
sodium 2-oxo-2-(((3R,5R,8S,9S,10S,13R,14S,17S)-10,13,17-trimethylhexadecahydro-1H-cyclopenta[a]phenanthren-3-yl)amino)acetate (138),
3-oxo-3-(((3R,5R,8S,9S,10S,13R,14S,17S)-10,13,17-trimethylhexadecahydro-1H-cyclopenta[a]phenanthren-3-yl)amino)propanoic acid (140),
sodium 2-(((3R,5R,8R,9S,10S,13S,14S)-17-((R)-sec-butyl)-10,13-dimethylhexadecahydro-1H-cyclopenta[a]phenanthren-3-yl)amino)-2-oxoacetate (148),
3-(((3R,5R,8R,9S,10S,13S,14S)-17-((R)-sec-butyl)-10,13-dimethylhexadecahydro-1H-cyclopenta[a]phenanthren-3-yl)amino)-3-oxopropanoic acid (149),
2-(((3R,5R,8R,9S,10S,13S,14S,Z)-17-ethylidene-10,13-dimethylhexadecahydro-1H-cyclopenta[a]phenanthren-3-yl)amino)-2-oxoacetic acid (154),
3-(((3R,5R,8R,9S,10S,13S,14S,Z)-7-ethylidene-10,13-dimethylhexadecahydro-1H-cyclopenta[a]phenanthren-3-yl)amino)-3-oxopropanoic acid (155).

Another object of the present invention are amphiphilic compounds with tetradecahydrophenanthrene skeleton of general formula I and the corresponding specific compounds mentioned above, for use as a medicament.

Another aspect of the invention are also amphiphilic compounds with tetradecahydrophenanthrene skeleton of general formula I and the corresponding above-mentioned specific compounds for use in treating neuropsychiatric disorders associated with imbalances of glutamatergic neurotransmitter system, such as ischemic damage of the central nervous system, neurodegenerative changes and disorders of CNS, affective disorders, depression, post-traumatic stress disorder, and diseases related to stress, anxiety, schizophrenia and psychotic disorders, pain, addiction, multiple sclerosis, epilepsy, glioma.

The present invention relates also to the use of amphiphilic compounds with tetradecahydrophenanthrene skeleton of formula I for the preparation of a veterinarian or human pharmaceutical drug or composition comprising it for treating of neuropsychiatric disorders associated with imbalance of glutamatergic neurotransmitter system, such as ischemic damage to the central nervous system, neurodegenerative changes and disorders of CNS, affective disorders, depression, post-traumatic stress disorder, and diseases related to stress, anxiety, schizophrenia and psychotic disorders, pain, addiction, multiple sclerosis, epilepsy, glioma.

The invention further includes the use of amphiphilic compounds with tetradecahydrophenanthrene skeleton having the formula I for the manufacture of standard neuroprotective agents, antidepressants, antianxiety, mood stabilizers, hypnotives, sedatives, analgesics, anesthetics, antipsychotics, neuroleptics and procognitives or analytical standards used in experimental research and analytical chemistry or as compounds contained in food additives or cosmetic preparations intended for improving the response of the individual parts of the organism to increased oxidative stress in particular, the nutrition and caused by free radicals, or by aging.

The invention also provides a pharmaceutical composition for human or veterinary use, comprising as active ingredient a compound having an amphiphilic tetradecahydrophenanthrene skeleton of general formula I or one of the above-mentioned specific amphiphilic compounds corresponding to general formula I.

Finally, the present invention also includes the above mentioned pharmaceutical composition for treating neuropsychiatric disorders associated with an imbalance in glutamatergic neurotransmitter system, such as ischemic damage of CNS, neurodegenerative changes and disorders of CNS, affective disorders, depression, post-traumatic stress disorder and related diseases stress, anxiety, schizophrenia and psychotic disorders, pain, addiction, multiple sclerosis, epilepsy, glioma.

The present invention will be further illustrated by Examples, which should not be construed as limiting the scope of the invention.

EXAMPLES

Abbreviation List $CHCl_3$ chloroform
DMSO dimethylsulfoxide
MS mass spectrometry
HRMS high resolution mass spectrometry
Boc tert-butoxycarbonyl
EI electron ionization
ESI electrospray ionization
eq. equivalent
IR infrared spectroscopy
NMR nuclear magnetic resonance
t-Bu tertial butyl
Ac acetyl
HEK human embryonic kidney cells
GFP green fluorescent protein
$IC_{50}$ the half maximal inhibitory concentration
Opti-MEM® I minimum essential media, Invitrogen's product
DHEA 5-dehydroepiandrosterone
EGTA ethylene glycol tetraacetic acid
EDTA ethylene diamine tetraacetic acid
HEPES 4-(2-hydroxyethyl)-1-piperazineethanesulfonic acid
Experimental Part—Chemistry Melting points were measured at Hund Wetzlar H-600 (Helmut Hund, Germany). Samples for analysis were dried over phosphorous pentoxide at 50° C. and a pressure of 100 mbar. Optical rotation was measured in chloroform Autopol IV polarimeter (Rudolph Research Analytical, Flanders, USA), $[\alpha]_D$ values are shown in $10^{-1} \cdot \deg \cdot cm^2 \cdot g$ and were compensated to a standard temperature of 20° C. Infrared spectra were measured in chloroform or sample in potassium bromide tablets using a Bruker IFS 55 wave numbers are given in $cm^{-1}$. $^1H$ NMR spectra were measured in FT mode at 24° C. and 400 MHz on a Bruker AVANCE-400 or deuteromethanol or deuterochloroform with tetramethylsilane (TMS) as internal standard. Chemical shifts are given in ppm (δ-scale), coupling constants (J) are given in Hz. Signal multiplicities are designated as follows: s—singlet, d—doublet, t—triplet, q—quartet, m—multiplet, b denotes br (broad). All spectra were interpreted as the spectra of the first order. For description of NMR spectra, the classical cholesterol numbering system was used. Mass spectra were measured on a ZAB-EQ spectrometer (at 70 eV) or LCQ Classic (Thermo Finnigan). For the work-up, the aqueous hydrochloric acid solution (5%), or saturated aqueous sodium bicarbonate were used. Thin layer chromatography (TLC) was performed on plates coated with a thin layer of silica gel (ICN Biochemicals). Preparative column chromatography was performed on silica gel Fluka (60 microns). For detection of the compounds on TLC plates was used immersion in aqueous sulfuric acid solution (20 ml of 98% sulfuric acid) in methanol (250 ml) followed by heating at 300-400° C. Solvents were evaporated from the solution by rotary evaporation (0.25 kPa) at 40° C. bath. The mobile phase for column chromatography is shown always in the experiment. For the names of the compounds it is preferably recommended IUPAC nomenclature (PIN) and in cases where it was suitable terminology derived from appropriate steroid derivatives. For the preparation of the active compounds tested were used de novo synthesis and modification of suitable commercially available precursors.

General Procedures

General Procedure I—Synthesis of C-3 Sulfate

To a mixture of alcohol and sulphur trioxide-pyridine complex (2 eq.), dried under reduced pressure (30 min, 25° C., 100 Pa) was added freshly dried chloroform (10 ml per 100 mg) and dried pyridine (3 drops) and the reaction mixture was stirred under inert atmosphere at room temperature for 4 h. The reaction mixture was then cooled to −5° C. for 18 h, cooled and filtered through cotton wool. The filtrate was evaporated under reduced pressure and the residue is dried for 1 hour (25° C., 100 mbar). The residue was re-slurried in freshly dried dichloromethane (minimum volume) and cooled to −5° C. for 2 h. The solids were filtered, the filtrate evaporated under reduced pressure and dried (1 h, 25° C., 100 mbar).

General Procedure II—Synthesis of C-3 Hemisuccinate

To a mixture of alcohol and succinic anhydride (7 eq., dried overnight at 50° C.) was added dry pyridine (5 ml per 100 mg) and 4-(N,N-dimethylamino) pyridine (0.5 eq.). The reaction mixture was heated to 120° C. and the progress was monitored on TLC. The mixture was then poured into water and the product extracted with chloroform. The combined organic extracts were washed with saturated aqueous sodium chloride solution and dried over anhydrous sodium sulfate. The solvents were evaporated under reduced pressure.

General Procedure III—Synthesis of C-3 Hemimalonate

Alcohol in dried toluene (5 mL per 100 mg) with pyridine (0.75 mL per 100 mg) was added to a dry reaction flask with 2,2-dimethyl-4,6-dioxo-1,3-dioxolane (Meldrum's acid, 1.1 eq.). The reaction mixture was heated with stirring at 80° C. and the progress was monitored on TLC. It was then cooled to room temperature, diluted with water and acidified with dilute hydrochloric acid (5%). The steroid was extracted with ethyl acetate, the combined organic phases were washed with dilute hydrochloric acid (5%), water and dried over anhydrous sodium sulfate. The solvents were evaporated under reduced pressure.

General Procedure IV—Synthesis of C-3 Hemiglutarate

Alcohol and glutaric anhydride (258 mg, 2.26 mmol) were dried at 50° C. overnight. Then, dried pyridine (3 mL per 100 mg) and 4-(N,N-dimethylamino)pyridine (0.3 eq.) were added. The mixture was heated at 120° C. and the progress was monitored on TLC. The reaction mixture was then cooled to room temperature, quenched by pouring reagents into water and the product extracted with chloroform. The combined organic extracts were washed with brine and dried with anhydrous magnesium sulfate. The solvents were evaporated under reduced pressure.

General Procedure V—Catalytic Hydrogenation

To a solution of the appropriate compound in ethanol (5 mL per 100 mg) and ethyl acetate (2.5 ml per 100 mg) was added the catalyst (Pd/CaCO$_3$, 5%) and the mixture was vigorously stirred under a slight positive pressure of hydrogen at room temperature and the progress was monitored on TLC. The catalyst was removed by filtration and the solvent evaporated under reduced pressure.

General Procedure VI—Wilkinson Decarbonylation

Mixture of the appropriate compound and tris(triphenylphosphine)rhodium(I) chloride (1.1 eq.) in benzonitrile (24 ml per 1.3 g) was heated under inert atmosphere at 160° C. for 20 h. The reaction mixture was cooled to room temperature and filtered to remove a yellow solid. The filtrate was evaporated under reduced pressure.

General Procedure VII—Wittig Reaction Using n-Butyl Lithium n-Butyl lithium (2.5M in hexane, 1.1 eq.) was added cold dropwise to a solution of methyltriphenylphosphonium iodide (1 eq.) in dried tetrahydrofuran (30 ml per 4 g) under an inert atmosphere of nitrogen and the mixture was stirred and heated at 80° C. for 2 hours. Then, a solution of compound (0.5 eq.) in dried tetrahydrofuran (minimum amount) was added. The reaction mixture was stirred at 80° C. and the progress was monitored on TLC. The reaction was quenched with saturated ammonium chloride solution. The product was extracted into chloroform; the combined organic extracts were washed with brine and dried over anhydrous sodium sulfate. The solvents were evaporated under reduced pressure.

General Procedure VIII—Tosylation

A solution of particular compound, 4-dimethylaminopyridine (0.1 eq.), and p-TsCl (2 eq.) in anhydrous pyridine (75 ml per 4 g) was stirred at rt overnight. The reaction mixture was poured into ice-water and the precipitated white solid was collected by filtration, washed with water and dried.

General Procedure IX—Substitution of Tosylate Protecting Group with Alkali Azide A mixture of tosylated derivative and sodium azide (8 eq.) in N,N'-dimethylformamide (65 ml per 6 g) was heated under inert atmosphere at 55° C. for 4 h. Then, the reaction mixture was poured into water and the product was extracted with ethyl acetate. The combined organic extracts were washed with 5% aqueous HCl, water, saturated aqueous solution of sodium bicarbonate, water, dried and the solvents were evaporated under reduced pressure.

General Procedure X—Reaction of C-3 Amino Group with Methyl 3-Chloro-oxopropionate A mixture of amine (202 mg, 0.52 mmol) in dry dichloromethane (4 ml per 200 mg) was added dropwise to a cooled (0° C.) stirred mixture of methyl 3-chloro-3-oxopropionate (3.5 eq.) and dry dichloromethane (3 ml per 0.2 ml of the reagent) under inert atmosphere. The reaction mixture was stirred at rt for 1.5 h, then it was poured into ammoniacal water, product was extracted with chloroform, the combined organic extracts were washed with brine, dried and the solvents were evaporated under reduced pressure.
General Procedure XI—Reaction of C-3 Amino Group with Ethyl Chlorooxoacetate A mixture of amine in dry benzene (15 ml per 100 mg) and pyridine (1 ml per 100 mg) was added dropwise to a cooled (0° C.) stirred mixture of benzene (10 ml per 100 mg) and ethyl chlorooxoacetate (5 eq.) under inert atmosphere. The reaction mixture was stirred at room temperature for 1.5 h. The precipitated pyridine hydrochloride was filtered off, filtrate was washed twice with 5% aqueous sulfuric acid and then with water. The solvent was evaporated under reduced pressure.

Example 1: (S)-6-(Ethylendioxy)-8a-methyl-3,4,6,7,8,8a-bexahydronaphtalen-1(2H)-one (2)

Diketone 1 (7.36 g, 41.3 mmol), triethyl orthoformiate (7.58 ml, 45.6 mmol), and ethylene glycol (12.7 ml, 228 mmol) were dissolved in DCM (50 ml) and cooled to −10° C. Then, trifluoromethanesulfonate (150 ml, 830 µmol) was added and the mixture was stirred at −10° C. for 1 h. Then, triethylamine (200 ml, 1.43 mmol) was added and the reaction mixture was poured into saturated aqueous sodium bicarbonate solution. The product was extracted into dichloromethane (3×50 ml). The combined organic extracts were dried over anhydrous magnesium sulfate and the solvents evaporated under reduced pressure. Residue was purified by column chromatography on silica gel (150 g, 20% ethyl acetate in petroleum ether) affording 7.88 g (86%) of monoketal 2: mp 48-51° C., $[\alpha]_D^{20}$ +97.7 (c 0.27, CHCl$_3$). $^1$H NMR (400 MHz, CDCl$_3$): δ 1.32 (s, 3H, H-19), 1.65 (qt, $J_1$=13.3, $J_2$=4.6, 1H, H-7b), 1.69-1.77 (m, 1H, H-1b), 1.77-1.89 (m, 2H, H-2), 1.99-2.07 (m, 1H, H-7a), 2.16-2.08 (m, 1H, H-1b), 2.27 (dddd, $J_1$=14.1, $J_2$=4.5, $J_3$=2.7, $J_4$=2.1, 1H, H-6b), 2.37 (dddd, $J_1$=15.2, $J_2$=4.7, $J_3$=2.9, $J_4$=1.8 Hz, 1H, CH-8b), 2.56 (dddd, $J_1$=14.0, $J_2$=13.5, $J_3$=5.0, $J_4$=1.9, 1H, H-6a), 2.64 (ddd, $J_1$=15.2, $J_2$=13.4, $J_3$=6.3 1H, H-8a), 5.41 (t, J=1.3, 1H, H-4), 3.87-4.02 (m, 4H, OCH$_2$CH$_2$O). $^{13}$C NMR (101 MHz, CDCl$_3$): δ 212.52 (C, C-9), 146.58 (C, C-5), 123.44 (CH, C-4), 105.41 (C, C-3), 64.58 (CH$_2$, OCH$_2$CH$_2$O), 64.28 (CH$_2$, OCH$_2$CH$_2$O), 50.23 (C, C-10), 37.82 (CH$_2$, C-8), 30.82 (CH$_2$, C-6), 29.77 (CH$_2$, C-2), 28.60 (CH$_2$, C-1), 24.27 (CH$_2$, C-7), 23.81 (CH$_3$, C-19). IR spectrum (CHCl$_3$): 2953, 1461, 1447, 1442 (CH$_2$); 2975 2885 (CH$_3$); 1711 (C=O); 1661 (C=C). MS (ESI) m/z: 223 (40%, (M+H), 245 (100%, M+Na). HR-MS (ESI) m/z: For C$_{13}$H$_{18}$NaO$_3$ (M+Na) calcd 245.1148; found: 245.1148. For C$_{13}$H$_{18}$O$_3$ (222.3) calcd: 70.24% C, 8.16% H; found: 69.86% C, 8.19% H.

Example 2: (S)-7-(Ethylenedioxy)-4b-methyl-1,2,4b,5,6,7,9,10-octahydrophenanthren-3(4H)-one (3a) and (4bS,10aS)-7-(ethylenedioxy)-4b-methyl-1,2,4b,5,6,7,10,10a-octahydrophenanthren-3(9H)-one (3b)

Sodium hydride (9.39 g, 235 mmol, 60% suspension in oil, washed with tetrahydrofuran, 3×25 ml) in tetrahydrofuran (10 ml) was added to a cooled (0° C.) solution of ketone 2 (20.87 g, 93.89 mmol) in dry ethyl formate (250 ml). Then, methanol (3.80 ml, 93.9 mmol) was added dropwise over 15 min at 0° C. The reaction mixture got thickened within a few minutes and after 30 minutes was warmed to room temperature. After an additional 30 min, it was quenched with saturated ammonium chloride solution (400 ml) and the product was extracted with ethyl acetate (3×100 ml). The combined organic extracts were dried over anhydrous sodium sulfate, the solvent evaporated under reduced pressure to afford a quantitative amount of the crystalline formyl derivative: $^1$H NMR (400 MHz, CDCl$_3$): δ 1.37 (3H, s, CH$_3$-19), 1.82-2.13 (4H, m, CH$_2$-1, CH$_2$-2), 2.22-2.43 (2H, m, CH$_2$-6), 2.30-2.57 (2H, m, CH$_2$-7), 3.84-4.05 (4H, m, OCH$_2$CH$_2$O), 5.39 (1H, t, J=1.1, CH-4), 8.54 (1H, s, CHOH), 14.67 (1H, bs, OH). $^{13}$C NMR (101 MHz, CDCl$_3$): δ 190.20 (C, C-9), 185.76 (CH, CHOH), 144.96 (C, C-5), 122.52 (CH, C-4), 106.76 (C, C-8), 105.32 (C, C-3), 64.72 (CH$_2$, OCH$_2$CH$_2$O), 64.26 (CH$_2$, OCH$_2$CH$_2$O), 41.98 (C, C-10), 30.34 (CH$_2$, C-1), 29.89 (CH$_2$, C-2), 29.14 (CH$_2$, C-6), 24.28 (CH$_2$, C-7), 23.75 (CH$_3$, C-19).

Butenone (8.77 ml, 105 mmol) and triethylamine (245 ml, 1.75 mmol) was added to the formyl derivative and the reaction mixture was stirred overnight. Excess of butenone was evaporated under reduced pressure and the crude mixture was dissolved in methanol (320 ml) solution was added to an aqueous solution of potassium hydroxide (15.26 g, 272 mmol) and the mixture was heated to reflux under inert atmosphere for 30 min. The solution was cooled to room temperature, quenched with saturated ammonium chloride solution (400 ml) and the product was extracted with ethyl acetate (3×330 ml). The combined organic extracts were washed with saturated sodium chloride solution (400 ml) and dried over anhydrous sodium sulfate. The solvents were evaporated under reduced pressure and the residue chromatographed on silica gel (350 g, 0.5% triethylamine and 20%-50% ethyl acetate in petroleum ether) affording 5.49 g (22%) of the derivative 3b and 14.53 g (58%) of the derivative 3a.

Compound 3a: mp 105-108° C., $[\alpha]_D^{20}$ +149.8 (c 0.26, CHCl$_3$). $^1$H NMR (400 MHz, CDCl$_3$): δ 1.31 (3H, s, CH$_3$-19), 1.67 (1H, dtd, $J_1$=14.1, $J_2$=12.8, $J_3$=4.6, CH-7b), 1.61 (1H, ddd, $J_1$=13.8, $J_2$=10.2, $J_3$=4.6, CH-14b), 1.91-1.82 (1H, m, CH-1b), 1.85-1.94 (2H, m, CH$_2$-2), 1.93-2.00 (1H, m, CH-7a), 2.00-2.10 (1H, m, CH-1a), 2.05-2.14 (1H, m, CH-14a), 2.21 (1H, ddd, $J_1$=14.0, $J_2$=3.9, $J_3$=2.8, CH-6b), 2.30 (1H, ddd, $J_1$=16.5, $J_2$=14.1, $J_3$=5.0, CH-13b), 2.39-2.45 (1H, m, CH-13a), 2.47 (1H, tdd, $J_1$=14.0, $J_2$=4.4, $J_3$=1.9, CH-6a), 2.68 (1H, ddtd, $J_1$=12.3, $J_2$=10.1, $J_3$=5.0, $J_4$=2.2, CH-8), 3.86-4.06 (4H, m, OCH$_2$CH$_2$O), 5.36 (1H, d, J=1.3, CH-4), 5.97 (1H, d, J=2.1, CH-11). $^{13}$C NMR (101 MHz, CDCl$_3$): δ 200.34 (C, C-12), 172.37 (C, C-9), 147.21 (C, C-5), 122.65 (CH, C-11), 122.26 (CH, C-4), 105.40 (C, C-3), 64.67 (CH, OCH$_2$CH$_2$O), 64.33 (CH, OCH$_2$CH$_2$O), 41.39 (C, C-10), 36.42 (CH$_2$, C-13), 35.22 (CH, C-8), 34.11 (CH$_2$, C-7), 32.06 (CH$_2$, C-1), 31.43 (CH$_2$, C-6), 30.02 (CH$_2$, C-2), 29.51 (CH$_2$, C-14), 27.20 (CH$_2$, C-19). IR spectrum (CHCl$_3$): 2978 (CH$_3$); 2941 (CH$_2$); 2887 (CH$_3$); 2865 (CH$_2$); 1664 (C=O); 1604 (C=C); 1454, 1451 (CH$_2$); 1379 (CH$_3$); 1361, 1168, 1132 (CH$_2$); 1091, 1078, 946, 883 (kruh). MS (ESI) m/z: 275 (57%, M+H), 297 (100%, M+Na). HR-MS (ESI) m/z: For C$_{17}$H$_{23}$O$_3$ (M+H) calcd: 275.1642; found: 275.1644. For C$_{17}$H$_{22}$O$_3$ (274.2) calcd: 74.42% C, 8.08% H; found: 74.29% C, 7.98% H. Oily product 3b: $[\alpha]_D^{20}$ +217.7 (c 0.22, CHCl$_3$). $^1$H NMR (400 MHz, CDCl$_3$): δ 1.18 (3H, s, CH$_3$-19), 1.60-1.78 (2H, m, CH$_2$-7), 1.74-1.98 (2H, m, CH$_2$-6), 2.12-2.23 (1H, m, CH-2b), 2.29-2.36 (2H, m, CH$_2$-14), 2.34-2.44 (1H, m, CH-2a), 2.33-2.46 (1H, m, CH$_2$-13), 2.76 (1H, bd, $J_1$=20.1, $J_2$=1.1, CH-11b), 2.89 (1H, bd, $J_1$=20.1, $J_2$=1.6, CH-11a), 3.81-4.08 (4H, m, OCH$_2$CH$_2$O), 5.33 (1H, t, J=1.6, CH-4). $^{13}$C NMR (101 MHz, CDCl$_3$): δ 211.2 (C, C-12), 148.44 (C, C-5), 132.39 (C, C-9), 128.58 (C, C-8), 120.22 (CH, C-4), 105.62 (C, C-3), 64.67 (CH, OCH$_2$CH$_2$O), 64.17 (CH, OCH$_2$CH$_2$O), 38.50 (CH$_2$, C-11), 38.04 (CH$_2$, C-13), 37.63 (C, C-10), 32.44 (CH$_2$, C-7), 32.26 (CH$_2$, C-1), 30.17 (CH$_2$, C-6/C-14), 30.09 (CH$_2$, C-6/C-14), 29.09 (CH$_2$, C-2), 23.02 (CH$_3$, C-19). IR spectrum (CHCl$_3$): 2954, 2927 (CH$_2$); 2855 (CH$_2$); 1713 (C=O); 1674 (C=C); 1450, 1443 (CH$_2$); 1380 (CH$_3$); 1363, 1137 (CH$_2$); 1086, 946, 961 (ring). MS (ESI) m/z: 275 (100%, M+H), 297 (42%, M+Na). (ESI) m/z: For C$_{17}$H$_{23}$O$_3$ (M+H) calcd: 275.1642; found: 275.1644. For C$_{17}$H$_{22}$O$_3$ (274.4) calcd: 74.42% C, 8.08% H; found: 74.80% C, 8.82% H.

Example 3: (4bS,10aS)-7-(Ethylendioxy)-4b-methyl-1,2,4,4a,4b,5,6,7,10,10a-decahydrophenanthren-3(9H)-one (4)

To the dried (lithium wire and a catalytic amount of ferric chloride) freshly distilled liquid ammonia in a three-necked flask, cooled to −78° C. under a condenser with solid carbon dioxide was under a nitrogen atmosphere, a solution of enone 3a (9.074 g, 33.07 mmol) in tetrahydrofuran (90 ml) was added followed by ethanol (4.96 ml, 84.9 mmol). Then, under intensive stirring, lithium metal (2.66 g, 383 mmol) cut in small pieces were added portionwise. When a persistent blue coloration showed complete reduction, excess ammonia was gently evaporated. The residue was poured into saturated aqueous sodium bicarbonate (300 ml) and the product was extracted into ethyl acetate (3×100 ml). The combined organic extracts were washed with saturated aqueous sodium chloride solution, dried over anhydrous magnesium sulfate and evaporated under reduced pressure. The residue was purified by column chromatography on silica gel (150 g, 0.5% triethylamine, 30% ethyl acetate in petroleum ether) to afford 7.63 g (83%) of 4 as a colorless oil: $[\alpha]_D^{20}$ +144.7 (c 0.41, CHCl$_3$). $^1$H NMR (400 MHz, CDCl$_3$): δ 1.07 (3H, s, CH$_3$-19), 1.10-1.17 (1H, m, CH-7b), 1.25-1.34 (1H, m, CH-14b), 1.30-1.47 (1H, m, CH-9), 1.51-1.61 (1H, m, CH-1b), 1.64-1.69 (1H, m, CH-1a), 1.72-1.82 (2H, m, CH$_2$-2), 1.75-1.85 (1H, m, CH-8), 1.81-1.89 (1H, m, CH-7a), 1.97-2.04 (1H, m, CH-14a), 2.07-2.14 (1H, m, CH-6b), 2.09-2.17 (1H, m, CH-11 b), 2.24-2.32 (1H, m, CH-6a), 2.28-2.38 (2H, m, CH$_2$-13), 2.33-2.44 (1H, m, CH-11a), 3.82-4.07 (4H, m, OCH$_2$CH$_2$O), 5.31 (1H, t, J=1.2, CH-4). $^{13}$C NMR (101 MHz, CDCl$_3$): δ 211.82 (C, C-21), 149.20 (C, C-5), 121.12 (CH, C-4), 105.77 (C, C-3), 64.61 (CH, OCH$_2$CH$_2$O), 64.25 (CH, OCH$_2$CH$_2$O), 53.03 (CH, C-9), 41.09 (CH$_2$, C-11), 40.88 (CH$_2$, C-13), 37.65 (C, C-10), 35.88 (CH, C-8), 34.09 (CH$_2$, C-1), 33.59 (CH$_2$, C-7), 33.34 (CH$_2$, C-14), 31.57 (CH$_2$, C-6), 29.66 (CH$_2$, C-2), 17.55 (CH$_3$, C-19). IR spectrum (CHCl$_3$): 2969 (CH$_3$); 2938 (CH$_2$); 2888, 2864 (CH$_3$); 1711 (C=O); 1664 (C=C); 1440 (CH$_2$); 1381, 1366 (CH$_3$); 1089, 1233, 1182, 1169, 1113 (COCOC); 1009, 964, 947 (ring). MS (ESI) m/z: 277 (23%, M+H), 299 (100%, M+Na), 575 (21%, 2M+Na). HR-MS (ESI) m/z: For C$_{17}$H$_{25}$O$_3$ (M+H) calcd: 277.17982; found: 277.17993. For C$_{17}$H$_{24}$NaO$_3$ (M+Na) calcd: 299.16181. For C$_{17}$H$_{24}$O$_3$ (276.4) calcd: 73.88% C, 8.75% H; found: 74.01% C, 8.69, % H.

Example 4: (4aS,4bR,10aR)-7,7-Dimethoxy-4b-methyl-1,2,3,4,4a,4b,5,6,7,9,10,10a-dodecahydrophenanthrene (5)

To a stirred solution of the ketone 4 (1.00 g, 3.62 mmol) in methanol (25 ml) at room temperature was added tosylhydrazide (1.01 g, 5.42 mmol). After 30 minutes, sodium borohydride (2.74 g, 72.4 mmol) was added over 1 h while stirring and cooling to 25° C. The reaction mixture was stirred overnight and then poured into water (100 ml) and the product extracted with n-pentane (3×20 ml). The combined organic extracts were washed with saturated aqueous sodium chloride solution, dried over anhydrous magnesium sulfate and the solvents evaporated under reduced pressure. Chromatography on silica gel (30 g, 3% ethyl acetate in n-pentane) afforded 708 mg (75%) of the ketal 5: $[\alpha]_D^{20}$ +123.2 (c 0.57, CHCl$_3$). $^1$H NMR (400 MHz, CDCl$_3$): δ 0.83-0.94 (1H, m, CH-9), 0.87-0.97 (1H, m, CH-12b), 0.99 (3H, s, CH$_3$-19), 0.95-1.04 (1H, m, CH-14b), 1.01-1.15 (1H, m, CH-7b), 1.12-1.23 (2H, m, CH-11b, CH-13b), 1.35 (1H, qt, J$_1$=11.2, J$_2$=3.6, CH-8), 1.52-1.61 (1H, m, CH-1b), 1.61-1.70 (3H, m, CH-7a, CH-11a, CH-12a), 1.65-1.75 (1H, m, CH-14a), 1.70-1.80 (4H, m, CH-1a, CH$_2$-2, CH-13a), 2.02 (1H, ddd, J$_1$=13.7, J$_2$=4.3, J$_3$=2.4, CH-6b), 2.22 (1H, tdd, J$_1$=13.7, J$_2$=4.7, J$_3$=1.6, CH-6a), 3.85-4.04 (4H, m, OCH$_2$CH$_2$O), 5.24 (1H, d, J=1.4, CH-4). $^{13}$C NMR (101 MHz, CDCl$_3$): δ 151.86 (C, C-5), 119.58 (CH, C-4), 106.29 (c, C-3), 64.54 (CH$_2$, OCH$_2$CH$_2$O), 64.20 (CH$_2$, OCH$_2$CH$_2$O), 53.47 (CH, C-9), 37.56 (C, C-10), 37.11 (CH, C-8), 35.22 (CH$_2$, C-7), 34.68 (CH$_2$, C-12), 34.56 (CH$_2$, C-1), 32.14 (CH$_2$, C-6), 29.93 (CH$_2$, C-2), 26.80 (CH$_2$, C-13), 26.25 (CH$_2$, C-11), 25.61 (CH$_2$, C-14), 17.92 (CH$_3$, C-19). IR spectrum (CHCl$_3$): 2970 (CH$_3$); 2927 (CH$_2$); 2886, 2855 (CH$_3$); 1659 (C=C); 1451 (CH$_2$); 1451 (CH$_2$); 1380, 1364 (CH$_3$); 1233 (COCOC); 1170, 1113 (ketal); 1086, 1014, 954, 947 (C—O—C). MS (ESI) m/z: 263 (23%, M+H), 285 (13%, M+Na). HR-MS (ESI) m/z: For C$_{17}$H$_{26}$NaO$_2$ (M+Na) calcd: 285.18250; found: 285.18243. For C$_{17}$H$_{26}$O$_2$ (262.4) calcd: 77.82% C; 9.99% H; found: 77.94% C, 10.08% H.

Example 5: (4aS,4bS,8aR,10aR)-4a-Methyldodecahydrophenanthren-2(1H)-one (6)

To a solution of the ketal 5 (380 mg, 1.45 mmol) in acetone (10 ml) and water (0.5 ml) was added hydrochloric acid (35%, 3 drops) and the reaction mixture was stirred at room temperature overnight. Then, the solution was concentrated on a rotary evaporator, poured into aqueous hydrochloric acid (5%, 30 ml) and the product extracted with n-pentane (3×20 ml). The combined organic extracts were washed with saturated aqueous sodium bicarbonate solution, dried over anhydrous sodium sulfate and the solvents evaporated under reduced pressure. The residue was dissolved in ethanol (20 ml) and potassium hydroxide (45 mg) in water (120 ml) and catalyst (Pd/CaCO$_3$, 5%, 40 mg) were added. The mixture was hydrogenated under a slight positive pressure of hydrogen for 3 h. The catalyst was then filtered off, the solvent partly evaporated and the residue poured into water. The product was extracted with n-pentane (3×20 ml). The combined organic extracts were dried over anhydrous magnesium sulfate and evaporated in vacuo rotary evaporator afforded 291 mg (91%) of ketone 6, the product consisted of a mixture of isomers 5α and 5β 1:9. Ketone 6: $[\alpha]_D^{20}$ +27.8 (c 0.43, CHCl$_3$). $^1$H NMR (400 MHz, CDCl$_3$) δ 0.97 (3H, s, CH$_3$-19), 0.98-1.07 (1H, m), 1.15-1.27 (2H, m, CH-6b, CH-7b), 1.31-1.41 (1H, m, CH-1b), 1.42-1.49 (2H, m, CH-7a, CH-9), 1.65-1.72 (4H, m), 1.77-1.86 (2H, m, CH-5), 1.85-1.96 (1H, m, CH-6a), 1.98-2.06 (1H, ddd, J$_1$=14.9, J$_2$=4.7, J$_3$=2.4, CH-4b), 2.02-2.10 (1H, m, CH-2b), 2.16 (1H, dddd, J$_1$=14.7, J$_2$=4.3, J$_3$=2.5, CH-1a), 2.37 (1H, tdd, J$_1$=14.7, J$_2$=5.5, J$_3$=0.9, CH-2a), 2.72 (1H, dd, J$_1$=14.9, J$_2$=13.3, CH-4a). $^{13}$C NMR (101 MHz, CDCl$_3$): δ 213.39 (C, C-3), 44.53 (CH, C-5), 42.34 (CH$_2$, C-4), 40.36 (CH, C-9), 37.29 (CH$_2$, C-4), 36.92 (CH, C-8), 36.46 (CH$_2$, C-1), 35.10 (CH$_2$), 35.00 (C, C-10), 28.42 (CH$_2$, C-7), 27.26 (CH$_2$), 26.51 (CH$_2$), 26.45 (CH$_2$), 25.61 (CH$_2$), 22.69 (CH$_3$, C-19). IR spectrum (CHCl$_3$): 2981, 2929, 2856 (CH$_2$); 1707 (C=O); 1455, 1448 (CH$_2$); 1382 (CH$_3$). MS (EI) m/z: 149 (100%, (M−C$_4$H$_5$O), 220 (66%, M). HR-MS (ESI) m/z: For C$_{15}$H$_{24}$O (M$^+$) calcd: 220.1822; found: 220.1825. For C$_{15}$H$_{24}$O (220.4) calcd: 81.76% C; 10.98% H; found: 81.61% C; 11.03% H.

Example 6: (2R,4aS,4bS,8aR,10aR)-4a-Methyltetradecahydrophenanthren-2-ol (7a)

A mixture of ketone 6 (274 mg, 1.24 mmol), dichloromethane (5 ml) and dry methanol (5 ml) was cooled to −78° C. Then, dried cerium chloride (337 mg, 1.37 mmol) and sodium borohydride (52 mg, 1.37 mmol) were added while stirring. After 15 min stirring at −78° C. the reaction mixture was slowly warmed to room temperature and quenched with dilute hydrochloric acid (5%, 25 ml). The product was extracted with dichloromethane (3×10 ml), the combined organic extracts were washed with saturated aqueous sodium bicarbonate solution and dried over anhydrous magnesium sulfate. Evaporation of the solvents and chromatography of the residue on silica gel column (10 g, 10% ether in n-pentane) yielded 186.6 mg (68%) of 3α, 5β-7a alcohol and 5.5 mg (2%), 3β,5β-alcohol 7b. Compound 7a: [α]$_D^{20}$ +21.8 (c 0.29, CHCl$_3$). $^1$H NMR (400 MHz, CDCl$_3$): δ 0.87 (3H, s, CH$_3$-19), 0.84-0.96 (1H, m, CH-7b), 0.90-1.04 (2H, m, CH-1b, CH-14b), 1.14-1.24 (2H, m, CH-13b, CH-11b), 1.15-1.29 (2H, m, CH-6b, CH-12b), 1.24-1.33 (1H, m, CH-8), 1.32-1.39 (1H, m, CH-12a), 1.35-1.42 (1H, m, CH-5), 1.31-1.44 (1H, m, CH-2b), 1.39-1.46 (1H, m, CH-9), 1.50 (1H, dddd, J$_1$=12.6, J$_2$=4.7, J$_3$=3.8, J$_4$=2.4, CH-4b), 1.58-1.66 (2H, m, CH-1a, CH-7a), 1.60-1.70 (1H, m, CH-11a), 1.62-1.70 (1H, m, CH-2a), 1.71-1.80 (1H, m, CH-13a), 1.72-1.84 (1H, m, CH-4a), 1.77-1.87 (1H, m, CH-14a), 1.84-1.91 (1H, m, CH-6a), 2.18 (1H, bs, OH), 3.62 (1H, tt, J$_1$=11.1, J$_2$=4.7, CH-3). $^{13}$C NMR (101 MHz, CDCl$_3$): δ 71.73 (CH, C-3), 42.22 (CH, C-5), 40.00 (CH, C-9), 37.25 (CH, C-8), 36.21 (CH$_2$, C-4), 35.17 (CH$_2$, C-1), 34.64 (CH$_2$, C-14), 34.53 (C, C-10), 30.54 (CH$_2$, C-2), 29.09 (CH$_2$, C-12), 27.28 (CH$_2$, C-13), 27.02 (CH$_2$, C-6), 26.53 (CH$_2$, C-11), 25.34 (CH$_2$, C-7), 23.34 (CH$_3$, C-19). IR spectrum (CHCl$_3$): 3609, 3452 (OH); 2977 (CH$_2$); 2927 (CH$_2$); 2858 (CH$_2$); 1450 (CH$_2$); 1380, 1364 (CH$_3$); 1035, 1015 (C—OH). MS (ESI) m/z: 245 (100%, M+Na). HR-MS (ESI) m/z: For C$_{15}$H$_{26}$NaO (M+Na) calcd: 245.1876; found: 245.1875. For C$_{15}$H$_{26}$O (222.4) calcd: 81.07% C, 11.79% H; found: 81.11% C, 11.98% H.

Example 7: Pyridinium (2R,4aS,4bS,8aR,10aR)-4a-methyltetradecahydrophenanthren-2-yl 2-Sulfate (8)

Compound 8 was prepared according to General Procedure I—Preparation of C-3 Sulfate from compound 7a (166 mg, 747 μmol) affording sulfate 8 (248 mg, 87%): [α]$_D^{20}$ +22.6 (c 0.23, CHCl$_3$). $^1$H NMR (400 MHz, CDCl$_3$): δ 0.86 (3H, s, CH$_3$-19), 0.83-0.93 (1H, m, CH-11b), 0.90-1.00 (1H, m), 0.95-1.04 (1H, m, CH-1b), 1.22-1.35 (1H, m, CH-8), 1.12-1.40 (5H, m, CH$_2$-6), 1.38-1.48 (2H, m, CH-5, CH-9), 1.54-1.63 (1H, m, CH-11a), 1.50-1.64 (1H, m, CH-2b), 1.56-1.66 (2H, m), 1.71-1.78 (1H, m), 1.79-1.88 (3H, m, CH-1a, CH-4b), 1.90-2.03 (2H, m, CH-4a, CH-2a), 4.47 (1H, tt, J$_1$=11.3, J$_2$=4.9, CH-3), 7.99-8.03 (2H, m, CH-3'), 8.48 (1H, tt, J$_1$=7.9, J$_2$=1.6, CH-4'), 8.99-8.01 (2H, m, CH-2'). $^{13}$C NMR (101 MHz, CDCl$_3$): δ 145.60 (CH, C-4'), 142.37 (CH, C-2'), 127.12 (CH, C-3'), 79.67 (CH, C-3), 42.34 (CH, CH-5), 40.05 (CH, C-9), 37.29 (CH, C-8), 35.29 (CH$_2$), 34.67 (CH$_2$, C-1), 34.52 (C, C-10), 33.26 (CH$_2$, C-4), 29.09 (CH$_2$, C-6), 27.89 (CH$_2$, C-2), 27.38 (CH$_2$), 26.93 (CH$_2$), 26.61 (CH$_2$), 25.41 (CH$_2$, C-11), 23.32 (CH$_3$, C-19). IR spectrum (CHCl$_3$): 2927 (CH$_2$); 2856 (CH$_2$); 2450-2750 (NH$^+$); 2135 (NH$^+$); 1490 (ring); 1450 (CH$_2$); 1380 (CH$_3$); 1255, 1171, (SO$_3$); 1047 (SO$_3$); 970, 953, (COS); 828 (COS); 682 (=CH); 624 (SO$_3$). MS (ESI) m/z: 301 (100%, M-C$_5$H$_6$N$^+$). HR-MS (ESI) m/z: For C$_{15}$H$_{25}$O$_4$S (M-C$_5$H$_6$N$^+$) calcd: 301.1479; found: 301.1479. For C$_{20}$H$_{31}$NO$_4$S (381.5) calcd: 62.96% C, 8.19% H; 3.67% N; found: 60.82; % C, 8.09% H; 3.61% N.

Example 8: 4-(((2R,4aS,4bS,8aR,10aR)-4a-Methyltetradecahydrophenanthren-2-yl)oxy)-4-oxobutanoic Acid (9)

Compound 9 was prepared according to General Procedure II—Preparation of C-3 Hemisuccinate from compound 7a (47 mg, 0.21 mmol). Chromatography on silica gel (4-10% acetone in petroleum ether) afforded 52 mg (76%) of compound 9: mp 131-133° C. (acetone/n-heptane), [α]$_D^{20}$ +45.5 (c 0.20, CHCl$_3$). $^1$H NMR (400 MHz, CDCl$_3$): δ 0.87 (3H, s, H-19), 2.51-2.76 (4H, m, H-2' and H-4'), 4.76 (1H, tt, J$_1$=11.3, J$_2$=4.7, H-3). $^{13}$C NMR (101 MHz, CDCl$_3$): δ 177.10, 171.83, 75.31, 42.31, 40.26, 37.47, 35.38, 34.84, 34.55, 32.30, 29.45, 29.24, 29.04, 27.49, 27.10, 26.89, 26.75, 25.59, 23.53. IR spectrum (CHCl$_3$): 3517 (OH, monomer); 1727, 1717 (C=O); 1232, 1176, 1170 (COC). MS (ESI) m/z: 345.2 (100%, M+Na). HR-MS (ESI) m/z: For C$_{19}$H$_{30}$O$_4$Na (M+Na) calcd: 345.2036; found: 345.2036.

Example 9: Methyl (1S,2S,4aS,4bS,7R,8aR,10aR)-7-acetoxy-2,4b-dimethyl-1-(2-oxoethyl)tetradecahydrophenanthren-2-carboxylate (11)

A stirred solution of enol acetate 10 (5.0 g, 13.35 mmol) in dichloromethane (150 ml) and glacial acetic acid (13 ml) was ozonized at −78° C. until a blue color of the solution persisted. Then, to the reaction mixture was gradually added in small portions dimethylsulfide (2 ml, 27.37 mmol), glacial acetic acid (130 ml) and water (28 ml). The resulting solution was stirred 18 hours at room temperature. The product was extracted into dichloromethane, the combined organic extracts were washed with water, dried over anhydrous magnesium sulfate and the solvents were evaporated under reduced pressure on a rotary evaporator. The residue was dissolved in ether, the solution cooled to 0° C. and addition of an ethereal solution of diazomethane was added and free carboxylic group esterified. Chromatography on silica gel (10% ethyl acetate in petroleum ether) afforded 4.45 g (88%) non-crystallising methyl ester 11: [α]$_D^{20}$ −9.6 (c 0.24, MeOH). $^1$H NMR (400 MHz, CD$_3$OD): δ 0.89 (3H, s, H-18), 1.11 (3H, s, H-19), 2.02 (3H, s, OAc), 3.65 (3H, s, OCH$_3$), 4.66-4.76 (1H, m, H-3), 9.67 (1H, s, CHO). $^{13}$C NMR (101 MHz, CD$_3$OD): δ 201.97, 178.37, 170.76, 74.08, 52.12, 47.59, 46.71, 41.46, 39.83, 37.80, 36.78, 34.88, 34.77, 32.10, 26.96, 26.72, 26.31, 23.33, 21.55, 19.83, 15.56. IR spectrum (CHCl$_3$): 2828 (CHO); 1721 (C=O); 1435, 1385, 1364 (CH$_3$); 1253 (COO). MS (ESI) m/z: 401.3 (100%, M+Na). HR-MS (ESI) m/z: For C$_{22}$H$_{34}$O$_5$Na (M+Na) calcd: 401.2299; found: 401.2297.

Example 10: Methyl (1S,2S,4aS,4bS,7R,8aR,10aS)-7-acetoxy-1,2,4b-trimethyltetradecahydrophenanthren-2-carboxylate (12)

Compound 12 was prepared according to General Procedure VI—Wilkinson Decarbonylation from compound 11

(1.33 g, 3.65 mmol). Chromatography on silica gel (10% acetone in petroleum ether) afforded 1.31 g (69%) of 12: $^1$H NMR (400 MHz, CD$_3$OD): δ 0.72 (311, d, J=6.7, H-15), 0.89 (31-1, s, H-18), 1.06 (3H, s, H-19), 2.03 (3H, s, OAc), 3.66 (3H, s, OCH$_3$), 4.66-4.76 (1H, m, H-3). $^{13}$C NMR (101 MHz, CD$_3$OD): δ 179.21, 170.77, 74.35, 51.85, 47.76, 42.36, 41.56, 39.66, 37.74, 37.05, 34.86 (2×C), 32.19, 27.07, 26.75, 25.52, 23.36, 21.58, 20.09, 15.34, 14.64. IR spectrum (CHCl$_3$): 1721 (C=O); 1467, 1386, 1024 (OAc); 1364, 1160 (COOCH$_3$). MS (ESI) m/z: 373.2 (100%, M+Na). HR-MS (ESI) m/z: For C$_{21}$H$_{34}$O$_4$Na (M+Na) calcd: 373.2349; found: 373.2348.

Example 11: (2R,4aS,4bS,7S,8S,8aS,10aR)-7-(Hydroxymethyl)-4a,7,8-trimethyltetradecahydrophenanthren-2-ol (13)

A mixture of ester 12 (1.00 g, 2.86 mmol) and lithium aluminum hydride (2.86 mg, 8.58 mmol) in tetrahydrofuran (30 ml) was heated to reflux under an inert atmosphere of argon for 2 h. The excess of reagent was carefully quenched with saturated aqueous sodium sulfate; inorganic materials were removed by filtration and washed with ethyl acetate. The filtrate was washed with aqueous hydrochloric acid (5%), water, saturated aqueous sodium bicarbonate solution and dried over anhydrous sodium sulfate. The solvents were evaporated under reduced pressure. The attempts to crystallize the residue 585 mg (73%) 13 failed: $[\alpha]_D^{20}$ -3.4 (c 0.33, CHCl$_3$). $^1$H NMR (400 MHz, CD$_3$OD): δ 0.69 (3H, s, H-18), 0.78 (3H, d, J, 6.3, H-15), 0.89 (3H, s, H-19), 2.03 (3H, s, OAc), 3.35 (2H, dd, J$_1$=92.2, J$_2$=10.9, 3.56-3.66 (1H, m, H-3). $^{13}$C NMR (101 MHz, CD$_3$OD): δ 72.01, 71.74, 41.80, 40.57, 39.96, 38.21, 38.15, 36.46, 35.80, 35.17, 34.98, 30.79, 27.46, 26.13, 23.53, 20.49, 15.69, 12.61. IR spectrum (CHCl$_3$): 3628, 3616 (OH); 2935, 2866 (CH$_2$); 1380 (CH$_3$); 1035 (C—OH). MS (ESI) in/z: 303.3 (100%, M+Na). HR-MS (ESI) m/z: For C$_{18}$H$_{32}$O$_2$Na (M+Na) calcd: 303.2295; found: 303.2295.

Example 12: (4aS,4bS,7S,8S,8aS,10aR)-7-(Hydroxymethyl)-4a,7,8-trimethyldodecahydrophenanthren-2(1H)-one (14)

Aqueous sodium hypochlorite solution (4.5%, 7.7 ml) was added to a solution of diol 13 (585 mg, 2.09 mmol) in acetic acid (18 ml). The reaction mixture was stirred at room temperature for 1 h, then propan-2-ol (11 ml) was added and the mixture was stirred for 30 min. The reaction was quenched by addition of water (20 ml), the product was extracted with chloroform (3×50 ml), and the combined organic extracts were washed with saturated aqueous sodium chloride solution and dried over anhydrous sodium sulfate. The solvents were evaporated and the residue flash chromatographed on silica gel (4-10% acetone in petroleum ether). Were obtained 412 mg (71%) of non-crystallising ketone 14: $[\alpha]_D^{20}$ -2.7 (c 0.29, CHCl$_3$). $^1$H NMR (400 MHz, CDCl$_3$): δ 0.73 (3H, s, H-18), 0.82 (3H, d, J=6.3, H-15), 0.99 (3H, s, H-19), 3.38 (2H, dd, J$_1$=101.4, J$_2$=10.9, H-17). $^{13}$C NMR (101 MHz, CDCl$_3$): δ 213.44, 71.47, 44.04, 42.38, 40.44, 40.22, 38.18, 37.87, 37.40, 36.89, 35.68, 35.34, 26.93, 25.51, 22.83, 20.80, 15.72, 12.56. IR spectrum (CHCl$_3$): 3630 (OH); 2935, 2860 (CH$_2$); 1708 (C=O); 1383 (methyl); 1032 (CCO). MS (ESI) m/z: 301.2 (100%, M+Na). HR-MS (ESI) m/z: For C$_{18}$H$_{30}$O$_2$Na (M+Na) calcd: 301.2138; found 301.2139.

Example 13: ((4aS,4bS,7S,8S,8aS,10aR)-4a,7,8-Trimethyldodecahydro-1H-spiro[phenanthren-2,2'-[1,3]dioxolan]-7-yl)methanol (15)

A mixture of ketone 14 (550 mg, 1.98 mmol), triethyl orthoformate (2.3 ml, 13.85 mmol), ethylene glycol (2.2 ml, 39 mmol) and p-toluenesulfonic acid (60 mg, 0.32 mmol) in benzene (10 ml) was stirred at room temperature for 1 h. The reaction mixture was then allowed to stand 17 h at 50° C. After cooling, the mixture was poured into saturated aqueous sodium chloride solution, the product was extracted with ethyl acetate, and the combined organic extracts were washed with saturated aqueous sodium chloride solution and dried over anhydrous magnesium sulfate. The solvents were evaporated and the residue chromatographed on silica gel (1% triethylamine and 10% ethyl acetate in petroleum ether) yielding 542 mg (85%) of oily ketal 15: $[\alpha]_D^{20}$ -2.7 (c 0.26, CHCl$_3$). $^1$H NMR (400 MHz, CDCl$_3$): δ 0.70 (3H, s, H-18), 0.78 (3H, d, J=6.3, H-15), 0.92 (3H, s, H-19), 335 (2H, dd, J$_1$=89.0, J$_2$=10.9, H-17), 3.93 (4H, OCH$_2$CH$_2$O). $^{13}$C NMR (101 MHz, CDCl$_3$): δ 110.20, 71.76, 64.37, 64.22, 40.60, 40.59, 39.28, 38.15, 38.00, 35.78, 35.66, 34.99, 34.00, 30.32, 27.02, 25.90, 23.27, 20.69, 15.69, 12.58. IR spectrum (CHCl$_3$): 3630 (OH); 2976, 2881, 1381 (methyl); 2928, 1471 (CH$_2$); 1471, 1094, 947 (ketal); 1030 (COH). MS (CI) m/z: 321.2 (52%, M–H), 323.2 (54%, M+H). HR-MS (CI) m/z: For C$_{20}$H$_{33}$O$_3$ (M–H) calcd: 321.2433; found: 321.2430.

Example 14: (4aS,4bS,7S,8aS,10aR)-7-(Methoxymethyl)-4a,7,8-trimethyldodecahydrophenanthren-2(1H)-one (16)

Sodium hydride (60% suspension in oil, 346 mg) was added to a solution of the ketal 15 (430 mg, 1.33 mmol) in dried tetrahydrofuran (30 ml) and the mixture was stirred under an inert atmosphere of argon for 1 h and heated at 90° C. Methyl iodide (0.7 ml, 11.4 mmol) was added and the mixture was stirred and heated to 90° C. under an inert atmosphere of argon for 5 h. After cooling, the product was extracted with ethyl acetate; the combined organic extracts were washed with saturated aqueous sodium chloride solution, dried over anhydrous magnesium sulfate and the solvents evaporated under reduced pressure. The residue was dissolved in acetone (10 ml), diluted hydrochloric acid (5%, 150 ml) was added and the mixture was stirred at room temperature for 1 h. The reaction was quenched by addition of saturated aqueous sodium bicarbonate (10 ml), the product was extracted with ethyl acetate, and the combined organic extracts were washed with brine and dried with magnesium sulfate. Evaporation of the solvent afforded 322 mg (83%) of non-crystallising keto derivative 16: $[\alpha]_D^{20}$ -3.5 (c 0.37, CHCl$_3$/MeOH, 2: 0.14). $^1$H NMR (400 MHz, CDCl$_3$): δ 0.72 (3H, s, H-19), 0.80 (3H, d, J=6.3, H-15), 0.98 (3H, s, H-18), 3.09 (2H, dd, J$_1$=129.6, J$_2$=9.1, H-17), 3.32 (3H, OCH$_3$). $^{13}$C NMR (101 MHz, CDCl$_3$): δ 213.49, 81.78, 59.45, 44.12, 42.39, 40.75, 40.11, 37.76, 37.40, 36.94, 36.34, 35.32, 29.85, 26.94, 25.44, 22.80, 20.85, 15.99, 12.59. IR spectrum (CHCl$_3$): 2928 (CH$_2$); 1707 (C=O); 1382 (methyl); 1101 (COC). MS (CI) m/z: 293.2 (72%, M+H). HR-MS (CI) m/z: For C$_{19}$H$_{33}$O$_2$ (M+H) calcd: 293.2481; found: 293.2477.

Example 15: (2R,4aS,4bS,7S,8aS,10aR)-7-(Methoxymethyl)-4a,7,8-trimethyltetradecahydrophenanthren-2-ol (17)

A solution of ketone 16 (400 mg, 1.37 mmol) in methanol (20 ml) was cooled to 0° C. and sodium borohydride (57 mg, 1.51 mmol) was added while stirring. The mixture was stirred for 1 h at 0° C., then was warmed to room temperature and quenched with dilute hydrochloric acid (5%, 15 ml). The product was extracted with chloroform (3×20 ml), the combined organic extracts were washed with saturated aqueous sodium bicarbonate solution and dried over anhydrous magnesium sulfate. Evaporation of the solvents and chromatography of the residue (7% acetone in petroleum ether) gave 323 mg (80%) of hydroxy derivative 17: mp 107-108° C. (acetone/n-heptane), $[\alpha]_D^{20}$ −9.2 (c 0.37, CHCl$_3$). $^1$H NMR (400 MHz, CDCl$_3$): 0.69 (3H, s, H-19), 0.77 (3H, d, J=6.4, H-15), 0.88 (3H, s, H-18), 3.07 (2H, dd, J$_1$=11.3, J$_2$=9.1, H-17), 3.32 (3H, s, OCH$_3$), 3.57-3.66 (1H, m, H-3). $^{13}$C NMR (101 MHz, CDCl$_3$): δ 82.11, 72.04, 59.45, 41.85, 40.93, 39.88, 38.11, 37.71, 36.48, 36.46, 35.20, 34.96, 30.78, 27.48, 26.06, 23.52, 20.54, 15.96, 12.68. IR spectrum (CHCl$_3$): 3609 (OH); 2977 (CH$_3$); 1100 (COC). MS (ESI) m/z: 317.2 (100%, M+Na). (ESI) m/z: For C$_{19}$H$_{34}$O$_2$Na (M+Na) calcd: 317.2451; found: 317.2451.

Example 16: Pyridinium (2R,4aS,4bS,7S,8S,8aS, 10aR)-7-(methoxymethyl)-4a,7,8-trimethyltetradecahydrophenanthren-2-yl 2-sulfate (18)

Compound 18 was prepared according to General Procedure I—Preparation of C-3 Sulfate from compound 17 (78 mg, 0.26 mmol) affording sulfate 18 (40 mg, 33%): $[\alpha]_D^{20}$ +4.0 (c 0.30, CHCl$_3$/MeOH, 1.849:0.341). $^1$H NMR (400 MHz, CDCl$_3$): δ 0.68 (3H, s, H-19), 0.75 (3H, d, J=6.1, H-15), 0.86 (3H, s, H-18), 3.06 (2H, dd, J$_1$=112.6, J$_2$=9.1, H-17), 3.31 (3H, s, OCH$_3$), 4.46 (1H, tt, J$_1$=10.9, J$_2$=4.9, H-3), 8.01 (2H, m, H-2' and H-4', pyridinium), 8.49 (1H, t, J=8.6, H-3', pyridinium), 8.92-9.05 (2H, m, H-1' and H-5', pyridinium). $^{13}$C NMR (101 MHz, CDCl$_3$) δ 145.84 (C-1', C-5'), 142.41 (C-3'), 127.30 (C-2', C-4'), 82.13, 79.89, 59.43, 41.84, 41.00, 39.82, 38.04, 37.70, 36.50, 35.10, 34.84, 33.25, 27.91, 27.31, 26.01, 23.43, 20.50, 15.95, 12.66. IR spectrum (CHCl$_3$): 2976, 2933 (CH$_2$OCH$_3$); 1263, 1255, 1183, 1044, 954 (SO$_3$). MS (ESI) in/z: 373.2 (100%, M−H-pyridine). HR-MS (ESI) m/z: For C$_{19}$H$_{33}$O$_5$S (M−H-pyridine) calcd: 373.2054; found: 373.2054.

Example 17: 4-(((2R,4aS,4bS,7S,8aS,10aR)-7-(Methoxymethyl)-42,7,8-trimethyltetradecahydrophenanthren-2-yl)oxy)-4-oxobutanoic Acid (19)

Compound 19 was prepared according to General Procedure II—preparation of C-3 Hemisuccinate from compound 17 (70 mg, 0.23 mmol). Chromatography on silica gel (10% acetone in petroleum ether) afforded 78 mg (83%) of the derivative 19: $[\alpha]_D^{20}$ +6.5 (c 0.27, CHCl$_3$). $^1$H NMR (400 MHz, CDCl$_3$): δ 0.68 (3H, s, H-19), 0.77 (3H, d, J=6.1, H-15), 0.88 (3H, s, H-18), 2.51-2.76 (4H, m, OCCH$_2$CH$_2$CO), 3.08 (2H, dd, J$_1$=126.8, J$_2$=9.0, H-17), 3.33 (3H, s, OCH$_3$), 4.75 (1H, tt, J$_1$=11.3, J$_2$=4.8, 11-3). $^{13}$C NMR (101 MHz, CDCl$_3$): δ 177.20, 171.85, 81.97, 75.13, 59.44, 41.63, 40.80, 39.85, 38.03, 37.71, 36.45, 34.97, 34.85, 32.06, 29.45, 29.05, 27.29, 26.67, 25.97, 23.45, 20.55, 16.00, 12.63. IR spectrum (CHCl$_3$): 2935 (CH$_2$OCH$_3$); 1717 (C=O, COOH); 1100 (COC). MS (ESI) m/z; 393.3 (100%, M−H). HR-MS (ESI) m/z: For C$_{23}$H$_{37}$O$_5$ (M−H) calcd: 393.2647; found: 393.2643. For C$_{23}$H$_{38}$O$_5$ (394.3) calcd: 70.02% C, 9.71% H; found: 69.76% C, 9.68% H.

Example 18: Methyl (1S,2S,4aS,4bS,7R,8aR,10aS)-7-hydroxy-1,2,4b-trimethyltetradecahydro-phenanthren-2-carboxylate (20)

To a solution of 12 (100 mg, 0.29 mmol) in methanol (5 ml) was added potassium hydroxide (60 mg, 1.07 mmol) in methanol (2 ml) and the mixture was stirred at ambient for 18 h. Then, it was poured into water; the product was extracted with ethyl acetate. The combined organics were washed with dilute hydrochloric acid (5%), water, saturated sodium bicarbonate solution and dried over anhydrous sodium sulfate. Evaporation of solvents under reduced pressure gave a residue of 20 (83 mg, 94%) which crystallized from ethyl acetate/n-heptane: mp 144-146° C. (ethyl-acetate/n-heptane), $[\alpha]_D^{20}$ +6.2 (c 0.33, CHCl$_3$). $^1$H NMR (400 MHz, CD$_3$OD): δ 0.73 (3H, d, J=6.7, H-15), 0.89 (3H, s, H-19), 1.06 (3H, s, H-18), 3.67 (3H, s, OCH$_3$), 3.58-3.68 (1H, H-3). $^{13}$C NMR (101 MHz, CD$_3$OD): δ 179.26, 71.92, 51.87, 47.78, 42.32, 41.78, 39.69, 37.81, 37.06, 36.43, 35.18, 34.86, 30.73, 27.25, 25.62, 23.41, 20.10, 15.38, 14.66. IR spectrum (CHCl$_3$): 3609, 1054, 1033 (OH); 3020, 2942 (CH$_3$); 1720 (C=O); 1243 (COC). MS (ESI) m/z: 331.3 (100%, M+Na). HR-MS (ESI) m/z: For C$_{19}$H$_{32}$O$_3$Na (M+Na) calcd: 331.2244, found: 331.2243.

Example 19: 4-(((2R,4aS,7S,8S,10aR)-7-(Methoxykarbonyl)-4a,7,8-trimethyltetradecahydrophenanthren-2-yl)oxy)-4-oxobutanoic Acid (21)

Compound 21 was prepared according to General Procedure II—Preparation of C-3 Hemisuccinate from compound 20 (100 mg, 0.32 mmol). Chromatography on silica gel (10% acetone in petroleum ether) gave compound 21 (68 mg, 51%) as a white solid: mp 145-147° C. (ethyl acetate/n-heptane), $[\alpha]_D^{20}$ +21.5 (c 0.21, CHCl$_3$). $^1$H NMR (400 MHz, CD$_3$OD): δ 0.73 (3H, d, J=6.7, H-15), 0.90 (3H, s, H-19), 1.06 (3H, s, H-18), 2.55-2.72 (4H, m, OCCH$_2$CH$_2$CO), 3.67 (3H, s, OCH$_3$), 4.70-4.81 (1H, m, H-3). $^{13}$C NMR (101 MHz, CD$_3$OD): δ 17930, 171.91, 74.93, 51.88, 47.77, 42.33, 41.58, 39.67, 37.74, 37.03, 34.87, 34.83, 32.11, 29.83, 29.47, 29.03, 27.06, 26.70, 25.51, 23.34, 20.09, 15.34, 14.63. IR spectrum (CHCl$_3$): 3020, 1361 (CH$_3$); 2950 (CH$_2$); 1724, 1718 (C=O); 1243, 1166 (COC). MS (ESI) m/z: 431.2 (100%, M+Na). HR-MS (ESI) m/z: For C$_{23}$H$_{36}$O$_6$Na (M+Na) calcd: 431.2404; found: 431.2403.

Example 20: Pyridinium (2R,4aS,7S,8S,10aR)-7-(methoxycarbonyl)-4a,7,8-trimethyltetra-decahydrophenanthren-2-yl 2-sulfate (22)

Compound 22 was prepared according to General Procedure I—Preparation of C-3 Sulfate from compound 20 (104 mg, 0.34 mmol) affording sulfate 22 (55 mg, 35%): mp 145-147° C. (ethyl-acetate/n-heptane), $[\alpha]_D^{20}$ +10.9 (c 0.40, CHCl$_3$). $^1$H NMR (400 MHz, CD$_3$OD): δ 0.71 (3H, d, J=6.6, H-15), 0.88 (3H, s, H-19), 1.05 (3H, s, H-18), 3.67 (3H, s, OCH$_3$), 4.47 (1H, tt, J$_1$=10.9, J$_2$=5, H-3), 8.02 (2H, m, H-2' and H-4', pyridinium), 8.49 (1H, t, J=7.8, H-3', pyridinium), 8.96-9.02 (2H, m, H-1" a H-5', pyridinium). $^{13}$C NMR (101 MHz, CD$_3$OD): δ 179.30, 145.89 (C-1', C-5'), 142.41, 127.33 (C-2', C-4'), 79.53, 51.85, 47.75, 42.37, 41.77, 39.62, 37.72, 37.09, 35.10, 34.73, 33.27, 27.91, 27.07, 25.55, 23.32, 20.06, 15.36, 14.64. IR spectrum (CHCl$_3$): 3140, 3100, 1490 (pyridinium); 1720 (C=O); 1264, 1183, 1175, 1044, 954 (SO$_3$); 1245, 1192 (C—O). MS (ESI) m/z: 387.2 (100%, M-pyridine). HR-MS (ESI) m/z: For C$_{19}$H$_{31}$O$_6$S (M-pyridine) calcd: 387.1847, found: 387.1844.

Example 21: 2S,4aS,4bS,7S,8aR,10aR)-7-hydroxy-2,4b-dimethyl-1-(((E)-3-oxoindolin-2-yliden)-methyl)tetradecahydrophenanthren-2-carboxylic Acid (24)

A solution of o-nitrobenzaldehyde (2.75 g) in methanol (25 ml) was added to a mixture of 3beta-hydroxy-5betaandrostan-17-one (23) (5.0 g, 17.22 mmol) in methanolic potassium hydroxide solution (4%, 125 ml). The reaction mixture was stirred at room temperature for 18 h and methanol solution of potassium hydroxide (0.5 g in 1 ml) and o-nitrobenzaldehyde (275 mg in 2.5 ml) were added. After 20 h, the reaction mixture was concentrated under reduced pressure to ⅓ of volume, diluted with water (20 m), filtered over active carbon and the filtrate was acidified with dilute hydrochloric acid (5%). The yellow precipitated solids of 24 were isolated, washed with water and dried (6.1 g, 84%): mp 242-245° C. (methanol/water), $[\alpha]_D^{20}$ −182.2 (c 0.29, $CH_3OH$). $^1H$ NMR (400 MHz, $CD_3OD$): δ 0.98 (3H, s, H-18), 1.24 (3H, s, H-19), 2.86 (1H, dd, $J_1$=11.4, $J_2$=10, H-14), 4.02-4.07 (1H, m, H-3), 5.81 (1H, d, J=11.6, H-15), 6.79 (1H, t, J=7.7), 6.93 (1H, d, J=8.2), 7.41 (1H, t, J=7.7), 7.52 (1H, d, J=7.7). $^{13}C$ NMR (101 MHz, $CD_3OD$): δ 187.72, 18139, 155.99, 140.14, 137.88, 125.48, 121.86, 119.96, 117.67, 112.83, 67.68, 48.85, 48.09, 39.98, 38.12, 37.64, 37.60, 36.53, 34.23, 30.63, 28.55, 27.74, 27.64, 24.26, 21.01, 16.09. IR spectrum (KBr): 3445, 3343 (OH, NH); 2976, 1383 (methyl); 2613 (OH, dimer); 1708 (C=O, dimer); 1693 (C=O, indolone); 1639 (C=C); 1613, 1486, 1468, 1448 (ring, indolone); 1003 (C—OH). MS (ESI) m/z: 446.3 (100%, M+Na), 424.3 (45%, M+H). HR-MS (ESI) m/z: For $C_{26}H_{33}O_4NNa$ (M+Na) calcd; 446.2302; found: 446.2301.

Example 22: Methyl (2S,4aS,4bS,7S,8aR,10aR)-7-hydroxy-2,4b-dimethyl-1-(((E)-3-oxoindolin-2-yliden)methyl)-tetradecahydrophenanthren-2-carboxylate (25)

A freshly prepared ethereal solution of diazomethane was added while stirring to a cooled solution of compound 24 (0° C., 5 g, 11.80 mmol) in ether. After completion of reaction (TLC), excess of diazomethane was evaporated affording 5.1 g (99%) of non-crystallising methyl ester (25): $[\alpha]_D^{20}$ −208.1 (c 0.26, $CHCl_3$). $^1H$ NMR (400 MHz, $CDCl_3$): δ 0.97 (3H, s, H-18), 1.24 (3H, s, H-19), 2.72 (1H, t, J=10.7, H-14), 3.56 (1H, s, $OCH_3$), 4.12-4.14 (1H, m, H-3), 5.77 (1H, d, J=11.1, H-15), 6.87 (1H, t, J=7.7), 6.93 (1H, d, J, 8.2), 7.42 (1H, t, J=7.7), 7.66 (1H, d, J=7.7). $^{13}C$ NMR (101 MHz, $CDCl_3$): δ 185.93, 179.78, 154.04, 138.80, 136.25, 125.06, 122.45, 119.89, 116.52, 112.22, 67.03, 52.44, 47.65, 47.54, 38.67, 37.81, 36.59, 36.33, 35.60, 33.58, 29.64, 28.00, 26.94, 26.51, 23.85, 19.91, 16.00. IR spectrum ($CHCl_3$): 3616 (OH); 2979, 1435, 1384 1716 (C=O); 1701 (C=O, indolone); 1644 (C=C). MS (ESI) m/z: 460.4 (100%, M+Na), 438.4 (52%, M+H). HR-MS (ESI) m/z: For $C_{27}H_{36}O_4N$ (M+H) calcd: 438.2639; found: 438.2639.

Example 23: Methyl (2S,4aS,4bS,7S,8aR,10aR)-7-acetoxy-2,4b-dimethyl-1-(((E)-3-oxoindolin-2-yliden)methyl)-tetradecahydrophenanthren-2-carboxylate (26)

To a cold (0° C.) mixture of methyl ester 25 (7.2 g, 16.45 mmol) and 4-(N,N-dimethylamino)pyridine (200 mg, 1.64 mmol) in pyridine (50 ml) was added acetic anhydride (46 ml). The reaction mixture was warmed to room temperature and after 2 h; the reaction was quenched by adding a small amount of water. The reaction mixture was poured into dilute hydrochloric acid (5%, 150 ml), the product was extracted with ethyl acetate (3×80 ml) and the combined organic phases were washed with water (2×100 ml), saturated sodium bicarbonate, and saturated brine and dried with anhydrous magnesium sulfate. The solvents were evaporated under reduced pressure yielding 7.0 g (89%) of non-crystallizing compound 26: $[\alpha]_D^{20}$ −221.1 (c 0.274, $CHCl_3$). $^1H$ NMR (400 MHz, $CDCl_3$): δ 0.98 (3H, s, H-18), 1.24 (3H, s, H-19), 2.04 (3H, s, OAc), 2.73 (1H, t, J=10.7, H-14), 3.56 (3H, s, $OCH_3$), 5.05-5.11 (1H, m, H-3), 5.76 (1H, d, J=11.2, H-15), 6.87 (1H, t, J=7.7), 6.93 (1H, d, J=8.2), 7.42 (1H, t, J=7.7), 7.65 (1H, d, J=7.7). $^{13}C$ NMR (101 MHz, $CDCl_3$): δ 185.92, 179.66, 170.81, 154.04, 138.83, 136.28, 125.04, 122.43, 119.90, 116.31, 112.23, 70.55, 52.44, 47.61, 38.82, 47.46, 37.74, 37.14, 36.60, 35.35, 30.63, 30.46, 26.82, 26.36, 25.18, 23.80, 21.62, 19.90, 16.00. IR spectrum ($CHCl_3$): 2979, 1385, 1379 (methyl); 1727 (C=O, OAc); 1717 (C=O, COOMe); 1702 (C=O, indolone); 1645 (C=C); 1615, 1485, 1470, 1448 (ring, indolone). MS (ESI) m/z: 502.4 (100%, M+Na), 480.4 (30%, M+H). HR-MS (ESI) m/z: For $C_{29}H_{38}O_5$ (M+H) calcd: 480.2745; found: 480.2746.

Example 24: Methyl (2S,4aS,4bS,7S,8aR,10aR)-7-acetoxy-1-formyl-2,4b-dimethyltetradecahydrophenanthren-2-carbaoxylate (27)

Compound 27 was prepared from compound 26 (7.0 g, 14.60 mmol) analogously to the preparation of the substance 11 using dimethyl sulfide (3.4 ml, 46.53 mmol, 1 h, room temperature). Chromatography on silica gel (180 g, 6% ethyl acetate in petroleum ether) afforded 4.27 g (80%) of non-crystallising aldehyde 27, which was used crude in the next reaction: $^1H$ NMR (400 MHz, $CDCl_3$): 0.99 (3H, s, H-18), 1.24 (3H, s, H-19), 2.04 (3H, s, OAc), 2.62 (1H, dd, $J_1$=11.2 and $J_2$=3.0, H-14), 3.69 (3H, s, $OCH_3$), 5.05-5.11 (1H, m, H-3), 9.72 (1H, d, J=3.0, CHO). $^{13}C$ NMR (101 MHz, $CDCl_3$): δ 204.77, 177.45, 170.75, 70.45, 60.18, 52.32, 38.45, 45.24, 36.97, 36.85, 35.27, 32.41, 30.58, 30.51, 2633, 26.26, 25.10, 23.71, 21.61, 19.73, 16.89.

Example 25: Methyl (2S,4aS,4bS,7S,8aR,10aS)-7-acetoxy-2,4b-dimethyltetradecahydrophenanthren-2-carboxylate (28)

Compound 28 was prepared according to General Procedure VI—Wilkinson Decarbonylation of compound 27 (2 g, 5.49 mmol). Chromatography on silica gel (3% acetone in petroleum ether) afforded 1.31 g (71%, oil) of compound 28: $[\alpha]_D^{20}$ +14.6 (c 0.314, $CHCl_3$). $^1H$ NMR (400 MHz, $CDCl_3$): δ 0.95 (3H, s, H-18), 1.19 (3H, s, H-19), 2.05 (3H, s, H—OAc), 3.66 (3H, s, H—$OCH_3$), 5.03-5.10 (1H, m, H-3). $^{13}C$ NMR (101 MHz, $CDCl_3$): δ 179.37, 170.84, 70.79, 51.89, 42.43, 39.41, 37.56, 34.97, 34.49, 31.73, 30.65, 30.32, 28.82, 26.53, 25.21, 23.93, 21.65, 20.57, 20.51. IR spectrum ($CHCl_3$): 2975, 2941, 1491, 1378 (methyl); 1722 (C=O); 1262, 1243, 1025 (C—O). MS (ESI) m/z: 359.2 (100%, M+Na). HR-MS (ESI) m/z: For $C_{20}H_{32}O_4Na$ (M+Na) calcd: 359.2193; found: 359.2191.

Example 26: (2S,4aS,4bS,7S,8aS,10aR)-7-(Hydroxymethyl)-4a,7-dimethyltetradecahydrophenanthren-2-ol (29)

Compound 29 was prepared from compound 28 (1.25 g, 3.71 mmol) analogously to the preparation of the compound 13 to give 905 mg (92%) of the diol 29: mp 139-140° C. (ethyl-acetate/n-heptane), $[\alpha]_D^{20}$ +13.1 (c 0.29, $CHCl_3$). $^1H$ NMR (400 MHz, $CDCl_3$): δ 0.89 (3H, s, H-18), 0.95 (3H, s, H-19), 3.24-3.30 (2H, m, $CH_2OH$), 4.08-4.14 (1H, m, H-3). $^{13}C$ NMR (400 MHz, $CDCl_3$): δ 74.89, 67.29, 42.71, 39.88, 39.08, 35.85, 35.34, 34.37, 33.59, 31.92, 29.62, 29.34, 28.10, 26.79, 24.09, 20.74, 20.32. IR spectrum (CHCl$_3$): 3630, 3618 (OH); 2936, 2863 (CH$_2$); 1031, 998 (C—OH). MS (ESI) m/z: 289.2 (100%, M+Na). HR-MS (CI) m/z: For C$_{17}$H$_{29}$O$_2$ (M–H) calcd: 265.2168; found: 265.2170.

Example 27: (2S,4aS,4bS,8aR,10aS)-2,4b-Dimethyl-7-oxotetradecahydrophenanthren-2-carbaldehyde (30)

Anhydrous sodium acetate (158 mg, 1.93 mmol) and pyridinium chlorochromate (826 mg, 3.86 mmol) were added to a solution of compound 29 (320 mg, 1.20 mmol) in dichloromethane (20 ml). The reaction mixture was stirred at room temperature under an inert atmosphere of argon for 2 h and then it was diluted with ethyl acetate (80 ml) and filtered through a column of neutral alumina (60 g). The solvents were evaporated under reduced pressure to obtain 280 mg (89%) of aldehyde 30, which was used crude in the next reaction: $^1$H NMR (400 MHz, CDCl$_3$): δ 1.02 (3H, s, H-19), 1.12 (3H, s, H-18), 9.41 (1H, s, CHO). $^{13}$C NMR (101 MHz, CDCl$_3$): δ 212.89, 206.05, 44.45, 42.37, 40.38, 39.05, 37.35, 36.57, 35.11, 31.29, 31.17, 29.85, 28.45, 26.60, 22.81, 20.02, 17.58.

Example 28: (4aS,4bS,7R,8aS,10aR)-4a,7-Dimethyldodecahydrophenanthren-2(1H)-one (31a), (4aS,4bS,8aS,10aR)-4a,7-dimethyl-3,4,4a,4b,5,8,8a,9,10,10a-decahydrophenanthren-2(1H)-one (31b) and (4aS,4bS,8aS,10aR)-4a,7-dimethyl-3,4,4a,4b,5,6,8a,9,10,10a-decahydrophenanthren-2(1H)-one (31c)

Compounds 31a, 31b, and 31c were prepared according to General Procedure VI—Wilkinson Decarbonylation of compound 30 (280 mg, 1.07 mmol). Chromatography on silica gel (3% acetone in petroleum ether) gave an inseparable mixture of three products 31a, 31b and 31c (210 mg, 91.1:4.3:4.6).

Example 29: (2R,4aS,4bS,7R,8aS,10aR)-4a,7-Dimethyldodecahydrophenanthren-2-ol (32a), (2R,4aS,4bS,8aS,10aR)-4a,7-dimethyl-3,4,4a,4b,5,8,8a,9,10,10a-decahydrophenanthren-2-ol (32b) and (2R,4aS,4bS,8aS,10aR)-4a,7-dimethyl-3,4,4a,4b,5,6,8a,9,10,10a-decahydrophenanthren-2-ol (32c)

A mixture of three compounds 31a, 31b and 31c in tetrahydrofuran (18 ml) was cooled to −40° C. and tri-tert-butoxy lithium aluminum hydride (210 mg, 0.83 mmol) was added while stirring. After 2 h, the mixture was warmed to room temperature and quenched with aqueous hydrochloric acid (5%, 20 ml). The product was extracted with chloroform, the combined organic extracts were washed with saturated sodium bicarbonate, saturated sodium chloride solution and dried over anhydrous sodium sulfate. The solvents were evaporated under reduced pressure to give a mixture of the three hydroxy derivatives 32a, 32b and 32c (180 mg).

Example 30: (2R,4aS,4bS,7R,8aS,10aR)-4a,7-Dimethyltetradecahydrophenanthren-2-ol (33)

To the residue of compounds 32a, 32l, and 32c dissolved in dichloromethane (15 ml) was added a mixture of sodium acetate (66 mg, 0.81 mmol), water (0.6 ml), and acetic peroxacetic acid (9%, 2.4 ml) and the reaction mixture was stirred for 2 h room temperature. The reaction was quenched by addition of saturated aqueous sodium sulfite solution and the product was extracted with chloroform, the combined organic extracts were washed with water and dried over anhydrous magnesium sulfate. The solvents were evaporated under reduced pressure and chromatography (5% acetone in petroleum ether) afforded 90 mg (36%, 3 steps) of desired compound 33: [α]$_D^{20}$ +24.0 (c 0.27, CHCl$_3$). $^1$H NMR (400 MHz, CDCl$_3$): δ 0.79 (3H, s, H-19), 0.84 (3H, d, J=7.3, H-18), 3.53 (1H, tt, J$_1$=11.1 and J$_2$=4.7, H-3). $^{13}$C NMR (101 MHz, CDCl$_3$): δ 72.11, 42.49, 41.02, 40.80, 36.58, 34.86, 34.81, 32.70, 30.95, 30.87, 29.48, 27.81, 27.37, 23.62, 19.35, 18.31. IR spectrum (CHCl$_3$): 3608 (OH); 2958, 2866 (methyl); 1038, 1029 (C—OH). MS (CI) m/z: 236.2 (8%, M), 235.2 (15%, M–H). HR-MS (CI) m/z: For C$_{16}$H$_{27}$O (M–H) calcd: 235.2062; found: 235.2070.

Example 31: 4-(((2R,4aS,4bS,7R,8aS,10aR)-4a,7-Dimethyltetradecahydrophenanthren-2-yl)oxy)-4-oxobutanoic acid (34)

Compound 34 was prepared according to General Procedure II—Preparation of C-3 Hemisuccinate from compound 33 (65 mg, 0.27 mmol). Chromatography on silica gel (10% acetone in petroleum ether) afforded 40 mg (43%) of 34: mp 119-121° C. (acetone/n-heptane), [α]$_D^{20}$ +43.9 (c 0.273, CHCl$_3$). $^1$H NMR (400 MHz, CDCl$_3$): δ 0.90 (3H, s, H-18), 0.94 (3H, d, J, 7.2, H-19), 2.74-2.54 (4H, m, H-2' a H-4'), 4.75 (1H, tt, J$_1$=11.4 and J$_2$=4.7, H-3). $^{13}$C NMR (100 MHz, CDCl$_3$): δ 171.26, 171.83, 75.29, 42.32, 40.99, 40.78, 34.84, 34.53, 32.67, 32.33, 30.92, 29.45, 29.40, 29.06, 27.80, 27.20, 26.89, 23.58, 19.36, 18.31. IR spectrum (CHCl$_3$): 1727, 1716 (C=O); 1280 (C—O, dimer); 1232, 1176 (COC). MS (ESI) m/z: 335.4 (100%, M–H). HR-MS (ESI) m/z: For C$_{20}$H$_{31}$O$_4$ (M–H) calcd: 335.2228; found: 335.2228.

Example 32: Pyridinium (2R,4aS,4bS,7R,8aS,10aR)-4a,7-dimethyltetradecahydrophenanthren-2-yl 2-sulfate (35)

Compound 35 was prepared according to General Procedure I—Preparation of C-3 Sulfate from compound 33 (108 mg, 0.46 mmol) affording sulfate 35 (66 mg, 36%): mp 147-149° C., [α]$_D^{20}$ +25.3 (c 0.25, CHCl$_3$). $^1$H NMR (400 MHz, CDCl$_3$): δ 0.88 (3H, s, H-18), 0.92 (3H, d, J=7.2, H-19), 4.46 (1H, tt, J$_1$=11.3 and J$_2$=4.8, H-3), 8.00 (2H, m, H-2' and H-4', pyridinium), 8.47 (1H, t, J=8.6, H-3', pyridinium), 8.95-9.01 (2H, m, H-1' and H-5', pyridinium). $^{13}$C NMR (100 MHz, CDCl$_3$): δ 145.78 (C-1', C-5'), 142.51 (C-3'), 127.26 (C-2', C-4'), 79.87, 42.52, 41.06, 40.74, 34.81, 34.70, 33.45, 32.72, 30.89, 29.40, 28.05, 27.81, 27.20, 23.54, 19.33, 18.30. IR spectrum (CHCl$_3$): 3140, 3099, 1490, 826 (pyH); 1380 (methyl); 1263, 1255, 1173, 1047, 953 (SO$_3$). MS ESI m/z: 315.3 (100%, M–H-pyridine). HR-MS (ESI) m/z: For C$_{16}$H$_{27}$O$_4$S (M–H-pyridine) calcd: 315.1636; found: 315.1634.

Example 33: Methyl (2S,4aS,4bS,7S,8aR,10aS)-7-hydroxy-2,4b-dimethyltetradecahydrophenanthren-2-carboxylate (36)

A mixture of potassium hydroxide (1.3 g, 23.2 mmol) in water (1 ml) and methanol (40 ml) was added to a solution of acetate 28 (1.7 g, 5.1 mmol) in methanol (85 ml) while stirring. After 7 h of standing at room temperature, the reaction mixture was concentrated under reduced pressure to ⅓ of its volume and the product was extracted with ethyl acetate (3×20 ml), the combined organic phases were washed with water (2×20 ml), dilute hydrochloric acid (5%, 2×20 ml), saturated sodium bicarbonate, saturated sodium chloride solution and dried over anhydrous sodium sulfate. The solvents were evaporated under reduced pressure yielding 1.24 g (83%) of non-crystallizing compound 36: $[\alpha]_D^{20}$ +13.5 (c 0.47, CHCl$_3$). $^1$H NMR (400 MHz, CDCl$_3$): δ 0.94 (3H, s, H-19), 1.19 (3H, s, H-18), 3.66 (3H, s, H—OCH$_3$), 4.07-4.15 (1H, m, H-3). $^{13}$C NMR (101 MHz, CDCl$_3$): δ 179.45, 67.19, 51.87, 42.49, 39.26, 36.76, 35.22, 34.53, 33.54, 31.71, 29.50, 28.96, 28.06, 26.68, 23.97, 20.57, 20.51. IR spectrum (CHCl$_3$): 1719 (C═O); 1381 (methyl); 1245, 1033 (C—O). MS ESI m/z: 317.2 (100%, M+Na). HR-MS (ESI) m/z: For C$_{18}$H$_{30}$O$_3$Na (M+Na) calcd: 317.2087; found: 317.2087.

Example 34: Methyl (2S,4aS,4bS,8aR,10aS)-2,4b-dimethyl-7-oxotetradecahydrophenanthren-2-carboxylate (37)

Jones reagent was added dropwise to a cooled (0° C.) solution of the hydroxy derivative 36 (300 mg, 1.02 mmol) in acetone (5 ml). The progress of reaction was followed by TLC and quenched with methanol (5 ml). The mixture was poured into water, the product was extracted with ethyl acetate (3×20 ml), the combined organic phases were washed with saturated sodium bicarbonate solution, water and dried over anhydrous sodium sulfate. The solvents were evaporated under reduced pressure yielding 250 mg (84%) of ketone 37: $[\alpha]_D^{20}$ +22.9 (c 0.38, CHCl$_3$). $^1$H NMR (400 MHz, CDCl$_3$): δ 1.00 (3H, s, H-19), 1.22 (3H, s, H-18), 3.66 (3H, s, OCH$_3$). $^{13}$C NMR (101 MHz, CDCl$_3$): δ 213.04, 179.09, 51.93, 44.51, 42.38, 42.24, 40.24, 37.38, 36.61, 35.02, 34.38, 31.58, 29.83, 28.38, 26.66, 22.75, 20.60, 20.55. IR spectrum (CHCl$_3$): 2980, 2934, 1465, 1435, 1383 (methyl); 1720, 1711 (C═O); 1244, 1124 (C—O). MS (ESI) m/z: 315.2 (100%, M+Na). HR-MS (ESI) m/z: For C$_{18}$H$_{28}$O$_3$Na (M+Na) calcd: 315.1931; found: 315.1929.

Example 35: Methyl (2S,4aS,4bS,7R,8aR,10aS)-7-hydroxy-2,4b-dimethyltetradecahydrophenanthren-2-carboxylate (38)

Compound 38 was prepared from compound 37 (100 mg, 0.34 mmol) analogously to the preparation of compound 32 affording crystallising hydroxy derivative 38 (71 mg, 71%): $[\alpha]_D^{20}$ +21.6 (c 0.19, CHCl$_3$). $^1$H NMR (400 MHz, CDCl$_3$): δ 0.90 (3H, s, H-18), 1.18 (3H, s, H-19), 3.66 (3H, s, H—OCH$_3$), 3.58-3.65 (1H, m, H-3). $^{13}$C NMR (101 MHz, CDCl$_3$): δ 179.37, 171.94, 51.88, 42.39, 42.33, 39.98, 36.52, 34.91, 34.66, 34.48, 31.91, 30.82, 29.10, 27.22, 23.46, 20.59, 20.33. IR spectrum (CHCl$_3$): 3608 (OH); 2976, 2936, 1435, 1389 (methyl); 2936, 2865 (CH$_2$); 1720 (C═O); 1192, 1126, 1036, 1022 (C—O). MS (ESI) m/z: 317.2 (100%, M+Na). HR-MS (ESI) m/z: For C$_{18}$H$_{30}$O$_3$Na (M+Na) calcd: 317.2087; found: 317.2088.

Example 36: 4-(((2R,4aS,4bS,7S,8aS,10aR)-7-(Methoxycarbonyl)-4a,7,8a-trimethyltetradecahydrophenanthren-2-yl)oxy)-4-oxobutanoic aced (39)

Compound 39 was prepared according to General Procedure II—Preparation of C-3 Hemisuccinate from compound 38 (60 mg, 0.20 mmol). Chromatography on silica gel (15% acetone in petroleum ether) afforded 42 mg (52%) of derivative 39: mp 110-111° C. (acetone/n-heptane), $[\alpha]_D^{20}$ +23.3 (c 0.29, CHCl$_3$). $^1$H NMR (400 MHz, CDCl$_3$): δ 0.91 (3H, s, H-19), 1.19 (3H, s, H-18), 2.56-2.72 (4H, m, H-2' and H-4'), 3.66 (3H, s, H—OCH$_3$), 4.75 (1H, tt, J$_1$=11.3, J$_2$=4.7, H-3). $^{13}$C NMR (101 MHz, CDCl$_3$): δ 179.37, 176.38, 171.86, 75.02, 51.91, 42.42, 42.39, 42.15, 39.97, 34.70, 34.58, 34.48, 32.24, 31.89, 29.46, 29.02, 28.92, 27.06, 26.83, 23.42, 20.58, 20.36. IR spectrum (CHCl$_3$): 2937 (OCH$_3$); 1718 (C═O); 1242, 1126, 1102 (C—O). MS (ESI) m/z: 393.3 (100%, M–H), 394.3 (25%, M). HR-MS (ESI) m/z: For C$_{22}$H$_{33}$O$_6$ (M–1) calcd: 393.2283; found: 393.2283.

Example 37: Methyl (2S,4aS,4bS,7R,8aR,10aS)-2,4b-dimethyl-7-(sulfooxy)tetradecahydrophenanthren-2-carboxylate (40)

Compound 40 was prepared according to General Procedure I—Preparation of C-3 Sulfate from compound 38 (100 mg, 0.34 mmol) affording sulfate 40 (72 mg, 47%): mp 115-118° C., $[\alpha]_D^{20}$ +24.1 (c 0.23, CHCl$_3$). $^1$H NMR (400 MHz, CDCl$_3$): δ 0.89 (3H, s, H-19), 1.17 (3H, s, H-18), 3.65 (3H, s, OCH$_3$), 4.45 (1H, tt, J$_1$=11.0 and J$_2$=5.0, H-3), 8.01 (2H, m, H-2' and H-4', pyridinium), 8.48 (1H, tt, J$_1$=7.9, J$_2$=1.5, H-3', pyridinium), 8.99 (2H, dd, J$_1$=6.5, J$_2$=1.4), H-1' and H-5', pyridinium). $^{13}$C NMR (101 MHz, CDCl$_3$): δ 179.39, 145.90 (C-1', C-5'), 142.46 (C-3'), 127.33 (C-2', C-4'), 79.55, 64.51, 51.87, 42.40, 42.33, 39.91, 34.83, 34.55, 34.48, 33.38, 31.84, 29.02, 28.01, 27.05, 23.38, 20.57, 20.29. IR spectrum (CHCl$_3$): 3140, 3099, 1490 (pyH); 1720 (C═O); 1435, 1380 (methyl); 1254, 1049, 957 (SO$_3$); 1245, 1192, 1013 (C—O). MS (ESI) m/z: 373.2 (100%, M–H-pyridine). HR-MS (ESI) m/z: For C$_{18}$H$_{29}$O$_6$S (M–H-pyridine) calcd: 373.1690; found: 373.1688.

Example 38: (4aS,4bS,7S,8aS,10aR)-7-(Hydroxymethyl)-4a,7-dimethyldodecahydrophenanthren-2(1H)-one (41)

Aqueous sodium hypochlorite solution (4.5%, 1.05 ml) was added to a solution of dial 29 (80 mg, 0.30 mmol) in acetic acid (2.5 ml). The reaction mixture was stirred at room temperature for 1 h, and then was added propan-2-ol (1.5 ml) and the mixture was stirred for 30 min. The reaction was quenched by addition of water (5 mL), the product was extracted with chloroform (3×10 ml), and the combined organic extracts were washed with brine and dried with anhydrous magnesium sulfate. The solvents were evaporated and the residue flash chromatographed on silica gel (4-10% acetone in petroleum ether) yielding 48 mg (60%) of oily ketone 41: $[\alpha]_D^{20}$ +26.1 (c 0.38, CHCl$_3$). $^1$H NMR (400 MHz, CDCl$_3$): δ 0.92 (3H, s, H-18), 1.01 (3H, s, H-19), 3.24-3.34 (2H, m, CH$_2$OH). $^{13}$C NMR (101 MHz, CDCl$_3$): δ 213.36, 74.67, 44.65, 42.48, 42.47, 40.85, 37.42, 36.74, 35.86, 35.14, 34.24, 31.79, 28.77, 26.76, 22.85, 20.84, 20.28. IR spectrum (CHCl$_3$): 3630 (OH); 2931, 2867 (CH$_2$); 1705 (C═O); 1034 (CCO). MS (ESI) m/z: 287.2 (100%, M+Na). HR-MS (ESI) m/z: For C$_{17}$H$_{28}$O$_2$Na (M+Na) calcd: 287.1982; found: 287.1981.

Example 39: ((4aS,4bS,7S,8aS,10aR)-4a,7-Dimethyldodecahydro-1H-spiro[phenanthren-2,2'-[1,3]dioxolan]-7-yl)methanol (42)

Compound 42 was prepared from compound 41 (350 mg, 132 mmol) analogously to the preparation of compound 15. Chromatography on silica gel (1% triethylamine and 10% ethyl acetate in petroleum ether) gave 336 mg (82%) of oily ketal 42: $[\alpha]_D^{20}$ +19.5 (c 0.11, CHCl$_3$). $^1$H NMR (400 MHz, CDCl$_3$): δ 0.89 (3H, s, H-18), 0.93 (3H, s, H-19), 3.26 (2H, s, CH$_2$OH), 3.93 (4H, s, OCH$_2$CH$_2$O). $^{13}$C NMR (101 MHz, CDCl$_3$): δ 110.20, 74.94, 64.39, 64.22, 42.70, 41.22, 39.96, 35.82, 35.75, 34.77, 34.39, 33.86, 31.90, 30.37, 29.23, 26.86, 23.30, 20.74, 20.27. IR spectrum (CHCl$_3$): 3630, 3475 (OH); 1382, 1364 (methyl); 1183, 1093, 1068, 947 (COCOC); 1034 (CCO). MS (ESI) m/z: 331.3 (100%, M+Na). HR-MS (ESI) m/z: For C$_{19}$H$_{32}$O$_3$Na (M+Na) calcd: 331.2244; found: 331.2246.

Example 40: (4aS,4bS,7S,8aS,10aR)-7-(Methoxymethyl)-4a,7-dimethyldodecahydro-1H-spiro-[phenanthren-2,2'-[1,3]dioxolane] (43a)

Sodium hydride (60% suspension in oil, 200 mg) was added to a solution of the ketal 42 (250 mg, 0.81 mmol) in dried tetrahydrofuran (17 ml) and the reaction mixture was stirred under inert atmosphere of argon for 1 h at 90° C. Methyl iodide was added (0.4 ml, 6.5 mmol) and the mixture was heated under inert atmosphere of argon for 5 h at 90° C. After cooling, the product was extracted with ethyl acetate; the combined organic extracts were washed with saturated aqueous sodium chloride solution and dried over anhydrous magnesium sulfate. Evaporation of the solvent afforded 240 mg (92%) of non-crystallising methoxy derivative 43a: $[α]_D^{20}$ +15.9 (c 0.41, CHCl$_3$). $^1$H NMR (400 MHz, CDCl$_3$): δ 0.89 (3H, s, H-18), 0.92 (3H, s, H-19), 2.99 (2H, s, CH$_2$), 3.33 (3H, s, OCH$_3$), 3.93 (4H, m, OCH$_2$CH$_2$O). $^{13}$C NMR (100 MHz, CDCl$_3$): δ 110.24, 85.24, 64.37, 64.21, 59.54, 43.20, 41.25, 39.85, 35.75, 35.23, 34.91, 34.76, 33.87, 31.87, 30.36, 29.19, 26.89, 23.30, 20.81, 20.73. IR spectrum (CHCl$_3$): 2928, 1449 (CH$_2$); 2832, 1438, 1387, 1381, 1366 (methyl); 1186, 1094, 1068, 947 (COCOC); 1102 (COC), MS (ESI) m/z: 345.3 (55%, M+Na). HR-MS (ESI) m/z: For C$_{20}$H$_{35}$O$_3$(M+H) calcd: 323.2581; found: 323.2580.

Example 41: (4aS,4bS,7S,8aS,10aR)-7-(Methoxymethyl)-4a,7-dimethyldodecahydrophenanthren-2(1H)-one (43)

To a solution of ketal 43a (145 mg, 0.45 mmol) in acetone (2.5 ml) was added diluted hydrochloric acid (5%, 50 ml) and the mixture was stirred at room temperature for 1 h. The reaction was quenched by addition of saturated aqueous sodium bicarbonate solution (10 ml), the product was extracted with ethyl acetate, and the combined organic extracts were washed with saturated aqueous sodium chloride solution and dried over anhydrous sodium sulfate. Evaporation of the solvent afforded 120 mg (96%) of non-crystalline keto derivative 43: $[α]_D^{20}$ +24.8 (c 0.42, CHCl$_3$). $^1$H NMR (400 MHz, CDCl$_3$): δ 0.91 (3H, s, H-18), 1.00 (3H, s, H-19), 3.02 (2H, s, CH$_2$OH), 3.34 (3H, s, OCH$_3$). $^{13}$C NMR (100 MHz, CDCl$_3$): δ 213.45, 84.91, 59.55, 46.05, 42.93, 42.49, 40.71, 37.43, 36.77, 35.27, 35.13, 34.70, 31.77, 28.72, 26.79, 22.85, 20.85, 20.83. IR spectrum (CHCl$_3$): 2931, 2866 (CH$_2$); 1706 (C=O); 1383 (methyl); 1102 (COC). MS (ESI) m/z: 301.3 (100%, M+Na), 279.3 (20%, M+H). HR-MS (ESI) m/z: For C$_{18}$H$_{30}$O$_2$Na (M+Na) calcd: 301.2138; found: 301.2138.

Example 42: (2R,4aS,4bS,7S,8aS,10aR)-7-(Methoxymethyl)-4a,7-dimethyltetradecahydrophenanthren-2-ol (44)

Compound 44 was prepared from compound 43 (40 mg, 0.14 mmol) analogously to the preparation of compound 17 by using methanol. Chromatography (10% acetone in petroleum ether) gave 28 mg (70%) of an oily hydroxy derivative 44: $[α]_D^{20}$ +19.7 (c 0.44, CHCl$_3$). $^1$H NMR (400 MHz, CDCl$_3$): δ 0.88 (3H, s, H-18), 0.89 (3H, s, H-19), 3.00 (2H, s, CH$_2$OH), 3.33 (3H, s, OCH$_3$), 3.58-3.67 (1H, m, H-3). $^{13}$C NMR (101 MHz, CDCl$_3$): δ 85.22, 72.05, 59.55, 43.15, 42.44, 40.48, 36.53, 35.21, 35.00, 34.88, 34.73, 32.06, 30.82, 29.40, 27.32, 23.54, 20.79, 20.52. IR spectrum (CHCl$_3$): 3609, 3451 (OH); 2956, 2865, 1388, 1380 (methyl); 1102 (COC); 1036 (C—OH). MS (ESI) m/z: 303.4 (100%, M+Na). HR-MS (ESI) in/z: For C$_{18}$H$_{32}$O$_2$Na (M+Na) calcd: 303.2295; found: 303.2295.

Example 43: 4-(((2R,4aS,4bS,7S,8aS,10aR)-7-(Methoxymethyl)-4a,7-dimethyltetradecahydrophenanthren-2-yl)oxy)-4-oxobutanoic acid (45)

Compound 45 was prepared according to General Procedure II—Preparation of C-3 Hemisuccinate from compound 44 (60 mg, 0.21 mmol). Chromatography on silica gel (10% acetone in petroleum ether) afforded 41 mg (50%) of the derivative 45: mp 107-109° C. (acetone/n-heptane), $[α]_D^{20}$ +38.8 (c 0.26, CHCl$_3$). $^1$H NMR (400 MHz, CDCl$_3$): δ 0.88 (3H, s, H-19), 0.90 (3H, s, H-18), 2.53-2.72 (4H, m, OCCH$_2$CH$_2$CO), 3.01 (2H, s, CH$_2$OH), 3.34 (3H, s, OCH$_3$), 4.69-4.81 (1H, m, H-3). $^{13}$C NMR (101 MHz, CDCl$_3$): δ 177.12, 171.83, 85.10, 75.17, 59.55, 43.06, 42.26, 40.44, 35.24, 34.78 (2×), 34.68, 32.24, 32.04, 29.45, 29.33, 29.04, 27.17, 26.81, 23.50, 20.85, 20.55. IR spectrum (CHCl$_3$): 1726, 1717 (C=O); 1385 (methyl); 1169, 1101 (COC). MS (ESI) m/z: 403.2 (100%, M+Na). HR-MS (ESI) m/z: For C$_{22}$H$_{36}$O$_5$Na (M+Na) calcd: 403.2455; found: 403.2455.

Example 44: Pyridinium (2R,4aS,4bS,7S,8aS,10aR)-7-(methoxymethyl)-4a,7-dimethyltetradecahydrophenanthren-2-yl 2-sulfate (46)

Compound 46 was prepared according to General Procedure I—Preparation of C-3 Sulfate from compound 44 (98 mg, 0.35 mmol). Sulfate 46 was obtained (105 mg, 68%): mp 132-134° C., $[α]_D^{20}$ +22.0 (c 0.26, CHCl$_3$). $^1$H NMR (400 MHz, CDCl$_3$): δ 0.87 (3H, s, H-19), 0.88 (3H, s, H-18), 3.65 (3H, s, OCH$_3$), 2.99 (2H, s, CH$_2$O), 3.32 (3H, s, CH$_3$O), 4.46 (1H, tt, J$_1$=11.1, J$_2$=4.8, H-3), 8.00 (2H, m, H-2' and H-4', pyridinium), 8.47 (1H, tt, J$_1$=7.9, J$_2$=1.7, H-3', pyridinium), 8.92-9.06 (2H, m, H-1' and H-5', pyridinium). $^{13}$C NMR (101 MHz, CDCl$_3$): δ 145.78 (C-1', C-5'), 142.52 (C-3'), 127.27 (C-2', C-4'), 85.23, 79.75, 59.53, 43.20, 42.47, 40.43, 35.22, 34.94, 34.91, 34.63, 33.39, 32.01, 29.34, 28.01, 27.17, 23.47, 20.79, 20.51. IR spectrum (CHCl$_3$): 3140, 3099, 1490, 1024 (pyridinium); 1388, 1381 (methyl); 1262, 1254, 1173, 1047 (SO$_3$); 1109, 1101 (COC). MS (ESI) m/z: 359.3 (100%, M−H-pyridine). HR-MS (ESI) m/z: For C$_{18}$H$_{31}$O$_5$S (100%, M−H-pyridine) calcd: 359.1898; found: 359.1895.

Example 45: (3R,5R,8S,9S,10S,13S,14S)-10,13-Dimethylhexadecahydro-1H-cyclopenta[a]phenanthren-3-ol (48)

Metallic zinc (42 g) was under stirring gradually added to a mixture of commercially available 3alpha-hydroxy-5beta-androstan-17-one 47 (6 g, 0.02 mol) in methanol (90 ml) and dichloromethane (90 ml). The reaction mixture was cooled to 0° C., then, trimethylsilyl chloride (84 ml) was added dropwise and the mixture was stirred at room temperature for 14 hours. Progress of the reaction was monitored on TLC. The mixture was filtered through cellulose and the filtrate was neutralized with saturated aqueous sodium bicarbonate solution. The product was extracted with chloroform (3×50 ml), the combined organic phases were washed with aqueous hydrochloric acid (5%, 30 ml), saturated aqueous sodium chloride solution, dried over anhydrous sodium sulfate and the solvents were evaporated under reduced pressure. The product was purified by silica gel chromatography (4% acetone in petroleum ether). It was isolated 4.5 g (79%) of compound 48: mp 143-144° C., $[\alpha]_D^{20}$ +10.9 (c 0.27, CHCl$_3$). IR spectrum (CHCl$_3$): 3608, 3446 (OH); 2972, 2887, 1377, (CH$_3$); 2935, 2865, 1450; (CH$_2$) 1081, 1065, 1034 (CO). $^1$H NMR (400 MHz, CDCl$_3$): δ 0.68 (3H, s, H-18), 0.92 (3H, s, H-19), 3.58-3.67 (1H, m, H-3). $^{13}$C NMR (101 MHz, CDCl$_3$): 72.05 (C-3), 54.73, 42.28, 41.09, 40.91, 40.64, 39.22, 36.65, 36.38, 35.63, 34.89, 30.73, 27.37, 26.99, 25.70, 23.56, 20.99, 20.74, 17.65. For C$_{19}$H$_{32}$O (276.2) calcd: 82.55% C, 11.67% H; found: 82.31% C, 11.82% H.

Example 46: Pyridinium (3R,5R,8S,9S,10S,13S,14S)-10,13-dimethylhexadecahydro-1H-cyclopenta[a]phenanthren-3-yl 3-sulfate (49)

Compound 49 was prepared according to General Procedure I—Preparation of C-3 Sulfate from compound 48 (200 mg, 0.72 mmol). White crystals of sulfate 49 (211 mg, 67%) were isolated: mp 180-182° C. (chloroform), $[\alpha]_D^{20}$ +16.0 (c 0.28, CHCl$_3$/MeOH, 2:0.1 ml). $^1$H NMR (400 MHz, CDCl$_3$): δ 0.67 (3H, s, H-18), 0.92 (1H, s, CH-19), 4.48 (1H, tt, J$_1$=11.3, J$_2$=4.9, H-3), 7.94-8.04 (2H, m, H-2 a H-4, pyridinium), 8.47 (1H, tt, J$_1$=7.9, J$_2$=1.6, H-3, pyridinium), 8.97 (2H, dt, J$_1$=5.6, J$_2$=1.5, H-1 a H-5, pyridinium). $^{13}$C NMR (101 MHz, CDCl$_3$/CD$_3$OD): δ 145.57 (C-1' and C-5', pyridium), 142.33 (C-3', pyridinium), 127.07 (C-2" and C-4', pyridinium), 79.71 (C-3), 54.67, 42.23, 40.97, 40.75, 40.53, 39.13, 36.23, 35.48, 34.67, 33.39, 27.80, 27.10, 26.81, 25.58, 23.35, 20.85, 20.61, 17.53. IR spectrum (CHCl$_3$): 1260, 1178, 1050, 970 (OSO$_3$). MS (EI) m/z: 355.2 (100%, M-pyridinium). HR-MS (ESI) m/z: For C$_{19}$H$_{31}$O$_4$S calcd: 355.1949; found: 355.1949.

Example 47: 2-(((3R,5R,8S,9S,10S,13S,14S)-10,13-Dimethylhexadecahydro-1H-cyclopenta[a]phenanthren-3-yl)oxy)-2-oxoethanoic acid (50)

5beta-androstan-3alpha-ol 48 (100 mg, 0.362 mmol) was dissolved in dried dichloromethane (2 ml). The solution was cooled to 0° C. and triethylamine (0.05 ml), a drop of a solution of N,N'-dimethylformamide (0.03 ml) in dichloromethane (2 ml), and oxalic acid chloride (0.09 ml, 1.086 mmol) were added while stirring. The mixture was warmed to 10° C. and stirred at this temperature for 2 h. The excess reagent was decomposed by addition of water (10 ml) and the solution was stirred at room temperature for 30 min. Then aqueous layer was separated, dichloromethane evaporated and the residue slurried in ethyl acetate (20 ml) and aqueous potassium carbonate (10%, 50 ml). The organic layer containing the neutral impurities were removed, the aqueous phase cautiously acidified with dilute hydrochloric acid (1N, to pH~4) and extracted with ethyl acetate (2×25 ml). The combined extracts were washed with water, dried over anhydrous sodium sulfate and the solvents evaporated under reduced pressure. Crystallization from acetone/n-heptane yielded 70 mg (55%) of oxalic acid hemiester 50: $[\alpha]_D^{20}$ +27.9 (c 0.32, CHCl$_3$). $^1$H NMR (400 MHz, CDCl$_3$): δ 0.68 (3H, s, H-18), 0.96 (3H, s, H-19), 4.95 (1H, tt, J$_1$=11.4, J$_2$=4.9, H-3). $^{13}$C NMR (101 MHz, CDCl$_3$): δ 157.83, 157.48, 79.67, 54.69, 42.12, 41.08, 40.83, 40.60, 39.13, 36.30, 35.13, 34.88, 31.89, 27.11, 26.81, 26.32, 25.67, 23.37, 20.99, 20.72, 17.63. IR spectrum (CHCl$_3$): 1734, 1726 (C=O), 1268, 1246 (C—O). MS (ESI) m/z: 275.3 (100%, M-COCOO), 347.3 (10%, M–H). HR-MS (ESI) in/z: For C$_{21}$H$_{31}$O$_4$ (M–H) calcd: 347.2228; found: 347.2232.

Example 48: 2-(((3R,5R,8S,9S,10S,13S,14S)-10,13-Dimethylhexadecahydro-1H-cyclopenta[a]phenanthren-3-yl)oxy)-2-oxopropanoic acid (51)

Compound 51 was prepared according to General Procedure III—Preparation of C-3 Hemimalonate from compound 48 (100 mg, 0.36 mmol). Chromatography on silica gel (1-10% acetone in petroleum ether) afforded 67 mg (51%) of non-crystallizing derivative 51: $[\alpha]_D^{20}$ +27.8 (c 0.35, CHCl$_3$). $^1$H NMR (400 MHz, CDCl$_3$): δ 0.68 (3H, s, H-18), 0.94 (3H, s, H-19), 3.42 (2H, s, H-2'), 4.80-4.90 (1H, m, H-3). $^{13}$C NMR (101 MHz, CDCl$_3$): δ 169.05, 168.01, 77.04, 54.72, 42.10, 41.10, 40.94, 40.64, 40.20, 39.17, 36.33, 35.20, 34.90, 32.16, 27.15, 26.87, 26.59, 25.68, 23.48, 21.02, 20.75, 17.66. IR spectrum (CHCl$_3$): 1755, 1736, 1717 (C=O); 1330 (OH). MS (ESI) m/z: 317.3 (100%, M–HCOOH), 361.3 (20%, M–H), 723.6 (10%, 2M–H). HR-MS (ESI) m/z: For C$_{22}$H$_{33}$O$_4$ (M–H) calcd: 361.2385: found: 361.2380.

Example 49: (3R,5R,8S,9S,10S,13S,14S)-10,13-Dimethylhexadecahydro-1H-cyclopenta[a]phenanthren-3-yl N-2-((benzyloxy)-carbonyl)-N-omega-nitro-L-argininate (52)

A mixture of compound 48 (150 mg, 0.54 mmol), the protected Z,NO$_2$ argininate (211 mg, 0.6 mmol) and 4-(N,N-dimethylamino)pyridine (7 mg, 0.06 mmol) were dissolved in acetonitrile (20 ml) and dichloromethane (10 ml) and a solution of dicyclohexylcarbodiimide in benzene (1M, 0.813 ml) was added. The reaction mixture was stirred under argon for 17 h. The precipitated derivative N,N'-dicyclohexylurea was removed by filtration and the filtrate poured into saturated sodium bicarbonate solution, the product was extracted into ethyl acetate (3×25 ml), the combined organic phases were washed with brine (25 ml) and dried over anhydrous magnesium sulfate. The solvents were evaporated under reduced pressure. Purification of the crude residue (484 mg) by column chromatography on silica gel (20% acetone in petroleum ether) gave the product 52 (226 mg, 68%): mp 132-133° C., $[\alpha]_D^{20}$ –7.5 (c 0.25, CHCl$_3$). $^1$H NMR (500 MHz, CDCl$_3$): δ 0.69 (3H, s, H-18), 0.95 (3H, s, H-19), 3.22-3.31 (1H, m, 5'b-CH), 3.41-3.50 (1H, m, 5'a-CH), 4.28-4.36 (1H, m, 2'-CH), 4.73-4.83 (1H, m, H-3), 5.12 (2H, s, CH$_2$-benzyl), 5.75 (1H, d, J=8.0, NHCBz), 7.23-7.40 (5H, m, phenyl). $^{13}$C NMR (101 MHz, CDCl3): δ 171.43, 159.42, 136.01, 128.70, 128.49, 127.88, 76.57, 67.51, 54.54, 42.04, 40.98, 40.83, 40.50, 40.41, 40.29, 39.01, 36.24, 35.07, 34.78, 33.91, 32.20, 31.17, 27.06, 26.74, 26.58, 25.64, 26.56, 24.95, 24.48, 2334, 20.92, 20.63, 17.55. IR spectrum: 1730 (C=O, ester); 1705 (C=O, carbamate); 1348, 1326, 1291 (NO$_2$); 1231 (phenyl). MS (ESI) m/z: 634 (100%, M+Na), 612 (70%, M+H).

Example 50: (3R,5R,8S,9S,10S,13S,14S)-10,13-Dimethylhexadecahydro-1H-cyclopenta[a]phenanthren-3-yl L-argininate dihydrochloride (53)

To a solution of androstanol-Boc,NO$_2$-argininate—52 (203 mg, 0.33 mmol) in methanol (9.5 ml) and acetic acid (0.5 ml) was added palladium catalyst (Pd/C, 10%, 20.3 mg). The mixture was vigorously stirred under a slight positive pressure of hydrogen for 18 h at room temperature. The reaction was monitored by TLC, in a mixture of petroleum ether/acetone, 1:1. After disappearance of the starting material the catalyst was filtered over a small column of celite. The filtrate was diluted with chloroform (5 ml), washed with dilute hydrochloric acid (5%, 5 ml) and dried over anhydrous magnesium sulfate. The precipitated hydrochloride 53 (140 mg, 84%) was dried. The product 53 was recrystallized from methanol/water: mp 238-240° C., $[\alpha]_D^{20}$ +20 (c 0.32, CHCl$_3$). $^1$H NMR (400 MHz, CDCl$_3$): δ 0.74 (3H, s, H-18), 1.00 (3H, s, H-19), 3.27 (2H, d, J=7.8, H-5'), 4.06 (1H, d, J=7.8, H-2'), 4.89 (1H, m, H-3). $^{13}$C NMR: (101 MHz, CD$_3$OD): δ 169.69, 78.49, 62.66, 55.92, 53.69, 43.29, 42.16, 42.03, 41.67, 41.54, 37.52, 35.83, 33.19, 28.75, 28.09, 27.92, 27.57, 26.52, 25.64, 25.54, 23.75, 21.94, 21.43, 22.13, 17.86. IR spectrum (CHCl$_3$): 3344, 3164, (NH); 1703, 1681, 1600 (guanidinium); 1727 (C═O, ester). MS (ESI) m/z: 433.4 (100%, M−2HCl). HR-MS (ESI) m/z: For C$_{25}$H$_{45}$N$_4$O$_2$ (M−2HCl) calcd: 433.3537; found: 433.3537.

Example 51: (3S,5R,8S,9S,10S,13S,14S)-10,13-Dimethylhexadecahydro-1H-cyclopenta[a]phenanthren-3-yl 4-methylbenzensulfonate (55)

Compound 55 was prepared according to General Procedure VIII—Tosylation from 5beta-androstan-3beta-ol 54 (prepared by the same procedure as compound 48, 4 g, 14.47 mmol) affording compound 55 (5.88 g, 94%): $[\alpha]_D^{20}$ +2.9 (c 0.61, CHCl$_3$). $^1$H NMR (400 MHz, CDCl$_3$): δ 0.66 (3H, s, H-18), 0.94 (3H, s, H-19), 2.44 (3H, s, CH$_3$-tosylate), 4.81-4.85 (1H, m, H-3), 7.32 (2H, d, J=8.2, tosylate), 7.79 (2H, d, J=8.2, tosylate). $^{13}$C NMR (101 MHz, CDCl$_3$): δ 144.38, 134.95, 129.83 (2×), 127.75 (2×), 81.06, 54.80, 41.08, 40.62, 40.52, 39.19, 36.91, 36.10, 34.96, 31.49, 30.25, 26.64, 26.37, 25.96, 25.63, 23.78, 21.77, 21.21, 20.71, 17.65. IR spectrum (CHCl$_3$): 2960 (CH$_3$); 1174 (SO$_2$); 905 (C—O). MS (ESI) m/z: 883.4 (100%, 2M+Na), 453.2 (80%, M+Na). HR-MS (ESI) m/z: For C$_{26}$H$_{38}$O$_3$NaS (M+Na) calcd: 453.2434; found: 453.2434.

Example 52: (3R,5R,8S,9S,10S,13S,14S)-3-Azido-10,13-dimethylhexadecahydro-1H-cyclopenta[a]phenanthrene (56)

Compound 56 was prepared according General Procedure IX—Substitution of Tosylate Protecting Group with Alkali Azide from compound 55 (5.88 g, 13.68 mmol). Purification by column chromatography (2% ether in petroleum ether) afforded 2.8 g (68%) of 3alpha-azide (56) and 0.8 g (19%) of a mixture (1:1) with 3beta-isomer. Compound 56: $[\alpha]_D^{20}$ +22.4 (c 0.29, CHCl$_3$). $^1$H NMR (400 MHz, CD$_3$OD): δ 0.68 (3H, s, H-18), 0.94 (3H, s, H-19), 3.31 (1H, tt, J$_1$=11.8, J$_2$=4.5, H-3). $^{13}$C NMR (101 MHz, CDCl$_3$): δ 61.43, 54.64, 42.57, 41.07, 40.92, 40.61, 39.12, 36.33, 35.85, 34.95, 32.63, 27.27, 26.90 (2×), 25.67, 23.63, 20.98, 20.72, 17.65. IR spectrum (CHCl$_3$): 2937, 2868 (CH$_3$); 2094 (N$_3$). MS (ESI) m/z: 274.25 (100%, M−N$_2$H), 259.24 (40%, M−N$_3$H). HR-MS (ESI) m/z: For C$_{19}$H$_{31}$ (M−N$_3$) calcd: 259.2426; found: 259.2423.

Example 53: (3R,5R,8S,9S,10S,13S,14S)-10,13-Dimethylhexadecahydro-1H-cyclopenta[a]phenanthren-3-amine (57)

Compound 57 was prepared according to General Procedure V—Catalytic Hydrogenation from compound 56 (2.80 g, 9.29 mmol). Chromatography on silica gel (20% methanol and 1% triethylamine in dichloromethane) yielded 1.74 g (68%) of amine 57: $[\alpha]_D^{20}$ +14.0 (c 0.47, CHCl$_3$/MeOH, 1.8:0.1). $^1$H NMR (400 MHz, CD$_3$OD): δ 0.67 (3H, s, H-18), 0.93 (3H, s, H-19), 2.80 (1H, m, H-3). $^{13}$C NMR (101 MHz, CDCl$_3$): δ 54.64, 51.79, 42.69, 41.09, 40.89, 40.64, 39.18, 36.42, 36.22, 34.95, 30.45, 27.38, 27.01, 25.72, 25.66, 23.75, 21.00, 20.75, 17.67. IR spectrum (hydrochloride) (KBr): 3104 (NH$_3^+$); 2973, 1450, 1377 (CH$_3$). MS (ESI) m/z: 276.3 (100%, M+H). HR-MS (ESI) m/z: For C$_{19}$H$_{34}$N (M+H) calcd: 276.2686; found: 276.2686.

Example 54: Ethyl 2-(((3R,5R,8S,9S,10S,13S,14S)-10,13-dimethylhexadecahydro-1H-cyclopenta[a]phenanthren-3-yl)amino)-2-oxoacetate (58)

Compound 58 was prepared according to General Procedure XI—Reaction of C-3 Amino Group with Ethyl Chlorooxoacetate from compound 57 (100 mg, 0.36 mmol) affording 123 mg (90%) of 58: mp 165-167° C. (acetone/n-heptane), $[\alpha]_D^{20}$ +36.7 (c 0.38, CHCl$_3$). $^1$H NMR (400 MHz, CD$_3$OD): δ 0.68 (3H, s, H-18), 0.95 (3H, s, H-19), 1.38 (3H, t, J=7.1, CH$_2$CH$_3$), 3.75-3.87 (1H, m, H-3), 4.34 (2H, q, J=7.1, CH$_2$CH$_3$), 6.96 (1H, d, J=8.6, NH). $^{13}$C NMR (101 MHz, CDCl$_3$): δ 161.21, 155.77, 63.29, 54.82, 50.24, 42.44, 41.10, 41.04, 40.65, 39.22, 35.94, 34.86, 33.26, 29.85, 27.57, 27.12, 26.94, 25.68, 23.70, 20.99, 20.73, 17.65, 14.16. IR spectrum (CHCl$_3$): 1696 (C═O); 1377 (OEt). MS (ESI) m/z: 398.3 (100%, M+Na). HR-MS (ESI) m/z: For C$_{23}$H$_{37}$O$_3$NNa (M+Na) calcd: 398.2666; found: 398.2668.

Example 55: 2-(((3R,5R,8S,9S,10S,13S,14S)-10,13-Dimethylhexadecahydro-1H-cyclopenta[a]phenanthren-3-yl)amino)-2-oxoacetic acid (59)

To a solution of protected amide 58 (110 mg, 0.29 mmol) in methanol (3 ml) cooled to 0° C. was added dropwise a solution of sodium hydroxide (120 mg, 3 mmol) in methanol (2 ml). The reaction mixture was stirred at 10° C. for 2 h. It was then poured into water, acidified with dilute hydrochloric acid (5%) to pH-2 and the product extracted into ether (3×10 ml). The combined organic phases were washed with brine, dried over anhydrous sodium sulfate and the solvents evaporated under reduced pressure yielding 59 mg (64%) of the monoamide 59: mp 191-193° C., $[\alpha]_D^{20}$ +32.4 (c 0.21, CHCl$_3$/MeOH, 1.8:0.4). $^1$H NMR (400 MHz, CD$_3$OD): δ 0.69 (3H, s, H-18), 0.96 (3H, s, H-19), 3.70-3.85 (1H, m, H-3), 7.14 (1H, d, J=8.2, NH). $^{13}$C NMR (101 MHz, CDCl$_3$): δ 160.05, 156.62, 54.77, 51.29, 42.45, 41.10, 41.04, 40.62, 39.17, 36.32, 35.83, 34.85, 33.08, 27.40, 27.08, 26.90, 25.67, 23.67, 21.00, 20.72, 17.65. IR spectrum (sodium salt) (KBr): 1649 (C═O, amide); 1532 (amide); 1377 (CH$_3$). MS (ESI) m/z 346.2 (100%, M−H). HR-MS (ESI) m/z: For C$_{19}$H$_{32}$NO$_3$ (M−H) calcd: 346.2388; found: 346.2386.

Example 56: ((3R,5R,8S,9S,10S,13S,14S)-10,13-Dimethylhexadecahydro-1H-cyclopenta[a]phenanthren-3-yl)amin)-3-oxopropanoic acid (61)

Compound 60 was prepared according to General Procedure X—Reaction of C-3 Amino Group with Methyl 3-Chloro-oxopropionate from compound 57 (100 mg, 0.36 mmol) affording methyl ester 60 (130 mg, 96%), which formed (by IR and NMR spectra) equilibrium mixture of keto and enol form, and after characterization by mass spectra was used for the next reaction. MS (ESI) m/z: 398.4 (100%, M+Na), 773.8 (40%, 2M+Na). HR-MS (ESI) m/z: For $C_{23}H_{37}NO_3Na$ (M+Na) calcd: 398.2666; found: 398.2666.

A solution of 60 (130 mg, 0.35 mmol) and sodium hydroxide (28 mg, 0.69 mmol) in tetrahydrofuran (1.5 ml) and water (1.5 ml) was stirred at room temperature for 3 h. The reaction mixture was poured into water and neutral fractions were removed by extraction with ether. The aqueous phase was acidified with dilute hydrochloric acid (5%). The product was extracted into ethyl acetate (3×15 ml). The combined organic extracts were washed with water and dried over anhydrous magnesium sulfate and the solvents evaporated under reduced pressure. Chromatography on silica gel (10% acetone in petroleum ether) afforded 48 mg (37%) of 61: mp 126-128° C., $[\alpha]_D^{20}$ +25.4 (c 0.25, $CHCl_3$). $^1H$ NMR (400 MHz, $CD_3OD$): δ 0.68 (3H, s, H-18), 0.95 (3H, s, H-19), 3.29 (2H, s, $COCH_2CO$), 3.83 (1H, tdt, $J_2$=12.4, $J_2$=8.7, $J_3$=4.6, H-3), 6.3 (1H, d, J=8.4, NH). $^{13}C$ NMR (101 MHz, $CDCl_3$): δ 168.78, 167.91, 54.83, 50.59, 42.49, 41.09, 41.03, 40.65, 39.22, 38.58, 36.31, 35.94, 34.86, 33.33, 27.62, 27.11, 26.94, 25.67, 23.68, 20.98, 20.73, 17.64. IR spectrum (KBr): 1731, 1719 (C=O, amide); 1630, 1622, 1561 (amide); 1377 ($CH_3$). MS (ESI) m/z: 360.3 (100%, M−H), 721.5 (25%, 2M−H). HR-MS (ESI) m/z: For $C_{22}H_{34}NO_3$(M−H) calcd: 360.2544; found: 360.2536.

Example 57: 4-(((3R,5R,8S,9S,10S,13S,14S)-10,13-Dimethylhexadecahydro-1H-cyclopenta[a]-phenanthren-3-yl)oxy)-N,N,N-trimethyl-4-oxobutan-1-ammonium chloride (62)

3-Carboxy-N,N,N-trimethylpropane-1-ammonium chloride (69 mg, 0.38 mmol) was suspended in anhydrous $CH_2Cl_2$ (1 ml) under argon. To the reaction mixture cooled in an ice bath was added dropwise oxalic acid chloride (0.5 ml, 5.82 mmol) followed by a catalytic amount of anhydrous N,N'-dimethylformamide (3 ml, 0.03 mmol). The heterogeneous mixture was stirred at ambient temperature for 16 h. During this time a clear solution formed. The liquid portions of the mixture were evaporated under reduced pressure and the solid residue was dissolved in nitromethane (2 ml) and anhydrous pyridine (0.10 ml, 1.24 mmol) under argon. To this solution was added compound 48 (98 mg, 0.35 mmol). The reaction was stirred 4 h and then, it was quenched with water (10 ml). The resulting mixture was acidified to pH-4 with aqueous HCl (5%). The product was extracted with chloroform (3×20 ml), the solution washed with saturated aqueous sodium chloride solution (10 ml), dried over anhydrous magnesium sulfate and evaporated under reduced pressure. The unreacted starting steroid 48 was removed by trituration with benzene and the residual product was recrystallized from chloroform/n-heptane (1:1) affording crystals of 62 (122 mg, 79%): mp 225-227° C. (n-heptane/$CHCl_3$), $[\alpha]_D^{20}$ +24.9 (c 0.23, $CHCl_3$). $^1H$ NMR (400 MHz, $CDCl_3$): δ 0.69 (3H, s, H-18), 0.94 (3H, s, H-19), 2.03-2.14 (2H, br m, H-3') 2.46-2.50 (2H, br m, H-2'), 3.46 (9H, br s, N($CH_3$)$_3$), 3.63-3.71 (2H, br m, H-4'), 4.72 (1H, tt, $J_1$=11.3, $J_2$=4.6, H-3). $^{13}C$ NMR (101 MHz, $CDCl_3$): δ 171.55 (CO), 75.45, 65.73, 54.53, 53.60, 41.98, 40.92, 40.77, 40.46, 39.00, 36.18, 35.12, 34.74, 32.26, 30.28, 27.03, 26.71, 26.63, 25.51, 23.33, 20.86, 20.57, 18.50, 17.50. IR spectrum ($CHCl_3$): 2950 ($CH_3$); 1722 (C=O, ester); 1477 ($NMe_3^+$) 1386 ($CH_3$); 1230 ($NMe_3^+$); 1185 (CO). MS (ESI) m/z: 404 (100%, M−Cl). (ESI) m/z: For $C_{26}H_{45}NO_2$ (M−Cl) calcd: 404.3523; found: 404.3526.

Example 58: 4-(((3R,5R,8R,9S,10S,13R,14S)-10,13-Dimethyl-2,3,4,5,6,7,8,9,10,11,12,13,14,15-tetradecahydro-1H-cyclopenta[a]phenanthren-3-yl)oxy)-4-oxobutanoic acid (64)

Compound 64 was prepared according to General Procedure II—Preparation of C-3 Hemisuccinate from compound 63 (103 mg, 0.38 mmol). Chromatography on silica gel (25% ethyl acetate in petroleum ether) afforded 85 mg (60%) of the derivative 64: mp 127.7-128.3° C. (acetone/n-heptane), $[\alpha]_D^{20}$ +30.8 (c 0.27, $CHCl_3$). $^1H$ NMR (400 MHz, $CDCl_3$): δ 0.74 (3H, s, H-18), 0.97 (3H, s, H-19), 2.58-2.71 (4H, m, $OCCH_2CH_2CO$), 4.75 (1H, tt, $J_1$=11.3, $J_2$=4.8, H-3), 5.69 (1H, ddd, $J_1$=5.6, $J_2$=2.9, $J_3$=1.4, H-17), 5.83 (1H, m, H-16). $^{13}C$ NMR (101 MHz, $CDCl_3$): δ 177.03, 171.66, 143.89, 129.29, 74.95, 56.16, 45.64, 42.00, 41.30, 36.09, 35.00, 34.92, 34.49, 32.25, 32.01, 29.28, 28.87, 27.00, 26.54, 23.31, 20.72, 17.03. IR spectrum ($CHCl_3$): 1717, 1726 (C=O, COOH); 1578 (C=C). MS (ESI) m/z: 397.3 (100%, M+Na). HR-MS (ESI) m/z: For $C_{23}H_{34}O_4Na$ (M+Na) calcd: 397.23493; found: 397.23484.

Example 59: 3-(((3R,5R,8R,9S,10S,13R,14S)-10,13-Dimethyl-2,3,4,5,6,7,8,9,10,11,12,13,14,15-tetradecahydro-1H-cyclopenta[a]phenanthren-3-yl)oxy)-3-oxopropanoic acid (65)

Compound 65 was prepared according to General Procedure III—Preparation of C-3 Hemimalonate from compound 63 (102 mg, 0.37 mmol). Chromatography on silica gel (25% ethyl acetate in petroleum ether) gave (102 mg, 76%) of the derivative 65: mp 156.7-157.8° C. (acetone/n-heptane), $[\alpha]_D^{20}$ +30.4 (c 0.31, $CHCl_3$). $^1H$ NMR (400 MHz, $CDCl_3$): δ 0.74 (3H, s, H-18), 0.98 (3H, s, H-19), 3.42 (2H, s, H-2'), 4.84 (1H, tt, $J_1$=11.3, $J_2$=4.8, H-3), 5.69 (1H, ddd, $J_1$=5.6, $J_2$=2.9, $J_3$=1.4, H-17), 5.83 (1H, m, H-16). $^{13}C$ NMR (101 MHz, $CDCl_3$): δ 169.06, 167.78, 143.84, 129.29, 76.90, 56.13, 45.64, 42.00, 41.32, 40.08, 36.06, 34.90 (2×C), 34.48, 32.05, 31.99, 26.95, 26.51, 26.38, 23.27, 20.73, 17.03. IR spectrum ($CHCl_3$): 1760, 1735, 1719 (C=O); 1587 (C=C). MS (ESI) m/z: 383.2 (100%, M+Na). HR-MS (ESI) m/z: For $C_{22}H_{32}O_4Na$ (M+Na) calcd: 383.2193; found: 383.2192.

Example 60: (3R,5R,8R,9S,10S,13S,14S)-10,13-Dimethyl-17-methylenhexadecahydro-1H-cyclopenta[a]phenanthren-3-ol (66)

Sodium hydride (60% in parafin oil, 80 mg, 1.7 mmol) was added to a solution of methyltriphenylphosphonium bromide (619 mg, 1.73 mmol) in dried dimethyl sulphoxide (4 ml) under an inert atmosphere of nitrogen and the reaction mixture was stirred at room temperature for 1 h. Then, a solution of 17-oxo-5beta-androstan-3alpha-ol 47 (100 mg, 0.34 mmol) in dried tetrahydrofuran (3 ml) was added and after stirring for 1.5 h at 70° C., an aqueous ammonium chloride solution was added. The product was extracted into chloroform (2×20 ml), the combined organic extracts were washed with saturated aqueous sodium chloride solution and dried over anhydrous sodium sulfate. The solvents were evaporated under reduced pressure and the residue purified by preparative thin layer chromatography (eluted with 40% ether in petroleum ether) affording compound 66 (90 mg, 90%): mp 147-149° C. (acetone/n-heptane), $[\alpha]_D^{20}$ +30.5 (c 0.22, CHCl$_3$). $^1$H NMR (400 MHz, CDCl$_3$): δ 0.75 (3H, s, H-18), 0.93 (3H, s, H-19), 2.22 (1H, dtt, J$_1$=17.7, J$_2$=8.8, J$_3$=2, H$_a$-16), 2.47 (1H, dddd, J$_1$=16.9, J$_2$=10, J$_3$=4.4, J$_4$=2.2, H$_b$-16), 3.62 (1H, m, H-3), 4.50-4.62 (2H, m, =CH$_2$). $^{13}$C NMR (101 MHz, CDCl$_3$): δ 162.07 (C-17), 100.79 (C-20), 71.97 (C-3), 54.63, 44.34, 42.32, 40.89, 36.59, 36.04, 35.97, 35.57, 34.88, 30.69, 29.60, 27.28, 26.51, 24.32, 23.53, 20.86, 18.66. IR spectrum (CHCl$_3$): 3609, 3451, 1031 (OH); 1653 (C=C). MS (ESI) m/z: 311.3 (100%, M+Na). HR-MS (ESI) m/z: For C$_{20}$H$_{32}$ONa (M+Na) calcd: 311.2345, found: 311.2344.

Example 61: 3-(((3R,5R,8R,9S,10S,13S,14S)-10,13-Dimethyl-17-methylenehexadecahydro-1H-cyclopenta[a]phenanthren-3-yl)oxy)-3-oxopropanoic acid (67)

Compound 67 was prepared according to General Procedure III—Preparation of C-3 Hemimalonate from compound 66 (200 mg, 0.69 mmol). Chromatography on silica gel (1-10% acetone in petroleum ether) gave compound 67 (239 mg, 92%): mp 109-111° C. (acetone/n-heptane), $[\alpha]_D^{20}$ +49.5 (c 0.31, CHCl$_3$). $^1$H NMR (400 MHz, CDCl$_3$): δ 0.76 (3H, s, H-18), 0.96 (3H, s, H-19), 2.23 (1H, m, H-16a), 2.48 (1H, m, H-16b), 3.40 (2H, s, COCH$_2$CO), 4.62 (2H, m, =CH$_2$), 4.83 (1H, m, H-3). $^{13}$C NMR (101 MHz, CDCl$_3$): δ 169.29 (COOH), 167.84 (COO), 161.96 (C-17), 100.87 (C-20), 76.87 (C-3), 54.63, 44.34, 42.14, 40.93, 40.30, 36.01, 35.92, 35.15, 34.90, 32.13, 29.61, 27.06, 26.56, 26.38, 24.31, 23.44, 20.91, 18.67. IR spectrum (CHCl$_3$): 3510 (OH, COOH, monomer); 3120 (OH, COOH, dimer); 3069, 1654, 885 (=CH$_2$); 1778 (C=O, COOH, monomer); 1716 (C=O, COOH, monomer). MS (ESI) m/z: 397.3 (100%, M+Na), 771.6 (10%, 2M+Na). For C$_{23}$H$_{34}$O$_4$ (374.5) calcd: 73.76% C, 9.15% H; found: 72.74% C, 9.37% H.

Example 62: 4-(((3R,5R,8R,9S,10S,13S,14S)-10,13-Dimethyl-17-methylenehexadecahydro-1H-cyclopenta[a]phenanthren-3-yl)oxy)-4-oxobutanoic acid (68)

Compound 68 was prepared according to General Procedure II—Preparation of C-3 Hemisuccinate from compound 66 (200 mg, 0.69 mmol). Chromatography on silica gel (10% acetone in petroleum ether) gave compound 68 (265 mg, 99%) as a solid foam: $[\alpha]_D^{20}$ +54.5 (c 0.30, CHCl$_3$). $^1$H NMR (400 MHz, CDCl$_3$): δ 0.76 (3H, s, H-18), 0.94 (3H, s, H-19), 2.23 (1H, m, H-16a), 2.47 (1H, m, H-16b), 2.56-2.68 (4H, m, OCCH$_2$CH$_2$CO), 4.61 (2H, m, =CH$_2$), 4.74 (1H, m, H-3). $^{13}$C NMR (101 MHz, CDCl$_3$): δ 177.61 (COOH), 171.81 (COO), 162.03 (C-17), 100.82 (C-20), 75.09 (C-3), 54.66, 44.35, 42.15, 40.91, 36.04, 35.94, 35.25, 34.91, 32.32, 29.62, 29.44, 29.11, 27.11, 26.71, 26.41, 24.32, 23.48, 20.90, 18.67. IR spectrum (CHCl$_3$): 3516 (COOH, monomer), 3100 (COOH, dimer), 1754 (C=O, COOH, monomer), 1717 (C=O, COOH, dimer). MS (ESI) m/z: 411.2 (100%, M+Na). For C$_{24}$H$_{36}$O$_4$ (388.5) calcd: 74.19% C, 9.34% H; found: 73.97% C, 9.38% H.

Example 63: 5-(((3R,5R,8R,9S,10S,13S,14S)-10,13-Dimethyl-17-methylenehexadecahydro-1H-cyclopenta[a]phenanthren-3-yl)oxy)-5-oxopentanoic acid (69)

Compound 69 was prepared according to General Procedure IV—Preparation of C-3 Hemiglutarate from compound 66 (200 mg, 0.6 mmol). Chromatography on silica gel (10% ether in petroleum ether) gave a white solid which crystallized from acetone/water gave desired hemiester 69 (134 mg, 53%): mp 84-86° C., $[\alpha]_D^{20}$ +52.3 (c 0.17, CHCl$_3$). $^1$H NMR (400 MHz, CDCl$_3$): δ 0.76 (3H, s, H-18), 0.95 (3H, s, H-19), 2.16-2.28 (2H, m, H-16a, H-16b), 2.35-2.43 (4H, m, glutaric acid), 4.58-4.65 (2H, m, =CH$_2$), 4.74 (1H, tt, J$_1$=11.3, J$_2$=4.7, H-3). $^{13}$C NMR (101 MHz, CDCl$_3$): δ 178.33 (COOH), 172.38 (COO), 161.87 (C-17), 100.66 (C-20), 74.48 (C-3), 54.49, 44.19, 42.00, 40.75, 35.87, 35.78, 35.11, 34.76, 33.59, 32.90, 32.26, 29.46, 26.95, 26.64, 26.25, 24.16, 23.33, 20.74, 19.94, 18.51. IR spectrum (CHCl$_3$): 3517 (OH, COOH, monomer); 3069, 1654 (=CH$_2$); 2675 (OH, COOH, dimer); 1756 (C=O, COOH, monomer); 1713 (C=O, COOH, dimer); 1722 (C=O, ester). MS (ESI) m/z: 425.2 (100%, M+Na). HR-MS (ESI) m/z: For C$_{25}$H$_{38}$O$_4$Na (M+Na) calcd: 425.2662; found: 425.2662. For C$_{25}$H$_{38}$O$_4$ (402.6) calcd: 74.59% C, 9.51% H; found: 74.31% C, 9.82% H.

Example 64: 6-(((3R,5R,8R,9S,10S,13S,14S)-10,13-Dimethyl-17-methylenehexadecahydro-1H-cyclopenta[a]phenanthren-3-yl)oxy)-6-oxohexanoic acid (70)

Dicyclohexylcarbodiimide (154 mg, 0.74 mmol) in dried benzene (6 ml) was added to a solution of adipic acid (120 mg, 0.82 mmol) in dried tetrahydrofurane (6 ml) under inert atmosphere and the mixture was stirred at room temperature for 1.5 h. Then, a solution of hydroxy derivative 66 (120 mg, 0.41 mmol) and 4-(N,N-dimethylamino)pyridine (7 mg, 0.05 mmol) in dried benzene (7 ml) was added dropwise over 15 minutes. The reaction mixture was stirred overnight at room temperature. The solids were filtered off, the solvent evaporated under reduced pressure and the residue purified on silica gel (10% acetone in petroleum ether) affording hemiester 70 (80 mg, 46%): mp 100-102° C. (acetone/water), $[\alpha]_D^{20}$ +42.5 (c 0.22, CHCl$_3$). $^1$H NMR (400 MHz, CDCl$_3$): δ 0.76 (3H, s, H-18), 0.95 (3H, s, H-19), 2.18-2.51 (6H, m, H$_a$-16, H$_b$-16, adipic acid), 4.61 (2H, m, =CH$_2$), 4.73 (1H, m, H-3). $^{13}$C NMR (101 MHz, CDCl$_3$): δ 178.35 (COOH), 172.98 (COO), 162.06 (C-17), 100.81 (C-20), 74.46 (C-3), 54.65, 44.35, 42.15, 40.90, 36.04, 35.94, 35.28, 34.92, 34.45, 33.60, 32.43, 29.62, 27.12, 26.81, 26.42, 24.56, 24.32, 24.25, 23.50, 20.90, 18.67. IR spectrum (CHCl$_3$): 3517 (OH, COOH, monomer); 3069, 1654 (=CH$_2$); 2675 (OH, COOH, dimer); 1755 (C=O, COOH, monomer); 1712 (C=O, COOH, dimer); 1724 (C=O, ester). MS (ESI) m/z: 439.2 (100%, M+Na), 855.5 (5%, 2M+Na). HR-MS (ESI) m/z: For C$_{26}$H$_{40}$ONa (M+Na) calcd: 439.2818; found: 439.2817.

Example 65: Ethyl (E)-2-((5R,8R,9S,10S,13S,14S)-10,13-dimethyl-17-oxohexadecahydro-3H-cyclopenta[a]phenanthren-3-yliden)-acetate and Ethyl (Z)-2-((5R,8R,9S,10S,13S,14S)-10,13-dimethyl-17-oxohexadecahydro-3H-cyclopenta[a]phenanthren-3-yliden)-acetate (mixture of isomers, 72)

Triethyl 2-phosphonoacetate (20.4 ml, 103 mmol) was added dropwise to a suspension of sodium hydride (60% dispersion in parafin oil, 3.9 g, 98 mmol) in anhydrous tetrahydrofuran (100 ml) at 0° C. under inert atmosphere. Hydrogen gas released, the heterogeneous reaction mixture became clear and was stirred for 30 min. Then, 5beta-androstan-3,17-dione 71 (14.9 g, 51.6 mmol) in anhydrous tetrahydrofuran (40 ml) was added dropwise. The reaction mixture was stirred for 2 h at 0° C. under inert atmosphere, then poured into saturated sodium chloride (200 ml) and the product extracted into ethyl acetate (3×150 ml). The combined organic extracts were washed with water, dried over anhydrous sodium sulfate and the solvents evaporated under reduced pressure. Chromatography of the residue on silica gel (15% ethyl acetate in petroleum ether) gave an oily mixture of E- and Z-isomers of 72 (1:1 ratio by NMR, 18.5 g, 99%): $^1$H NMR (400 MHz, CDCl$_3$): δ 0.85 (6H, s, H-18), 0.95 (6H, s, H-19), 1.23-1.27 (6H, m, OCH$_2$CH$_3$), 2.30 (1H, t, J=13.7, H-4α, Z-isomer), 2.40-2.47 (2H, m, H-16), 2.64 (1H, t, J=13.4, H-4α, E-isomer), 3.47 (1H, ddd, J$_1$=14.5, J$_2$=3.9, J$_3$=1.6, H-4β, Z-isomer), 3.55-3.61 (1H, m, H-2β), 4.08-4.15 (4H, m, OCH$_2$CH$_3$), 5.58 (1H, m, =CH, E-isomer), 5.60 (1H, m, =CH, Z-isomer). $^{13}$C NMR (101 MHz, CDCl$_3$): δ 221.25, 221.16, 167.05, 166.85, 164.25, 164.05, 113.08, 113.05, 59.59, 51.66, 47.99, 45.70, 44.89, 41.15, 41.07, 38.67, 38.29, 38.18, 36.04, 35.63, 35.48, 32.80, 31.90, 30.35, 26.99, 26.84, 25.28, 24.80, 23.37, 23.25, 21.94, 20.52, 20.45, 14.46, 13.95.

Example 66: 2-((3R,5R,8R,9S,10S,13S,14S)-10,13-Dimethyl-17-oxohexadecahydro-1H-cyclopenta[a]phenanthren-3-yl)acetic acid (74)

Substance 73 was prepared according to General Procedure V—Catalytic Hydrogenation from compound 72 (18.5 g, 51.6 mmol). The crude oily mixture of 3alpha/3beta-isomer 73 (18.5 g, 99%), which could not be crystallized or partially separated was therefore used for the next reaction step. A solution of potassium hydroxide (1.8 g, 33 mmol) in water (5 ml) and ethanol (40 ml) was added to 73 (2 g, 5.54 mmol). The reaction mixture was heated at 85° C. for 1 h. The progress of the reaction was monitored by thin layer chromatography. After disappearance of the starting material, the reaction mixture was poured into crushed ice and water, acidified with dilute hydrochloric acid (HCl/H$_2$O, 1:2) to pH-1. The product was extracted with chloroform (3×50 ml); the combined organic extracts were washed with water, dried over anhydrous sodium sulfate and the solvents evaporated under reduced pressure. The crude product (1.88 g) by repeated crystallization from ethanol gave pure 3α-isomer 74 (133 mg, 7%): mp 130-133° C. (ethanol), $[α]_D^{20}$ +96.5 (c 0.25, CHCl$_3$). $^1$H NMR (400 MHz, CDCl$_3$): δ 0.84 (3H, s, H-18), 0.95 (3H, s, H-19), 2.25 (2H, dd, J$_1$=7.1, J$_2$=3.0, CH$_2$COOH), 2.44 (1H, m, H-16). $^{13}$C NMR (101 MHz, CDCl$_3$): δ 221.59 (C-17), 177.85 (COOH), 51.69, 48.04, 43.33, 41.74, 41.05, 37.12, 36.10, 35.61 (2×C), 35.22, 33.62, 31.92, 27.71, 27.14, 25.55, 23.95, 21.98, 20.26, 13.96. IR spectrum (CHCl$_3$): 3518 (COOH, monomer); 3091 (COOH, dimer); 1731 (C=O, COOH, monomer); 1706 (C=O, COOH, dimer); 1706 (C=O). MS (ESI) m/z: 355.3 (100%, M+Na), 687.6 (20%, 2M+Na). For C$_{21}$H$_{32}$O$_3$ (332.3) calcd: 75.86% C, 9.70% H; found: 75.89% C, 9.57% H.

Example 67: 7-(((3R,5R,8R,9S,10S,13S,14S)-10,13-Dimethyl-17-methylenehexadecahydro-1H-cyclopenta[a]phenanthren-3-yl)oxy)-7-oxoheptanoic acid (75)

Compound 75 was prepared according to the General Procedure VII—Wittig Reaction Using n-butyl lithium from compound 74 (130 mg, 039 mmol). Chromatography on silica gel (10% ethyl acetate in petroleum ether) recovered starting material 74 (55 mg) and the desired methylene derivative 75 (50 mg, 38%): mp 155-159° C. (acetone), $[α]_D^{20}$ +30.4 (c 0.15, CHCl$_3$). $^1$H NMR (400 MHz, CDCl$_3$): δ 0.76 (3H, s, H-18), 0.95 (3H, s, H-19), 2.17-2.25 (3H, m, H-16a, CH$_2$COOH), 2.47 (1H, m, H-16b), 4.61 (2H, d, J=6.8, =CH$_2$). $^{13}$C NMR (101 MHz, CDCl$_3$): δ 178.11 (COOH), 162.22 (C-17), 100.74 (C-20), 54.72, 44.37, 43.46, 41.83, 41.03, 37.20, 36.09, 35.99, 35.68, 35.19, 33.70, 29.64, 27.76, 27.37, 26.53, 24.33, 24.05, 20.89, 18.69. IR spectrum (CHCl$_3$): 3518 (COOH, monomer); 3090 (COOH, dimer); 1733 (C=O, COOH, monomer); 1706 (C=O, COOH, dimer); 3069, 1653 (=CH$_2$). MS (ESI) in/z: 329.2 (100%, M–H), 659.5 (20%, 2M–H). For C$_{22}$H$_{34}$O$_2$ (330.5) calcd: 79.95% C, 10.37% H; found: 79.66% C, 10.41% H.

Example 68: 2-(((3R,5R,8R,9S,10S,13S,14S)-10,13-Dimethyl-17-methylenehexadecahydro-1H-cyclopenta[a]phenanthren-3-yl)oxy)-N,N,N-trimethyl-2-oxoethan-1-ammonium chloride (76)

To a solution of betaine (trimethyl glycine, dried overnight at 50° C., 255 mg, 1.6 mmol) in dried dichloromethane was added oxalic acid chloride (2.06 ml, 24 mmol) and N,N'-dimethylformamide (4 drops). The reaction mixture was stirred at room temperature overnight. Then, the solvents were evaporated under reduced pressure and the residue was treated with dried nitromethane (6 ml), dried pyridine (0.3 ml) and the hydroxy derivative 66 (160 mg, 0.55 mmol). The reaction mixture was stirred at room temperature overnight and then, it was poured into water and acidified with dilute hydrochloric acid (5%) to pH-4. The product was extracted into benzene. The benzene extract was dried over anhydrous magnesium sulfate and the solvent evaporated under reduced pressure. Twofold crystallization (chloroform/n-heptane) afforded quaternary ammonium salt 76 (136 mg, 57%): mp 175-177° C., $[α]_D^{20}$ +43.3 (c 0.24, CHCl$_3$). $^1$H NMR (400 MHz, CD$_3$OD): δ 0.76 (3H, s, H-18), 0.95 (3H, s, H-19), 3.65 (9H, br s, N(CH$_3$)$_3$), 4.62 (2H, d, J$_1$=7.3, =CH$_2$), 4.80 (1H, tt, J$_1$=11.1, J$_2$=4.6, H-3), 4.88 (1H, s, H-2'). $^{13}$C NMR (101 MHz, CDCl$_3$): δ 164.39, 161.84, 102.93, 100.91, 78.00, 63.48, 54.41, 44.31, 42.18, 40.86, 35.90, 35.10, 34.87, 32.16, 29.60, 27.03, 26.57, 26.30, 24.30, 23.39, 20.90, 18.68. IR spectrum (CHCl$_3$): 3070, 1654, 1416 (C=CH$_2$); 2960 (N(CH$_3$)$_3$); 1743 (C=O); 1258 (C—O). MS (ESI) m/z: 388.3 (100%, M–Cl), 389.3 (30%, M–Cl+1). HR-MS (ESI) m/z: For C$_{25}$H$_{42}$NO$_2$ (M–Cl) calcd: 388.3210, found: 388.3209.

Example 69: (3R,5R,8S,9S,10S,13R,14S,17S)-10,13,17-Trimethylhexadecahydro-1H-cyclopenta[a]phenanthren-3-ol (77)

Compound 77 was prepared according to General Procedure V—Catalytic Hydrogenation from compound 66 (100 mg, 0.34 mmol). Crystallization from acetone/n-heptane gave methyl derivative 77 (75 mg, 75%): mp 151-153° C. (acetone/n-heptane), $[α]_D^{20}$ +18.1 (c 0.21, CHCl$_3$). $^1$H NMR (400 MHz, CDCl$_3$): δ 0.52 (3H, s, H-18), 0.82 (3H, d, J=6.8, 17-Me), 0.92 (3H, s, H-19), 3.62 (1H, m, H-3). $^{13}$C NMR (101 MHz, CDCl$_3$): δ 72.06 (C-3), 56.04, 45.31, 42.41, 42.34, 41.05, 37.91, 36.70, 36.28, 35.66, 34.90, 30.75, 30.43, 27.40, 26.81, 24.92, 23.58, 20.76, 13.97, 12.17. IR spectrum (CHCl$_3$): 3610, 1034 (OH); 1379 (methyl). MS (ESI) m/z: 313.2 (100%, M+Na). For C$_{20}$H$_{34}$O (290.5) calcd: 82.69% C, 11.80% H; found: 82.62% C, 11.37% H.

Example 70: 3-Oxo-3-(((3R,5R,8S,9S,10S,13R,14S,17S)-10,13,17-trimethylhexadecahydro-1H-cyclopenta[a]phenanthren-3-yl)oxy)propanoic acid (78)

Compound 78 was prepared by the General Procedure III—Preparation of C-3 Hemimalonate from compound 77

(151 mg, 0.52 mmol). Chromatography on silica gel (10-20% ethyl acetate in petroleum ether) gave compound 78 (162 mg, 82%): mp 158-161.2° C. (acetone/n-heptane), $[\alpha]_D^{20}$ +36.9 (c 0.31, CHCl$_3$). $^1$H NMR (400 MHz, CDCl$_3$): δ 0.53 (3H, s, H-18), 0.82 (3H, d, J=6.8, 17-methyl), 0.95 (3H, s, H-19), 3.36-3.47 (2H, m, OCCH$_2$CO), 4.79-4.89 (1H, m, H-3). $^{13}$C NMR (101 MHz, CDCl$_3$): δ 168.80 (COOH), 168.08 (COO), 77.05 (C-3), 55.96, 45.32, 42.34, 42.19, 41.04, 40.15, 37.84, 36.20, 35.19, 34.18, 32.18, 30.40, 27.16, 26.67, 26.59, 24.88, 23.49, 20.77, 13.98, 12.18. IR spectrum (CHCl$_3$): 3511 (OH, COOH, monomer); 1760 (C=O, COOH, monomer); 1720 (C=O, COOH, dimer); 1386 (methyl). MS (ESI) m/z: 399.4 (100%, M+Na). HR-MS (ESI) m/z: For C$_{23}$H$_{36}$O$_4$Na (M+Na) calcd: 399.2506; found: 399.2506.

Example 71: 4-Oxo-4-(((3R,5R,8S,9S,10S,13R,14S,17S)-10,13,17-trimethylhexadecahydro-1H-cyclopenta[a]phenanthren-3-yl)oxy)butanoic acid (79)

Compound 79 was prepared according to General Procedure II—Preparation of C-3 Hemisuccinate from compound 77 (200 mg, 0.69 mmol). Chromatography on silica gel (10-20% ethyl acetate in petroleum ether) gave hemiester 79 (123 mg, 89%): mp 141-142° C. (aceton/n-heptane), $[\alpha]_D^{20}$ +34.4 (c 0.27, CHCl$_3$). $^1$H NMR (400 MHz, CDCl$_3$): δ 0.51 (3H, s, H-18), 0.81 (3H, d, J=6.8, 17-methyl), 0.92 (3H, s, H-19), 2.55-2.66 (4H, m, OCCH$_2$CH$_2$CO), 4.73 (1H, m, H-3). $^{13}$C NMR (101 MHz, CDCl$_3$): δ 175.34 (COOH), 172.03 (COO), 74.98 (C-3), 55.94, 45.29, 42.31, 42.17, 40.97, 37.83, 36.18, 35.29, 34.89, 32.36, 30.38, 29.65, 29.13, 27.19, 26.73, 26.68, 24.87, 23.51, 20.73, 13.97, 12.15. IR spectrum (CHCl$_3$): 3515 (OH, COOH, monomer), 3086 (OH, COOH, dimer), 1755 (C=O, COOH, monomer), 1725 (C=O), 1717 (C=O, COOH, dimer), 1381 (methyl). MS (ESI) m/z: 389.3 (100%, M−H). For C$_{24}$H$_{38}$O$_4$ (390.5) calcd: 73.81% C, 9.81% H; found: 73.76% C, 9.68% H.

Example 72: 5-Oxo-5-(((3R,5R,8S,9S,10S,13R,14S,17S)-10,13,17-trimethylhexadekahydro-1H-cyklopenta[a]phenanthren-3-yl)oxy)pentanoic acid (80)

Compound 80 was prepared according to General Procedure IV—Preparation of C-3 Hemiglutarate from compound 77 (200 mg, 0.69 mmol). Chromatography on silica gel (20-30% ethyl acetate in petroleum ether) gave compound 80 (135 mg, 96%): mp 151-152° C. (acetone/n-heptane), $[\alpha]_D^{20}$ +31.9 (c 0.27, CHCl$_3$). $^1$H NMR (400 MHz, CDCl$_3$): δ 0.52 (3H, s, H-18), 0.82 (3H, d, J=6.8, 17-methyl), 0.93 (3H, s, H-19), 1.96 (2H, p, J=7.3, H-3'), 2.37 (2H, t, J=7.3, H-2'), 2.43 (2H, t, J=7.3, H-4'), 4.74 (1H, m, H-3). $^{13}$C NMR (101 MHz, CDCl$_3$): δ 177.67 (COOH), 172.52 (COO), 74.74 (C-3), 55.98, 45.32, 42.34, 42.20, 41.01, 37.86, 36.21, 35.32, 34.92, 33.77, 32.92, 32.47, 30.41, 27.21, 26.83, 26.70, 24.90, 23.54, 20.76, 20.12, 13.99, 12.18. IR spectrum (CHCl$_3$): 3516 (OH, COOH, monomer); 3089 (OH, COOH, dimer); 1755 (C=O, COOH, monomer); 1723 (C=O); 1713 (C=O, COOH, dimer); 1380 (methyl). MS (ESI) m/z: 403.3 (100%, M−H). For C$_{25}$H$_{40}$O$_4$ (404.5) calcd: 74.22% C, 9.97% H; found: 74.08% C, 9.81% H.

Example 73: (4S)-4-Amino-5-oxo-5-(((3R,5R,8S,9S,10S,13R,14S,17S)-10,13,17-trimethylhexadecahydro-1H-cyclopenta[a]phenanthren-3-yl)oxy)pentanoic acid (81)

To a stirred mixture of alcohol 77 (500 mg, 1.72 mmol) and Boc-Glu(OBzl)-OH (640 mg, 1.90 mmol) in freshly dried benzene (35 ml) were added 4-(N,N-dimethylamino) pyridine (21 mg, 0.172 mmol) and dicyclohexylcarbodiimide (1M solution in benzene, 2.5 ml) under inert atmosphere at room temperature. After 18 h, the reaction mixture was poured into saturated sodium bicarbonate solution (40 ml), the product was extracted into ethyl acetate (3×30 ml), and the combined organic phases were washed with water (2×10 ml). The precipitated N,N'-dicyclohexylurea was filtered off, the filtrate was dried over anhydrous sodium sulfate and the solvents evaporated under reduced pressure. Further portions of N,N'-dicyclohexylurea was crystallised from ether and flittered off. The filtrate containing the desired product was evaporated under reduced pressure. Chromatography of the residue on silica gel (10% ethyl acetate in petroleum ether) gave solid white foam of protected glutamate (960 mg, 91%). The product was characterized by NMR and used crude for the next step. $^1$H NMR (400 MHz, CDCl$_3$): δ 0.53 (3H, s, H-18), 0.83 (3H, d, J=6.8, H-20), 0.94 (3H, s, H-19), 1.43 (9H, s, t-Bu), 2.26-2.43 (2H, m, H-4'), 4.32-4.41 (1H, m, CH-2'), 4.72 (1H, tt, J$_1$=11.3, J$_2$=4.7, H-3), 5.17 (2H, d, J=5.1, CH$_2$-benzyl), 7.34-7.38 (5H, m, phenyl). $^{13}$C NMR (101 MHz, CDCl$_3$): δ 172.41 (C-1'), 172.37 (C-5'), 155.50 (OCONH), 135.48 (C-1', phenyl), 128.74 (C-3', C-5', phenyl), 128.54 (C-4', phenyl), 128.35 (C-2', C-6', phenyl), 80.15 (t-Bu), 74.93 (C-3), 67.32, 55.99, 53.30, 45.32, 42.34, 42.19, 41.01, 37.86, 36.21, 35.30, 34.90, 32.38, 30.91, 30.41, 28.46 (3×C, t-Bu), 27.87, 27.20, 26.78, 26.69, 24.88, 23.53, 20.76, 13.98, 12.17.

To a solution of the protected ester of glutamic acid (950 mg, 1.56 mmol) in absolute methanol (55 ml) was added palladium catalyst on charcoal (10%, 50 mg). The reaction mixture was stirred at room temperature under vigorous stirring and a slight positive pressure of hydrogen for 2 h. The catalyst was filtered off and the solvents evaporated under reduced pressure. The residue was dissolved in dichloromethane (8 ml) and stirring was dropwise added trifluoracetic acid (5 ml). The reaction mixture was stirred at room temperature for 30 min and then evaporated under reduced pressure to dryness. To the residue was added a mixture of methanol (10 ml) and pyridine (1 ml) and the solution was dropwise added into water (60 ml) with crushed ice. The whole mixture was kept overnight at 5° C. The solids were collected by filtration, washed with water and dried to afford the monoester 81 (541 mg, 67%, two steps): mp 169-171° C. (methanol), $[\alpha]_D^{20}$ +52.5 (c 0.099, CHCl$_3$/MeOH, 1.7:0.8). $^1$H NMR (400 MHz, CDCl$_3$/CD$_3$OD, 6:1): δ 0.48 (3H, s, H-18), 0.78 (3H, d, J=6.7, H-20), 0.90 (3H, s, H-19), 2.42-2.55 (2H, m, H-4'), 3.52-3.61 (1H, m, CH-2'), 4.60-4.72 (1H, m, H-3). $^{13}$C NMR (101 MHz, CDCl$_3$/CD$_3$OD, 6:1): δ 173.36 (COOH, COO), 75.22 (C-3), 55.86, 55.83, 45.23, 42.25, 42.17, 40.95, 37.76, 36.14, 35.25, 34.83, 32.31, 31.16, 3032, 29.76, 27.19, 26.65, 26.57, 24.81, 23.47, 20.70, 13.86, 12.05. IR spectrum (KBr): 2717, 1540, 1491 (NH$_3^+$); 1745, 1718 (C=O, glutamyl ester); 1732 (CO); 1635 (COO$^-$); 1022 (COC). MS (ESI) m/z: 442.3 (100%, M+Na), 420.4 (45%, M+H). HR-MS (ESI) m/z: For C$_{25}$H$_{42}$O$_4$N (M+H) calcd: 420.3108; found: 420.3108.

Example 74: 3-(((3R,5R,8R,9S,10S,13S,14S,Z)-17-Ethylidene-10,13-dimethylhexadecahydro-1H-cyclopenta[a]phenanthren-3-ol (82)

Hydroxyderivative 82 was prepared according to the literature (Chem. Pharm. Bull., 31, 3819-3828, (1983)).

Example 75: 3-(((3R,5R,8R,9S,10S,13S,14S,Z)-17-Ethylidene-10,13-dimethylhexadecahydro-1H-cyclopenta[a]phenanthren-3-yl)oxy)-3-oxopropanoic acid (83)

Compound 83 was prepared according to General Procedure III—Preparation of C-3 Hemimalonate from compound 82 (200 mg, 0.66 mmol). Chromatography on silica gel (1-10% acetone in petroleum ether) gave compound 83 (239 mg, 92%): mp 126-128° C. (acetone/petroleum ether), $[\alpha]_D^{20}$ +24.0 (c 0.55, CHCl$_3$). $^1$H NMR (400 MHz, CDCl$_3$): δ 0.86 (3H, s, H-18), 0.95 (3H, s, H-19), 1.64 (3H, dt, J$_1$=7.1, J$_2$=2.0, H-21), 3.41 (1H, s, H-2'), 4.84 (1H, m, H-3), 5.12 (1H, qt, J$_1$=7.2, J$_2$=2.1, H-20). $^{13}$C NMR (101 MHz, CDCl$_3$): δ 179.31 (COOH), 171.59 (COO), 150.42 (C-17), 113.45 (C-20), 76.94 (C-3), 56.42, 44.59, 41.87, 40.60, 37.50, 35.49, 35.05, 34.80, 32.13, 31.64, 29.03, 27.09, 26.58, 26.33, 24.54, 23.39, 21.19, 17.03, 13.25. IR spectrum (CHCl$_3$): 3516 (COOH, monomer), 3114 (COOH, dimer), 1751 (C=O, COOH, monomer), 1726 (C=O), 1717 (C=O, COOH, dimer). MS (ESI) m/z: 425.3 (100%, M+Na). For C$_{25}$H$_{38}$O$_4$ (402.5) calcd: 74.59% C, 9.51% H; found: 74.68% C, 9.42% H.

Example 76: 4-(((3R,5R,8R,9S,10S,13S,14S,Z)-17-Ethylidene-10,13-dimethylhexadecahydro-1H-cyclopenta[a]phenanthren-3-yl)oxy)-4-oxobutanoic acid (84)

Compound 84 was prepared according to General Procedure II—Preparation of C-3 Hemisuccinate from compound 82 (200 mg, 0.66 mmol). Chromatography on silica gel (3-20% acetone in petroleum ether) gave hemiester 84 (250 mg, 94%): mp 152-154° C. (acetone/petroleum ether), $[\alpha]_D^{20}$ +58.1 (c 0.21, CHCl$_3$). $^1$H NMR (400 MHz, CDCl$_3$): δ 0.85 (3H, s, H-18), 0.93 (3H, s, H-19), 1.65 (3H, dt, J$_1$=7.1, J$_2$=1.9, H-21), 2.57-2.69 (4H, m, OCCH$_2$CH$_2$CO), 4.75 (1H, m, H-3), 5.11 (1H, qt, J$_1$=7.1, J$_2$=2.0, H-20). $^{13}$C NMR (101 MHz, CDCl$_3$): δ 177.07 (COOK 171.83 (COO), 150.50 (C-17), 113.40 (C-20), 75.13 (C-3), 56.45, 44.59, 42.07, 40.70, 37.54, 35.52, 35.16, 34.82, 32.32, 31.66, 29.46, 29.03, 27.14, 26.74, 26.36, 24.56, 23.44, 21.19, 17.03, 13.25. IR spectrum (CHCl$_3$): 3516 (COOH, monomer), 3114 (COOH, dimer), 1751 (C=O, COOH, monomer), 1726 (C=O), 1717 (C=O, COOH, dimer). MS (ESI) m/z: 425.3 (100%, M+Na). For C$_{25}$H$_{38}$O$_4$ (402.5) calcd: 74.59% C, 9.51% H; found: 74.68% C, 9.42% H.

Example 77: 5-(((3R,5R,8R,9S,10S,13S,14S,Z)-17-Ethylidene-10,13-dimethylhexadecahydro-1H-cyclopenta[a]phenanthren-3-yl)oxy)-5-oxopentanoic acid (85)

Compound 85 was prepared according to General Procedure IV—preparation of C-3 Hemiglutarate from compound 82 (150 mg, 0.49 mmol). Chromatography on silica gel (5-20% acetone in petroleum ether) gave compound 85 (178 mg, 86%): mp 100-103° C. (acetone), $[\alpha]_D^{20}$ +57.3 (c 0.39, CHCl$_3$). $^1$H NMR (400 MHz, CDCl$_3$): δ 0.85 (3H, s, H-18), 0.93 (3H, s, H-19), 1.64 (3H, dt, J$_1$=7.1, J$_2$=1.9, H-21), 2.34-2.44 (4H, m, hemiglutarate), 4.74 (1H, m, H-3), 5.11 (1H, qt, J$_1$=7.0, J$_2$=1.9, H-20). $^{13}$C NMR (101 MHz, CDCl$_3$): δ 178.19 (COOH), 172.55 (COO), 150.50 (C-17), 113.39 (C-20), 74.67 (C-3), 56.44, 44.59, 42.08, 40.69, 37.53, 35.51, 35.17, 34.82, 33.77, 33.04, 32.41, 31.66, 27.14, 26.82, 26.36, 24.55, 23.44, 21.19, 20.12, 17.03, 13.25. IR spectrum (CHCl$_3$): 3517 (OH, COOH, monomer), 3116 (COOH, dimer), 1747 (C=O, COOH, monomer), 1722 (C=O), 1713 (C=O, COOH, dimer). MS (ESI) m/z: 439.2 (100%, M+Na), 855.5 (5%, 2M+Na). For C$_{26}$H$_{40}$O$_4$ (416.6) calcd: 74.96% C, 9.68% H; found: 74.77% C, 9.72% H.

Example 78: (3R,5R,8R,9S,10S,13S,14S,17R)-10,13-Dimethyl-17-(prop-1-en-2-yl)hexadecahydro-1H-cyclopenta[a]phenanthren-3-ol (87)

Compound 87 was prepared according to the General Procedure VII—Wittig Reaction Using n-Butyl Lithium from 3alpha,5beta-pregnan-20-one 86 (1 g, 3.13 mmol). Chromatography on silica gel (10% ethyl acetate in petroleum ether) gave compound 87 (760 mg, 76%): mp 149-151° C. (acetone/n-heptane), $[\alpha]_D^2$+16.6 (c 0.39, CHCl$_3$). $^1$H NMR (400 MHz, CDCl$_3$): δ 0.54 (3H, s, H-18), 0.91 (3H, s, H-19), 1.75 (3H, s, H-21), 2.02 (1H, t, J=9.1, H-17), 3.62 (1H, m, H-3), 4.69 (1H, s, H-22a), 4.83 (1H, s, H-22b). $^{13}$C NMR (101 MHz, CDCl$_3$): δ 145.86 (C-20), 110.78 (=CH$_2$), 71.99 (C-3), 57.57 (C-17), 56.49 (C-14), 43.58, 4231, 40.83, 39.25, 36.65, 36.39, 35.56, 34.80, 30.72, 27.34, 26.57, 25.67, 24.78, 24.36, 23.54, 21.04, 13.00. IR spectrum (CHCl$_3$): 3609, 3447, 1033 (OH); 3085, 1639 (=CH$_2$); 1376 (methyl). MS (ESI) m/z: 339.2 (100%, M+Na). For C$_{22}$H$_{36}$O (316.5) calcd: 83.48% C, 11.46% H; found: 83.49% C, 11.55% H.

Example 79: 3-(((3R,5R,8R,9S,10S,13S,14S,17R)-10,13-Dimethyl-17-(prop-1-en-2-yl)hexadecahydro-4H-cyclopenta[a]phenanthren-3-yl)oxy)-3-oxopropanoic acid (88)

Compound 88 was prepared according to the General Procedure VIII—Preparation of C-3 Hemimalonate from compound 87 (1 g, 3.13 mmol). Chromatography on silica gel (10% ethyl acetate in petroleum ether) gave compound 88 (760 mg, 76%): mp 147.7-148.3° C. (acetone/n-heptane), $[\alpha]_D^2$+37.9 (c 0.23, CHCl$_3$). $^1$H NMR (400 MHz, CDCl$_3$): δ 0.55 (3H, s, H-18), 0.94 (3H, s, H-19), 1.75 (3H, s, H-21), 2.03 (1H, t, J=9.2, H-17), 3.36-3.47 (2H, m, OCCH$_2$CO), 4.70 (1H, s, =CH$_2$), 4.79-4.91 (2H, m, H-3, =CH$_2$). $^{13}$C NMR (101 MHz, CDCl$_3$): δ 168.86 (COOH), 168.03 (COO), 145.84 (C-20), 110.88 (=CH$_2$), 76.98 (C-3), 57.57 (C-17), 56.44 (C-14), 43.59, 42.11, 40.83, 40.20, 39.18, 36.32, 35.11, 34.81, 32.15, 27.11, 26.58, 26.44, 25.65, 24.80, 24.33, 23.46, 21.06, 13.02. IR spectrum (CHCl$_3$): 3599 (OH, COOH, monomer), 3128 (OH, COOH, dimer), 1761 (C=O, COOH, monomer), 1718 (C=O, COOH, dimer), 1638 (=CH$_2$). MS (ESI) m/z: 425.3 (100%, M+Na). HR-MS (ESI) m/z: For C$_{25}$H$_{38}$O$_4$Na (M+Na) calcd: 425.2662; found: 420.2700. For C$_{25}$H$_{38}$O$_4$ (402.3) calcd: 74.59% C, 9.51% H; found: 74.32% C, 9.43% H.

Example 80: 4-(((3R,5R,8R,9S,10S,13S,14S,17R)-10,13-Dimethyl-17-(prop-1-en-2-yl)hexadecahydro-1H-cyclopenta[a]phenanthren-3-yl)oxy)-4-oxobutanoic acid (89)

Compound 89 was prepared according to General Procedure II—Preparation of C-3 Hemisuccinate from compound 87 (200 mg, 0.66 mmol). Chromatography on silica gel (20-30% ethyl acetate in petroleum ether) gave compound 89 (323 mg, 96%): mp 148-149.5° C. (acetone/n-heptane), $[\alpha]_D^{20}$ +42.5 (c 0.30, CHCl$_3$). $^1$H NMR (400 MHz, CDCl$_3$): δ 0.54 (3H, s, H-18), 0.93 (3H, s, H-19), 1.75 (3H, s, H-21), 2.03 (1H, t, J=9.2, H-17), 2.54-2.73 (4H, m, OCCH$_2$CH$_2$CO), 4.67-4.79 (2H, m, H-3, =CH$_2$), 4.84 (1H, s, =CH$_2$). $^{13}$C NMR (101 MHz, CDCl$_3$): δ 177.32 (COOH), 171.80 (COO), 145.84 (C-20), 110.83 (=CH$_2$), 75.15 (C-3), 57.58 (C-17), 56.46 (C-14), 43.60, 42.11, 40.81, 39.20, 36.33, 35.21, 34.82, 32.34, 29.44, 29.06, 27.15, 26.73, 26.47, 25.66, 24.81, 24.35, 23.50, 21.05, 13.01. IR spectrum (CHCl$_3$): 3518 (OH, COOH, monomer), 3100 (OH, COOH, dimer), 1755 (C=O, COOH, monomer), 1718 (C=O, COOH, dimer), 1640 (=CH$_2$). MS (ESI) m/z: 415.2 (100%, M−H). For C$_{26}$H$_{40}$O$_4$ (416.6) calcd: 74.96% C, 9.68% H; found: 74.94% C, 9.65% H.

Example 81: 2-((3R,5R,8R,9S,10S,13S,14S,17R)-10,13-Dimethyl-17-(prop-1-en-2-yl)hexadecahydro-1H-cyclopenta[a]fenanthren-3-yl)acetic acid (91)

Compound 91 was prepared according to the General Procedure VII—Wittig Reaction Using n-Butyl Lithium from compound 90 (5beta-pregnan-20-one 3-acetatic acid, 202 mg, 0.56 mmol). Chromatography on silica gel (20% ether in petroleum ether) gave compound 91 (80 mg, 40%): mp 198-200° C. (acetone/n-heptane), [α]$_D^{20}$ +27.3 (c 0.17, CHCl$_3$). $^1$H NMR (400 MHz, CDCl$_3$): δ 0.55 (3H, s, H-18), 0.93 (3H, s, H-19), 2.26 (2H, d, J=7.9, H-2, acetic acid), 4.70 (1H, s, H$_{trans}$, =CH$_2$), 4.84 (1H, s, H$_{cis}$, =CH$_2$). $^{13}$C NMR (101 MHz, CDCl$_3$): δ 178.08 (COOH), 145.80 (C-20), 110.60 (C-21), 57.44, 56.37, 43.46, 43.25, 41.71, 40.78, 39.11, 36.00, 36.24, 35.54, 34.95, 33.55, 27.62, 27.26, 26.44, 25.52, 24.66, 24.21, 23.92, 20.89, 12.87. IR spectrum (CHCl$_3$): 3516 (OH, COOH, monomer); 3085 (=CH$_2$); 2684 (OH, COOH, dimer); 1753 (C=O, COOH, monomer); 1706 (COOH, dimer). MS (ESI) m/z: 481.2 (100%, M+Na). For C$_{24}$H$_{38}$O$_2$ (358.6) calcd: 80.39% C, 10.68% H; found: 80.44% C, 10.79% H.

Example 82: Pyridinium (3R,5R,8R,9S,10S,13S,14S,17S)-17-iodo-10,13-dimethylhexadecahydro-1H-cyclopenta[a]phenanthren-3-yl 3-sulfate (93)

Compound 93 was prepared according to General Procedure I—Preparation of C-3 Sulfate from compound 92 (3alpha-hydroxy-5beta-17beta-iodoandrostane, 255 mg, 0.63 mmol) affording sulfate 93 (298 mg, 72%): mp 118-120° C., [α]$_D^{20}$ +58.5 (c 0.39, CHCl$_3$/MeOH, (1.94:0.20). $^1$H NMR (400 MHz, CDCl$_3$): δ 0.79 (3H, s, H-18), 0.92 (3H, s, H-19), 3.76 (1H, t, J, 9.4, H-17α), 4.39 (1H, tt, J$_1$=11.0, J$_2$=5.0, H-3), 7.32 (2H, ddd, J$_1$=7.6, J$_2$=4.3, J$_3$=1.5, H-2' and H-4', pyridinium), 7.72 (1H, tt, J$_1$=7.7, J$_2$=1.8, H-3', pyridinium), 8.64 (2H, dt, J$_1$=4.6, J$_2$=1.7, H-1' and H-5', pyridinium). $^{13}$C NMR (101 MHz, CDCl$_3$) δ 149.64 (C-1' and C-5', pyridinium), 136.45 (C-3', pyridinium), 128.63 (C-2' and C-4', pyridinium), 78.88, 50.15, 46.46, 44.29, 42.33, 42.12, 40.61, 37.22, 35.55, 34.73, 34.43, 33.45, 27.92, 27.04, 26.47, 25.56, 23.19, 20.58, 17.03. IR spectrum (CHCl$_3$): 3434, 3608 (OH); 1385 (CH$_3$); 1027, 1034 (C—O). MS (ESI) m/z: 381.2 (100%, M−H-pyridine). FIR-MS (ESI) m/z: For C$_{19}$H$_{30}$O$_4$IS calcd: 481.0904; found: 481.0908.

Example 83: Pyridinium (3R,5R,8R,9S,10S,13S,14S)-17,17-difluoro-10,13-dimethylhexadecahydro-1H-cyclopenta[a]phenanthren-3-yl 3-sulfate (95)

Compound 95 was prepared according to General Procedure I—preparation of C-3 Sulfate from compound 94 (86 mg, 0.28 mmol) affording compound 95 (96 mg, 73%): mp 185-187° C., [α]$_D^{20}$ +12.5 (c 0.28, CHCl$_3$/MeOH, 1.97: 0.04). $^1$H NMR (400 MHz, CDCl$_3$): δ 0.84 (3H, s, H-19), 0.92 (3H, s, H-19), 4.46 (1H, tt, J$_1$=10.8, J$_2$=5.1, H-3), 8.09-7.99 (2H, m, H-2' and H-4', pyridinium), 8.44-8.51 (1H, m, H-3', pyridinium), 7.96-8.02 (2H, m, H-1' and H-5', pyridinium). $^{13}$C NMR (101 MHz, CDCl$_3$ and MeOH): δ 145.84 (C-1' and C-5', pyridinium), 142.42 (C-3', pyridinium), 127.27 (C-2' and C-4', pyridinium), 79.51, 58.64, 49.62, 42.23, 40.48, 35.72, 35.45, 34.70, 33.44, 33.09, 29.23, 27.87, 26.89, 25.69, 23.34, 22.44, 20.06, 18.56, 13.46. IR spectrum (CHCl$_3$): 1350, 1121 (CF$_2$); 1247, 1168, 973, 947 (OSO$_3$). MS (ESI) m/z: 391.2 (100%, M−1-pyridine). HR-MS (ESI) m/z: For C$_{19}$H$_{29}$F$_2$S calcd 391.1760; found 391.1757.

Example 84: (3R,5R,8R,9S,10S,13S,14S,17S)-10,13-Dimethylhexadecahydrospiro[cyclopenta[a]phenanthren-17,2'-oxiran]-3-ol (96)

Potassium tert-butoxide (267 mg, 2.38 mmol) and trimethylsulfonium iodide (486 mg, 2.38 mmol) were added all at once to a solution 5beta-androstan-3alpha-ol (47, 346 mg, 1.19 mmol) in dried N,N-dimethylformamide (6 ml) under inert atmosphere. The reaction mixture was stirred at room temperature overnight. Then, a saturated aqueous sodium chloride solution was added and the product was extracted with chloroform (3×30 ml). The combined organic extracts were dried over anhydrous sodium sulfate and the solvents evaporated under reduced pressure. The residue was purified by column chromatography (0-15% ethyl acetate in petroleum ether) giving compound 96 (284 mg, 78%): mp 149-150° C. (ether/petroleum ether). $^1$H NMR (400 MHz, CDCl$_3$): δ 0.85 (3H, s, H-18), 0.92 (3H, s, H-19), 2.60 (1H, d, J=5.1, H-20a), 2.89 (1H, d, J=5.1, H-20b), 3.63 (1H, m, H-3). $^{13}$C NMR (101 MHz, CDCl$_3$): δ 71.84 (C-3), 70.71 (C-17), 53.72 (C-20), 53.05 (C-14), 42.23, 40.79, 40.38, 36.55, 36.15, 35.53, 34.84, 34.32, 30.66, 29.28, 27.18, 26.08, 23.70, 23.45, 20.34, 14.48. HR-MS (ESI) m/z: For C$_{20}$H$_{32}$O$_2$Na (M+Na) calcd: 327.2294; found: 327.2293.

Example 85: Pyridinium (3R,5R,8R,9S,10S,13S,14S,17S)-10,13-dimethylhexadecahydrospiro-[cyclopenta[a]phenanthren-17,2'-oxiran]-3-yl 3-sulfate (97)

Compound 97 was prepared according to General Procedure I—Preparation of C-3 Sulfate from compound 96 (50 mg, 0.16 mmol) affording compound 97 (36 mg, 47%) as a foam: [α]$_D^{20}$ +8.5 (c 0.14, CHCl$_3$). $^1$H NMR (400 MHz, CDCl$_3$): δ 0.83 (3H, s, H-18), 0.91 (3H, s, H-19), 2.64 (1H, d, J$_3$=9.3, H-20a), 3.40 (1H, d, J=10.5, H-20b), 4.43 (1H, m, H-3), 7.57 (2H, ddd, J$_1$=7.6, J$_2$=6.1, J$_3$=1.4, H-2', H-4', pyridinium), 7.99 (1H, tt, J$_1$=7.7, J$_2$=1.8, H-3', pyridinium), 8.75 (2H, d, J=4.6, H-1', H-5', pyridinium). $^{13}$C NMR (101. MHz, CDCl$_3$): δ 83.60 (C-17), 71.83 (C-3), 58.54 (CH$_2$N$_3$), 51.52, 46.19, 42.12, 40.64, 36.69, 36.50, 35.49, 34.99, 34.80, 32.35, 30.62, 27.15, 2634, 23.72, 23.43, 20.50, 14.30. IR spectrum (CHCl$_3$): 3140, 3093; 1638 (pyridinium); 1252, 1147 (SO$_3$). MS (ESI) m/z: 383.3 (40%, M−H-pyridine). HR-MS (ESI) m/z: For C$_{20}$H$_{31}$O$_5$S (M−H-pyridine) calcd: 383.1897; found: 383.1895.

Example 86: (3R,5R,8R,9S,10S,13S,14S,17S)-17-(Azidomethyl)-10,13-dimethylhexadecahydro-1H-cyclopenta[a]phenanthren-3,17-diol (98)

A solution of compound 96 (560 mg, 1.83 mmol), sodium azide (341 mg, 5.68 mmol) and ammonium chloride (341 mg, 6.37 mmol) in ethanol (28 ml) and water (5.6 ml) was heated at 90° C. overnight. Water was then added, the ethanol was evaporated and the product extracted with chloroform (2×50 ml). The combined organic extracts were dried over anhydrous sodium sulfate and the solvents evaporated under reduced pressure. The oily residue by column chromatography on silica gel (30% ether in petroleum ether) gave 500 mg (78%) of a white solid foam 98: $[\alpha]_D^{20}$ 0.0 (c 0.11, $CHCl_3$). $^1H$ NMR (400 MHz, $CDCl_3$): δ 0.86 (3H, s, H-18), 0.93 (3H, s, H-19), 3.26 (1H, d, J=12, $H_a$—$CH_2N_3$), 3.54 (1H, d, J=12, $H_b$—$CH_2N_3$), 3.63 (1H, m, H-3). $^{13}C$ NMR (101 MHz, $CDCl_3$): δ 83.60 (C-17), 71.83 (C-3), 58.54 ($CH_2N_3$), 51.52, 46.19, $^{13}C$ NMR (100 MHz, $CDCl_3$): δ 71.84 (C-3), 70.71 (C-17), 53.72 (C-20), 53.05 (C-14), 42.23, 40.79, 40.38, 36.55, 36.15, 35.53, 34.84, 34.32, 30.66, 29.28, 27.18, 26.08, 23.70, 23.45, 20.34, 14.48. IR spectrum ($CHCl_3$): 3613, 1037 (3α-OH); 3562, 1116 (17β-OH); 2106 (azid). MS ESI m/z: 370.2 (100%, M+Na). HR-MS (ESI) m/z: For $C_{20}H_{33}O_2N_3Na$ (M+Na) calcd: 370.2465; found: 370.2464.

Example 87: (4bR,6aR,8R,10aS,10bS,12aS)-8-Hydroxy-10a,12a-dimethylhexadecahydrochrysen-1 (2H)-one (99)

Sodium iodide (948 mg, 6.3 mmol) was added to a solution of compound 98 (220 mg, 0.63 mmol) in dried acetonitrile (10 ml). Trimethylsilyl chloride (0.8 ml, 26.6 mmol) was then added dropwise under inert atmosphere. The reaction mixture was stirred at room temperature and the progress of the reaction monitored by TLC. After complete conversion, dilute hydrochloric acid (5%, 10 ml) was added. The product was extracted with chloroform (2×40 ml). The combined organic extracts were washed with sodium sulfite solution, saturated aqueous sodium chloride solution, dried over anhydrous sodium sulfate and the solvents evaporated under reduced pressure. Yellowed residue was chromatographed on silica gel (30% ether in petroleum ether) gave 140 mg (73%) of 99: mp 201-201° C. (ether/petroleum ether), $[\alpha]_D^{20}$ −23.6 (c 0.12, $CHCl_3$). $^1H$ NMR (400 MHz, $CDCl_3$): δ 0.91 (3H, s, H-18), 1.06 (3H, s, H-19), 2.04 (1H, m, H-16a), 2.19 (1H, m, H-17a), 2.61 (1H, td, $J_1$=14.0 $J_2$=6.8, H-17b), 3.61 (1H, m, H-3). $^{13}C$ NMR (101 MHz, $CDCl_3$): δ 216.70 (C-17a), 71.86 (C-3), 51.73, 48.53, 41.71, 39.88, 37.34, 36.36, 35.68, 35.09, 35.00, 32.79, 30.74, 27.27, 26.11, 25.93, 23.49, 23.16, 19.87, 17.06. IR spectrum ($CHCl_3$): 3609, 1037 (OH); 1698 (C=O). MS ESI m/z: 327.2 (100%, M+Na), 631.5 (15%, 2M+Na). For $C_{20}H_{32}O_2$ (304.4) calcd: 78.90% C, 10.59% H; found: 78.55% C, 10.49% H.

Example 88: (2R,4aS,4bS,6aS,10bS,6aS,12aR)-4a,6a-Dimethyloktadecahydrochrysen-2-ol (100)

Compound 100 was prepared from compound 99 (110 mg, 0.36 mmol) analogously to the preparation of compound 48. Chromatography of the residue on silica gel (30% ether in petroleum ether) gave 100 (68 mg, 65%): mp 187-189° C. (acetone/n-heptane), $[\alpha]_D^{20}$ +17.1 (c 020, $CHCl_3$). $^1H$ NMR (400 MHz, $CDCl_3$): δ 0.78 (3H, s, H-18), 0.89 (3H, s, H-19), 3.62 (1H, m, H-3). $^{13}C$ NMR (101 MHz, $CDCl_3$): δ 72.07 (C-3), 51.26, 42.54, 42.45, 42.00, 40.77, 36.52, 36.03, 35.20, 35.09, 33.77, 30.77, 27.45, 27.39, 25.53, 24.23, 23.62, 21.66, 20.38, 17.09. IR spectrum ($CHCl_3$): 3609, 3447, 1031 (OH). MS ESI m/z: 313.3 (100%, M+Na). For $C_{20}H_{34}O$ (290.4) calcd: 82.69% C, 11.80% H; found: 82.42% C, 11.71% H.

Example 89: Pyridinium (2R,4aS,4bS,6aS,10bS,6aS,12aR)-4a,6a-dimethyloctadecahydrochrysen-2-yl 2-sulfate (101)

Compound 101 was prepared according to General Procedure I—Preparation of C-3 Sulfate from compound 100 (30 mg, 0.10 mmol) affording sulfate 101 (43 mg, 93%): mp 173-174° C., $[\alpha]_D^{20}$ +20.4 (c 0.27, $CHCl_3$). $^1H$ NMR (400 MHz, $CDCl_3$): δ 0.76 (3H, s, H-18), 0.87 (3H, s, H-19), 4.45 (1H, m, H-3), 8.00 (2H, m, H-2', H-4', pyridinium), 8.48 (1H, t, J=7.8, H-3', pyridinium), 8.98 (2H, d, J=5.5, H-1', H-5', pyridinium). $^{13}C$ NMR (101 MHz, $CDCl_3$): δ 145.87 (C-1', C-5'), 142.38 (C-3'), 127.32 (C-2', C-4'), 79.82 (C-3), 51.28, 42.52, 42.45, 42.02, 40.67, 35.95, 35.13, 34.97, 33.75, 33.34, 27.92, 27.3, 27.22, 25.45, 24.20, 23.53, 21.63, 20.34, 17.07. IR ($CHCl_3$): 3139, 3100, 1637, 1490 (pyridinium); 1263, 1238, 1235, 1043 ($SO_3$). MS ESI m/z: 369.3 (100%, M−H-pyridine). HR-MS (ESI) m/z: For $C_{20}H_{33}O_4S$ (100%, M−H-pyridine) calcd: 369.2105; found: 369.2103.

Example 90: 3-(((2R,4aS,4bS,6aS,10bS,12aR)-4a,6a-Dimethyloctadecahydrochrysen-2-yl)oxy)-3-oxopropanoic acid (102)

Compound 102 was prepared according to General Procedure III—Preparation of C-3 Hemimalonate from compound 100 (132 mg, 0.45 mmol). Chromatography on silica gel (30% ethyl acetate in petroleum ether) gave compound 102 (157 mg, 92%): mp 145.3-147.2° C. (acetone/n-heptane), $[\alpha]_D^{20}$ +25.3 (c 0.29, $CHCl_3$). $^1H$ NMR (400 MHz, $CDCl_3$): δ 0.79 (3H, s, H-18), 0.91 (3H, s, H-19), 3.36-3.47 (2H, m, $OCCH_2CO$), 4.80-4.90 (1H, m, H-3). $^{13}C$ NMR (101 MHz, $CDCl_3$): δ 168.89 (COOH), 168.08 (COO), 77.05 (C-3), 51.19, 42.51, 42.35, 41.79, 40.75, 40.17, 35.95, 35.05, 34.73, 33.77, 31.99, 27.43, 27.15, 26.58, 25.39, 24.20, 23.53, 21.62, 20.39, 17.08. IR spectrum ($CHCl_3$): 3510 (OH, COOH, monomer); 3131 (OH, COOH, dimer); 1759 (C=O, COOH, monomer); 1734 (C=O); 1717 (C=O, COOH, dimer); 1410, 1291 (C—O, COOH, dimer); 1345, 1178 (C—O, COOH, monomer). MS (ESI) m/z: 399.3 (100%, M+Na). HR-MS (ESI) m/z: For $C_{23}H_{36}O_4Na$ (M+Na) calcd: 399.2506, found: 399.2506.

Example 91: 4-(((2R,4aS,4bS,6aS,10bS,12aR)-4a,6a-Dimethyloctadecahydrochrysen-2-yl)oxy)-4-oxobutanoic acid (103)

Compound 103 was prepared according to General Procedure II—Preparation C-3 Hemisuccinate from compound 100 (100 mg, 0.34 mmol). Chromatography on silica gel (10% ether in petroleum ether) gave compound 103 (81 mg, 60%): mp 136-138° C. (acetone/water), $[\alpha]_D^{20}$ +34.8 (c 0.21, $CHCl_3$). $^1H$ NMR (400 MHz, $CDCl_3$): δ 0.79 (3H, s, H-18), 0.91 (3H, s, H-19), 2.59 (2H, ddd, $J_1$=7.6, $J_2$=6.1, $J_3$=1.4, succinic acid) 2.68 (2H, ddd, $J_1$=7.3, $J_2$=6.1, $J_3$=1.3, succininic acid), 4.75 (1H, tt, $J_1$=11.3, $J_2$=4.7, H-3). $^{13}C$ NMR (100 MHz, $CDCl_3$): δ 177.29 (COOH), 171.66 (COO), 75.05 (C-3), 51.05, 42.37, 42.23, 41.64, 40.58, 35.81, 34.93, 34.68, 33.62, 32.03, 29.28, 28.92, 27.29, 27.04, 26.58, 25.26, 24.05, 23.41, 21.48, 20.23, 16.93. IR spectrum ($CHCl_3$): 3517 (OH, COOH, monomer); 2674 (OH, COOH, dimer); 1753 (C=O, COOH, monomer); 1717 (C=O, COOH, dimer); 1727 (C=O, ester). MS (ESI) m/z: 413.2 (100%, M+Na). HR-MS (ESI) m/z: For $C_{24}H_{39}O_4$ (M+H) calcd: 391.2843; found: 391.2839. For $C_{24}H_{38}O_4$ (402.6) calcd: 73.81% C, 9.81% H; found: 73.54% C, 9.88% H.

Example 92: 5-(((2R,4aS,4bS,6aS,10bS,12aR)-4a, 6a-Dimethyloktadecahydrochrysen-2-yl)oxy)-5-oxopentanoic acid (104)

Compound 104 was prepared according to General Procedure IV—Preparation of C-3 Hemiglutarate from compound 100 (106 mg, 0.36 mmol). Chromatography on silica gel (1-10% acetone in petroleum ether) gave compound 104 (137 mg, 93%): mp 148.7-151.0° C. (acetone/n-heptane), $[\alpha]_D^{20}$ +31.7 (c 0.33, CHCl$_3$). $^1$H NMR (400 MHz, CDCl$_3$): δ 0.78 (3H, s, H-18), 0.90 (3H, s, H-19), 1.96 (2H, p, J=7.3, H-3'), 2.36 (2H, t, J=7.3, H-2'), 2.43 (2H, t, J=7.3, H-4'), 4.74 (1H, m, H-3). $^{13}$C NMR (101 MHz, CDCl$_3$): δ 177.85 (COOH), 172.54 (COO), 74.74 (C-3), 51.22, 42.54, 42.39, 41.81, 40.74, 35.98, 35.11, 34.87, 33.78 (2×C), 32.99, 32.29, 27.45, 27.21, 26.84, 25.43, 24.21, 23.58, 21.65, 20.39, 20.14, 17.09. IR spectrum (CHCl$_3$): 3517 (OH, COOH, monomer); 3087 (OH, COOH, dimer); 1750 (C=O, COOH, monomer); 1720 (C=O), 1714 (C=O, COOH, dimer); 1381 (CH$_3$). MS (ESI) m/z: 427.3 (100%, M+Na). HR-MS (ESI) m/z: For C$_{25}$H$_{40}$O$_4$Na (M+Na) calcd: 427.2819; found: 427.2819.

Example 93: 5-Benzyl 1-((2R,4aS,4bS,6aS,10bS,12aR)-4a,6a-dimethyloctadecahydrochrysen-2-yl)-N-(tert-butoxycarbonyl)-L-glutamate (105)

A solution of dicyclohexylcarbodiimide (1M, benzene, 1 ml) was added to a stirred solution of compound 100 (200 mg, 0.68 mmol), 4-(N,N-dimethylamino)pyridine (8.5 mg, 0.068 mmol) and 5-benzyl-N-benzyloxycarbonyl-L-glutamic acid (Boc-Glu(OBzl)-OH, 255 mg, 0.75 mmol) in dried benzene (15 ml) and the reaction mixture was stirred at room temperature under inert atmosphere for 5 h. Then, the solids were filtered off and washed with dry benzene. The reaction mixture was concentrated (about ⅔ of volume), saturated aqueous sodium bicarbonate solution was added and the product extracted into chloroform (2×50 ml). The combined organic extracts were washed with saturated aqueous sodium chloride solution and dried over anhydrous sodium sulfate. Chromatography on silica gel (3% acetone in petroleum ether) gave oily compound 105 (375 mg, 89%): $[\alpha]_D^{20}$+17.5 (c 0.19, CHCl$_3$). $^1$H NMR (400 MHz, CDCl$_3$): δ 0.78 (3H, s, H-18), 0.90 (3H, s, H-19), 1.43 (9H, s, t-butyl), 2.15-2.25 (1H, m, H-3'), 2.37-2.52 (2H, m, H-4'), 4.28 (1H, m, H-2'), 4.76 (1H, m, H-3), 5.10 (3H, m, NH, OCH$_2$Ph), 7.35 (5H, m, OCH$_2$Ph). $^{13}$C NMR (101 MHz, CDCl$_3$): δ 172.77 (C-1', C-5'), 156.15 (NHCO), 135.97 (C-1', benzyl), 128.72 (C-2", C-6", benzyl), 128.42 (C-4", benzyl), 128.35 (C-3", C-5", benzyl), 80.06 (OCMe$_3$), 76.04 (C-3), 66.62 (OCH$_2$Ph), 53.23, 51.15, 42.51, 42.34, 41.81, 40.72, 35.97, 35.08, 34.77, 33.78, 32.15, 30.49, 28.48 (3×C, OCMe$_3$), 28.16, 27.44, 27.17, 26.72, 25.39, 24.21, 23.54, 21.65, 20.40, 17.09. IR spectrum (CHCl$_3$): 3436, 1713 (NH-Boc); 3092, 3068, 1454 (benzyl); 1730 (C=O); 1467, 1368, 1381, 1392 (Boc). MS (ESI) m/z: 632.4 (100%, M+Na), 1242.6 (5%, 2M+1). For C$_{37}$H$_{55}$NO$_6$ (609.8) calcd: 72.87% C, 9.09% H, 2.30% N; found: 73.15% C, 9.22% H, 2.15% N.

Example 94: (4S)-4-Amino-5-(((2R,4aS,4bS,6aS,10bS,12aR)-4a,6a-dimethyloctadekahydrochrysen-2-yl)oxy)-5-oxopentanoic acid (106)

A solution of the protected steroid derivative 105 (118 mg, 0.19 mmol) in methanol (5 ml) was stirred in the presence of a palladium catalyst on activated carbon (Pd/C, 10%, 5 mg) under slight positive pressure of hydrogen at room temperature. The reaction was followed by thin layer chromatography (petroleum ether/acetone, 1:1). After 1.5 h, the catalyst was filtered off on a short column of silica gel and washed with chloroform. The combined organic fractions were concentrated. Chromatography on silica gel (10% acetone in petroleum ether) gave tert-butyloxycarbonyl-protected product (62 mg, 62%). The oily residue was dissolved in concentrated trifluoroacetic acid (1 ml) and the solution was allowed to stand at room temperature for 15 min. Hydrochloric acid was then removed by blowing a stream of nitrogen. To the residue was added a mixture of pyridine/methanol (0.5:4.5 mL) and the resulting mixture was added dropwise to a mixture of ice and water (5 ml). After 5 h, the white precipitate was filtered off and dried at 50° C. overnight affording compound 106 (34 mg, 68%): mp 162-165° C. (methanol), $[\alpha]_D^{20}$ +20.7 (c 0.26, CHCl$_3$/MeOH, 1.80:0.04). $^1$H NMR (400 MHz, CDCl$_3$/MeOH): δ 0.72 (3H, s, H-18), 0.85 (3H, s, H-19), 2.41 (2H, m, H-3', H-4'), 3.68 (1H, m, H-2'), 4.75 (1H, m, H-3). $^{13}$C NMR (101 MHz, CDCl$_3$/MeOH): δ 177.55 (COOH), 171.27 (COO), 76.71 (C-3), 53.42, 50.95, 42.22, 42.06, 41.59, 40.54, 35.72, 34.82, 34.43, 33.49, 33.27, 31.83, 27.47, 27.14, 26.92, 26.42, 25.15, 23.94, 23.18, 21.33, 20.12, 16.73. IR spectrum (CHCl$_3$): 2650, 2170, 1610 (NH$_3^+$); 1743 (C=O); 1571 (COO$^-$). MS (ESI) m/z: 418.3 (100%, M–H), 837.5 (40%, 2M–H). HR-MS (ESI) m/z: For C$_{25}$H$_{40}$NO$_4$ (M–H) calcd: 418.2962; found: 418.2959.

Example 95: 1-((3R,5R,8R,9S,10S,13S,14S)-3-(Methoxymethoxy)-10,13-dimethylhexadecahydro-1H-cyclopenta[a]phenanthren-17(2H,10H,14H)ylidene)-2-(tosyloxy)hydrazine (108)

To a solution of 3alpha-methoxy-5beta-andostan-17-one 107 (1.00 g, 3 mmol) and tosyl hydrazide (1.63 g, 8.5 mmol) in dried methanol (70 ml) was added powdered molecular sieve (40 msh, 2 g) The mixture was refluxed while stirring under inert atmosphere for 72 h. The progress of the reaction was monitored by TLC, using petroleum ether/acetone, 4:1. The reaction mixture was cooled to room temperature and filtered off. The filtrate was concentrated under reduced pressure. The residue was dissolved in toluene (100 ml), the precipitate was filtered off and the filtrate was evaporated under reduced pressure. The residue was dissolved in ethyl acetate. The solution was washed with saturated aqueous sodium bicarbonate (3×25 ml), brine (25 ml) and dried over anhydrous sodium sulfate. The solvents were evaporated under reduced pressure and the residue purified by column chromatography on silica gel (15% ethyl acetate in petroleum ether) affording 1.05 g of hydrazone 108 (67.4%): mp 97.4-99.5° C., $[\alpha]_D^{20}$ +44.2 (c 0.33, CHCl$_3$). $^1$H NMR (400 MHz, CDCl$_3$): δ 0.82 (3H, s, H-18), 0.92 (3H, s, H-19), 2.43 (3H, s, Tos), 3.36 (3H, s, H-2', MOM), 3.52 (1H, m, H-3), 4.67 (2H, s, H-1', MOM) 7.29 (2H, m, H-2" and H-4", Tos), 7.81 (2H, d, J=8.3, H-1" and H-5", Tos). $^{13}$C NMR (101 MHz, CDCl$_3$): δ 129.49, 128.64, 128.02, 125.96, 94.62, 55.16, 53.29, 41.95, 40.58, 35.32, 35.23, 34.85, 33.53, 31.76, 27.69, 26.91, 25.83, 25.34, 23.25, 21.82, 21.64, 20.15, 20.09, 19.79, 16.65, 13.69. IR spectrum (CHCl$_3$): 2938 (CH$_2$); 1659 (C=N); 1167 (SO$_3$); 1045, 1036 (CO-COC). MS (ESI) m/z: 503.2 (10%, M–CH$_3$). For C$_{28}$H$_{42}$N$_2$O$_5$S (518.7) calcd: 64.84% C, 8.16% H, 5.40% N; found: 65.17% C, 8.50% H, 5.08% N.

Example 96: (3R,5R,8R,9S,10S,13R,14S)-3-(methoxymethoxy)-10,13-dimethyl-2,3,4,5,6,7,8,9,10,11,12,13,14,15-tetradecahydro-1H-cyclopenta[a]phenanthrene (109)

Tosylhydrazone 108 (1 g, 1.93 mmol) in dried tetrahydrofuran (30 ml) was cooled to 0° C. and while stirring, methyllithium (14 ml, 1.6 M ether) was added under inert atmosphere. The reaction was stirred 2 h at 0° C. overnight at room temperature. The mixture was then recooled to 0° C. and quenched with water (50 ml). The product was extracted into ethyl acetate (3×25 ml), the combined organic extracts washed with aqueous citric acid (5%, 30 ml), saturated aqueous sodium chloride solution and dried over anhydrous sodium sulfate. The solvents were evaporated under reduced pressure. The residue (880 mg) was purified by column chromatography on silica gel (1% acetone in petroleum ether) yielding 606.4 mg (98%) of non-crystallising olefin 109: $[\alpha]_D^{20}$ +20.2 (c 0.35, $CHCl_3$). $^1$H NMR (400 MHz, $CDCl_3$): δ 0.74 (3H, s, H-18), 0.95 (3H, s, H-19), 3.37 (3H, s, H-2' MOM), 3.53 (1H, tt, $J_1$=11.2, $J_2$=4.7, H-3), 4.69 (2H, s, H-1', MOM), 5.67 (1H, ddd, $J_1$=5.8, $J_2$=3.0, $J_3$=1.5, H-16), 5.83 (1H, ddd, $J_1$=5.8, $J_2$=2.5, $J_3$=1.1, H-16). $^{13}$C NMR (101 MHz, $CDCl_3$): δ 144.08 (C-17), 129.45 (C-16), 94.75 (O—C—O), 77.01 (C-3), 56.33, 55.31, 45.81, 42.44, 41.44, 36.27, 35.52, 35.21, 34.68, 33.82, 32.19, 27.84, 27.39, 26.76, 23.56, 20.86, 17.19. IR spectrum ($CHCl_3$): 3049 (C=C); 2935 ($CH_2$); 1047, 1036 (COCOC). MS (ESI) m/z: 341.4 (100%, M+Na). HR-MS (ESI) m/z: For $C_{21}H_{34}O_2Na$ (M+Na) calcd: 341.2451; found: 341.2452. For $C_{21}H_{34}O_2$ (318.5) calcd: 79.19% C, 10.76% H; found: 79.29% C, 10.85% H.

Example 97: (3R,5R,8S,9S,10S,13R,14S,16R)-3-(Methoxymethoxy)-10,13-dimethylhexadecahydro-1H-cyclopenta[a]phenanthren-16-ol (110)

To a saturated solution of the dimer of 9-borabicyclo [3.3.1]nonane (102 ml, 51 mmol) which was cooled to 0° C. under inert atmosphere was added a solution of olefin 109 (2 g, 6.30 mmol) in tetrahydrofuran (42 ml). The reaction mixture was stirred at 0° C. under argon for 4 h. Water was added (32.6 ml) and aqueous sodium hydroxide (10%, 32.6 ml), hydrogen peroxide (30%, 48.6 ml), and the mixture was stirred at room temperature overnight. Then, sodium sulfite (3.36 g), acetic acid (98%, 16.4 ml), water (80.8 ml) and aqueous citric acid (5%, 81.8 ml) were added. The product was extracted into ethyl acetate (3×80 ml). The combined organic extracts were washed with saturated aqueous sodium chloride solution (50 ml), aqueous sodium bicarbonate (5%, 2×50 ml), again with saturated aqueous sodium chloride solution (50 ml) and dried over anhydrous sodium sulfate. The organic phase was evaporated under reduced pressure and chromatography of the residue on silica gel (1-5% acetone in petroleum ether) gave 1.26 mg (60%) of hydroxy derivative 110: mp 98.7-100° C. (acetone/n-heptane), $[\alpha]_D^{20}$+16.6 (c 0.33, $CHCl_3$). $^1$H NMR (400 MHz, $CDCl_3$): δ 0.69 (3H, s, H-18), 0.91 (3H, s, H-19), 3.37 (3H, s, H-2', MOM), 3.53 (1H, tt, $J_1$=11.2, $J_2$=4.7, H-3), 4.45 (1H, tdd, $J_1$=7.6, $J_2$=6.0, $J_3$=1.6, H-16), 4.69 (2H, s, H-1', MOM). $^{13}$C NMR (101 MHz, $CDCl_3$): δ 94.72 (C-3), 77.03 (C-16), 72.07, 55.30, 52.31, 52.29, 42.28, 42.11, 40.80, 39.06, 37.44, 35.86, 35.54, 35.05, 33.74, 27.88, 27.33, 26.85, 23.56, 20.59, 18.81. IR spectrum ($CHCl_3$): 3612 (OH); 2941 ($CH_2$); 1040 (COCOC). MS (ESI) m/z: 359.3 (100%, M+Na). HR-MS (ESI) m/z: For $C_{21}H_{35}O_3$ (M+Na) calcd: 359.2558; found: 359.2558. For $C_{21}H_{36}O_3$ (336.5) calcd: 74.95% C, 10.78% H; found: 74.68% C, 11.02% H.

Example 98: (3R,5R,8S,9S,10S,13R,14S)-3-(Methoxymethoxy)-10,13-dimethylhexadecahydro-16H-cyclopenta[a]phenanthren-16-one (111)

Compound 110 (3.17 g, 9.4 mmol) was dissolved in freshly dried dichloromethane (150 ml). Then, pyridinium chlorochromate (16.7 g, 77.5 mmol) in dried pyridine (10 ml) was added. The mixture was stirred under inert atmosphere at room temperature for 2 h. The reaction mixture was filtered through a small silica gel column (15 g), while washing with ethyl acetate. The solvents were evaporated; the residue redissolved in ethyl acetate and washed with aqueous citric acid (5%, 2×40 ml), saturated aqueous sodium chloride solution (50 ml), saturated aqueous sodium bicarbonate solution (2×30 ml), again saturated aqueous sodium chloride solution (50 ml) and dried over anhydrous sodium sulfate. Evaporation of solvents under reduced pressure afforded 2.59 g (95%) of 111: mp 107.9-108° C. (acetone/n-heptane), $[\alpha]_D^{20}$ −134.7 (c 0.35, $CHCl_3$). $^1$H NMR (400 MHz, $CDCl_3$): δ 0.86 (3H, s, H-18), 0.95 (3H, s, H-19), 3.37 (3H, s, H-2', MOM), 3.54 (1H, ddd, $J_1$=15.8, $J_2$=11.1, $J_3$=4.7, H-3), 4.69 (2H, s, H-1', MOM). $^{13}$C NMR (101 MHz, $CDCl_3$): δ 218.91 (C=O), 94.78 (C-3), 56.12, 55.34, 51.91, 42.05, 40.68, 39.49, 39.40, 38.56, 35.47, 35.25, 35.10, 33.71, 27.87, 27.13, 26.89, 23.49, 20.50, 18.23. IR spectrum ($CHCl_3$): 2937 (—$CH_2$—); 1737 (C=O); 1045, 1037 (COCOC). MS (ESI) m/z: 335.3 (32%, M+H) 273.2 (100%). HR-MS (ESI) m/z: For $C_{21}H_{35}O_3$ (M+H) calcd: 335.2586; found: 335.2579. For $C_{21}H_{34}O_3$ (334.5) calcd: 75.41% C, 10.25% H; found: 75.66% C, 10.33% H.

Example 99: (3R,5R,8S,9S,10S,13R,14S)-3-Hydroxy-10,13-dimethylhexadecahydro-16H-cyclopenta-[a]phenanthren-16-one (112)

To a solution of the protected derivative 111 (3.4 g, 10.2 mmol) in methanol (95 ml) was added hydrochloric acid (1.8 ml, 37%) in methanol (30 ml). The reaction mixture was stirred under argon at room temperature overnight. Water was added (100 ml) and the mixture concentrated under reduced pressure. The product was extracted into ethyl acetate (3×70 ml), the combined organic phases washed with saturated aqueous sodium bicarbonate, saturated aqueous sodium chloride solution, dried over anhydrous sodium sulfate and the solvents evaporated under reduced pressure. Hydroxyketone 112 was obtained (3.17 g, 93%): mp 135.8-136.7° C. (acetone/n-heptane), $[\alpha]_D^{20}$ −167.4 (c 0.33, $CHCl_3$). $^1$H NMR (400 MHz, $CDCl_3$): δ 0.86 (3H, s, H-18), 0.96 (3H, s, H-19), 3.65 (1H, tt, $J_1$=10.8, $J_2$=4.7, H-3). $^{13}$C NMR (101 MHz, $CDCl_3$): δ 218.88 (C=O), 71.81, 56.12, 51.91, 42.01, 40.74, 39.48, 39.40, 38.56, 36.55, 35.49, 35.22, 34.96, 30.64, 27.09, 26.93, 23.45, 20.51, 18.23. IR spectrum ($CHCl_3$): 2936 ($CH_2$); 1736 (C=O); 3609, 1032 (OH). MS (ESI) m/z: 290.2 (100%, M). HR-MS (ESI) m/z: For $C_{19}H_{30}O_2$ (M+Na) calcd: 313.2138; found: 313.2137. For $C_{19}H_{30}O_2$ (290.4) calcd: 78.57% C, 10.41% H; found: 78.27% C, 10.36% H.

Example 100: (3R,5R,8S,9S,10S,13R,14S)-10,13-Dimethyl-16-methylenhexadecahydro-1H-cyklopenta[a]phenanthren-3-ol (113)

Compound 113 was prepared from compound 112 (800 mg, 2.76 mmol) analogously to the preparation of compound 66. Chromatography on, silica gel (1-5% acetone in petroleum ether) gave 756 mg (95%) of compound 113: mp 165.3-165.6° C. (acetone/n-heptane), $[\alpha]_D^{20}$ −69.8 (c 0.35, $CHCl_3$). $^1$H-NMR (400 MHz, $CDCl_3$): δ 0.86 (3H, s, H-18), 0.96 (3H, s, H-19), 4.88 (ddh, $J_1$=4.4, $J_2$=3.0, $J_2$=1.6, 1H), 3.63 (tt, $J_1$=11.1, $J_2$=4.7, 1H), 2.33 (ddt, $J_1$=16.1, $J_2$=7.5, $J_2$=1.6, 1H). $^{13}$C NMR (101 MHz, $CDCl_3$): δ 151.39 (=$CH_2$), 107.09 (C-16), 71.99 (C-3), 54.39, 49.61, 42.23, 40.89, 40.78, 38.79, 36.63, 35.96, 35.50, 34.91, 33.54, 30.71, 27.29, 26.85, 23.53, 20.92, 17.76. IR spectrum (CHCl$_3$): 3609 (OH); 3015, 1658 (=CH$_2$); 2934 (CH$_2$). MS (ESI) m/z: 311.3 (100%, M+Na). HR-MS (ESI) m/z: For C$_{25}$H$_{38}$O$_4$Na (M+Na) called: 311.2345; found: 311.2344. For C$_{20}$H$_{32}$O (288.5) calcd: 83.27% C, 11.18% H; found: 83.02% C, 11.07% H.

Example 101: Pyridinium (3R,5R,8S,9S,10S,13R, 14S)-10,13-dimethyl-16-methylenhexadekhydro-1H-cyclopenta[a]phenanthren-3-yl 3-sulfate (114)

Compound 114 was prepared according to General Procedure I—Preparation of C-3 Sulfate from compound 113 (83 mg, 0.29 mmol) affording sulfate 114 (66 mg, 56%): mp 180-182° C. (chloroform), [α]$_D^{20}$ −41.9 (c 0.35, CHCl$_3$). $^1$H NMR (400 MHz, CDCl$_3$): δ 0.70 (3H, s, H-18), 0.91 (3H, s, H-19), 2.30 (1H, dd, J$_1$=16.0, J$_2$=7.7), 4.45 (1H, tt, J$_1$=11.2, J$_2$=4.9 H-3), 4.87 (2H, m, =CH$_2$), 8.02 (2H, m, H-2' and H-4', pyridinium), 8.48 (1H, t, J=8.6, H-3', pyridinium), 8.99 (2H, d, J=5.2, H-1' and H-5', pyridinium). $^{13}$C NMR (101 MHz, CDCl$_3$): δ 218.89 (C-16), 178.74, 145.89 (C-1' and C-5', pyridinium), 142.39 (C-3', pyridinium), 127.31 (C-2' and C-4', pyridinium), 79.51 (C-3), 56.11, 51.94, 42.05, 40.68, 39.48, 39.38, 38.57, 35.42, 35.21, 34.85, 33.42, 27.85, 26.85, 26.82, 23.68, 20.40, 18.02. IR spectrum (CHCl$_3$): 1736 (C=O); 1656 (C=C); 1460 (=CH, pyridine); 1263, 1171, 969, 947 (OSO$_3$). MS (ESI) m/z: 467.2 (100%, M+H-pyridine). HR-MS (ESI) m/z: For C$_{20}$H$_{31}$O$_4$S calcd: 367.1946; found: 367.1945.

Example 102: 4-(((3R,5R,8S,9S,10S,13R,14S)-10, 13-Dimethyl-16-methylenhexadecahydro-1H-cyclopenta[a]phenanthren-3-yl)oxy)-4-oxobutanoic acid (115)

Compound 115 was prepared according to General Procedure II—Preparation of C-3 Hemisuccinate from compound 113 (95 mg, 0.33 mmol). Chromatography on silica gel (10-20% acetone in petroleum ether) gave compound 115 (120.4 mg, 84.3%): mp 165-165.7° C. (acetone/n-heptane), [α]$_D^{20}$ −36.8 (c 0.29, CHCl$_3$). $^1$H NMR (400 MHz, CDCl$_3$): δ 0.73 (3H, s, H-18), 0.94 (3H, s, H-19), 2.38-2.27 (2H, m, H-16a, H-16b), 2.72-2.55 (4H, m, succinic acid), 4.76 (1H, tt, J$_1$=11.4, J$_2$=4.7, H-3), 4.89 (2H, ddq, J$_1$=4.2, J$_2$=2.9, J$_3$=1.5, =CH$_2$), 4.58-4.65 (2H, m), 4.74 (1H, tt, J$_1$=11.3, J$_2$=4.7). $^{13}$C NMR (101 MHz, CDCl$_3$): δ 177.07 (COOH), 171.82 (COO), 151.29 (=CH$_2$), 107.14 (C-16), 75.11 (C-3), 54.37, 49.61, 42.04, 40.89, 40.77, 38.75, 35.90, 35.16, 34.93, 33.51, 32.34, 29.43, 29.00, 27.11, 26.72, 23.49, 20.94, 17.75. IR spectrum (CHCl$_3$): 3518 (OH, COOH, monomer); 3070, 1657 (=CH$_2$); 2674 (OH, COOH, dimer); 1752 (C=O, COOH, monomer); 1717 (C=O, COOH, dimer); 1727 (C=O, ester). MS (ESI) m/z: 387.3 (100%, M−1). HR-MS (ESI) m/z: For C$_{24}$H$_{35}$O$_4$ (M−H) calcd: 387.2541; found: 387.2527. For C$_{24}$H$_{35}$O$_4$ (388.5) calcd: 74.19% C, 9.34% H; found: 74.19% C, 9.34% H.

Preparation of compounds 116-128 is summarized in Table 1.

Example 103: (R)-5-benzyl 1-((3R,5R,8S,9S,10S, 13S,14S)-10,13-dimethylhexadecahydro-1H-cyclopenta[a]phenanthren-3-yl) 2-((tert-butoxycarbonyl) amino)pentanedioate (129)

Compound 129 was prepared from compound 48 (309 mg, 1.11 mmol) analogously to the preparation of compound 105. Chromatography on silica gel (3% acetone in petroleum ether) gave 214 mg (36%) of slightly impure desired product and 361 mg (54%) of pure oily compound 129: [α]$_D^{20}$ +17.8 (c 0.27, CHCl$_3$). $^1$H NMR (400 MHz, CDCl$_3$): δ 0.68 (3H, s, H-18), 0.93 (3H, s, H-19), 1.43 (9H, s, O$^t$Bu), 2.20 (1H, m, H-3a'), 2.44 (2H, m, H-4'), 4.28 (1H, m, H-2'), 4.84 (1H, m, H-3), 4.76 (1H, m, H-3), 5.11 (3H, m, OCH$_2$Ph a NH). $^{13}$C NMR (101 MHz, CDCl$_3$): δ 172.59 (C-1'), 171.63 (C-5'), 155.34 (NHCO), 135.80 (C-1, benzyl), 128.55 (2×C-3, benzyl), 128.24 (C-4, benzyl), 128.18 (2×C-2, benzyl), 79.88 (O$^t$Bu), 75.85 (C-3), 66.45 (OCH$_2$Ph), 54.50, 53.05, 41.95, 40.93, 40.73, 40.48, 38.98, 36.18, 35.06, 34.73, 32.15, 30.32, 28.32, 28.0, 27.0, 26.70, 26.55, 25.51, 23.32 (3×C, O$^t$Bu), 20.86, 20.59, 17.50. IČ (CHCl$_3$): 3092, 3068 (CH, benzyl); 1730 (C=O, ester); 1713 (C=O, amide); 1499 (NH, amide); 1260, 1235 (OCN, ester); 1165 (O$^t$Bu). MS (ESI) m/z: 618.2 (100%, M+Na), 619.2 (40%, M+Na+1). HR-MS (ESI) m/z: For C$_{36}$H$_{53}$NO$_6$Na [M+Na] calcd: 618.3765; found: 618.3763. For C$_{36}$H$_{53}$NO$_6$ (595.2) calcd: 72.57% C, 8.97% H, 2.35% N; found: 72.52% C, 9.12% H, 2.11% N.

Example 104: (4S)-4-Amino-5-(((3R,5R,8S,9S,10S, 13S,14S)-10,13-dimethylhexadecahydro-1H-cyclopenta[a]phenanthren-3-yl)oxy)-5-oxopentanoic acid (130)

Compound 130 was prepared from compound 129 (361 mg, 0.61 mmol) analogously to the preparation of compound 106 affording 186 mg (80%) of 130: mp 167-168° C., [α]$_D^{20}$ +24.4 (c 0.16, CHCl$_3$). $^1$H NMR (400 MHz, CDCl$_3$+3 drops of MeOD): δ 0.61 (3H, s, H-18), 0.88 (3H, s, H-19), 2.40 (2H, t, J=6.3, H-3'), 3.69 (1H, dd, J$_1$=8.1, J$_2$=3.4, H-2'), 4.75 (1H, m, H-3). $^{13}$C NMR (101 MHz, CDCl$_3$): δ 177.51 (COOH), 171.32 (COO), 76.61 (C-3), 54.40, 53.24, 41.83, 40.79, 40.65, 40.31, 38.83, 36.04, 34.85, 34.59, 33.10, 31.94, 27.37, 26.87, 26.57, 2638, 25.36, 23.14, 20.72, 20.42, 17.32. IR spectrum (CHCl$_3$): 2646, 2179, 1609 (NH$_3^+$); 1748 (C=O, ester); 1570 (COOH). MS (ESI) m/z: 406.3 (100%, M+1), 428.3 (99%, M+Na). HR-MS (ESI) m/z: For C$_{24}$H$_{40}$NO$_4$ [M+1] calcd: 406.2951, found: 406.2951.

Example 105: 1-((3R,5R,8S,9S,10S,13S,14S)-10, 13-Dimethylhexadecahydro-1H-cyclopenta[a] phenanthren-3-yl)-5-oxopyrrolidine-3-carboxylic acid (131), mixture of isomers Diisopropylethylamine (336 μl, 1.93 mmol) was added to a solution of amine 57 (200 mg, 0.64 mmol) in nitroethane (10 ml) at room temperature. Then, the reaction mixture was heated at 105° C. for 22 h followed by heating at 125° C. for additional 20 h. The crude reaction mixture was concentrated and directly purified by column chromatography on silica gel (4:1:0.1 petroleum ether/acetone/acetic acid) affording compound 131 (45 mg, 18%) as a mixture of carboxylic acids (1:1 according NMR): mp 85-86.6° C., [α]$_D^{20}$ +20.1 (c 0.15, CHCl$_3$). $^1$H NMR (600 MHz, CDCl$_3$): δ 0.69 (3H, s, H-18), 0.95 (3H, s, H-19), 0.99 (1H, m, H-14), 1.09-1.465 (2H, m, H-7), 1.16-1.735 (2H, m, H-12), 1.16-1.43 (2H, m, H-17), 1.16-1.65 (2H, m, H-15), 1.27-1.42 (2H, m, H-11), 1.24-1.87 (2H, m, H-6), 1.26-1.91 (2H, m, H-4), 1.34 (1H, m, H-8), 1.34 (1H, m, H-9), 1.50 (1H, m, H-5), 1.61 (2H, m, H-16), 2.75 (2H, m, NC(=O)CH$_2$CH(COOH) CH$_2$), 3.25 (1H, m, NC(=O)CH$_2$CH(COOH)CH$_2$), 3.66 (2H, m, NC(=O)CH$_2$CH(COOH)CH$_2$), 4.01 (1H, br, H-3). $^{13}$C NMR (150.9 MHz, CDCl$_3$): δ 176.48 (COOH), 172.09 (NC(=O)CH$_2$CH(COOH)CH$_2$), 54.58 (C-14), 51.71 (C-3), 45.17 (NC(=O)CH$_2$CH(COOH)CH$_2$), 42.51 (C-5), 40.94 (C-13), 41.01 (C-9), 40.50 (C-17), 39.04 (C-12), 36.17 (C-8), 36.05 (NC(=O)CH$_2$CH(COOH)CH$_2$), 35.95 (C-1), 34.73 (C-10), 34.56 (NC(=O)CH$_2$CH(COOH)CH$_2$), 30.15 (C-4), 27.09 (C-6), 26.86 (C-7), 25.51 (C-15), 24.70 (C-2), 23.63 (C-19), 20.84 (C-11), 20.58 (C-16), 17.52 (C-18). IR spectrum (CHCl$_3$): 3513 (OH), 2935 (CH$_2$). 1754 (COOH), 1714 (C=O), 1674 (amide). MS (ESI) m/z: 1184.8 (40%, 3M+Na), 797.5 (65%, 2M+Na), 410.3 (100%, M+Na), 388.17 (15%, M+H). HR-MS (ESI) m/z: for C$_{24}$H$_{37}$O$_3$NNa (M+Na) calcd: 410.2666, found 410.2671; for C$_{24}$H$_{38}$O$_3$N [M+H] calcd. 388.2846, found 388.2852.

Example 106: (3S,5R,8R,9S,10S,13S,14S)-10,13-Dimethyl-17-methylenehexadecahydro-1H-cyclopenta[a]phenanthren-3-ol (132)

A solution of methyltriphenylphosphonium iodide (14.27 g, 35.20 mmol) in dimethyl sulfoxide (80 ml) was stirred at room temperature for 20 min under inert atmosphere. Then sodium hydride (50% in parafine oil, 1.44 g, 35.97 mmol) was added. After 1 h of stirring, a solution of 3beta-5beta-androstan-17-one (2.0 g, 6.89 mmol) in dimethyl sulfoxide (80 ml) was added and after 2.5 h of stirring at 70° C. under inert atmosphere, the reaction mixture was poured into brine. The precipitated white solid was collected by filtration, washed with brine, dried and the solvents were evaporated in vacuo. The residue was chromatographed on silica gel (5-10% ethyl acetate in petroleum ether) to afford 1.85 g (93%) of 132: mp 140.5-141.3° C. (acetone/n-heptane), [α]$_D^{20}$ +20.9 (c 0.29, CHCl$_3$). $^1$H NMR (400 MHz, CDCl$_3$): δ 0.77 (3H, s, H-18), 0.98 (3H, s, H-19), 4.11 (1H, m, H-3), 4.60-4.64 (2H, m, =CH$_2$). $^{13}$C NMR (101 MHz, CDCl$_3$): δ 162.23 (CH=), 100.73 (=CH$_2$), 67.29 (C-3), 54.80, 44.40, 40.20, 36.83, 36.12, 35.78, 35.46, 33.68, 30.17, 29.62, 28.01, 26.73, 26.35, 24.31, 24.07, 21.15, 18.69. IR spectrum (CHCl$_3$): 3616, 1028 (01-1); 1653 (C=C). MS: ESI m/z 311.3 (100%, M+Na). HR-MS (CI) m/z for C$_{20}$H$_{32}$O (M) calcd. 288.2453, found 288.2455. For C$_{20}$H$_{32}$O (288.5) calcd: 83.27% C, 11.18% H; found: 83.22% C, 11.34% H.

Example 107: (3S,5R,8S,9S,10S,13R,14S,17S)-10,13,17-Trimethylhexadecahydro-1H-cyclopenta[a]phenanthren-3-ol (133)

Compound 133 was prepared according to General Procedure V—Catalytic Hydrogenation from compound 132 (718 mg, 2.49 mmol). Compound 133 (723 mg, 99%): mp 145.6-146.2° C. (acetone/n-heptane), [α]$_D^2$+8.0 (c 0.27, CHCl$_3$). $^1$H NMR (400 MHz, CDCl$_3$): δ 0.53 (3H, s, H-18), 0.82 (3H, d, J=6.8, H-20), 0.97 (3H, s, H-19), 4.11 (1H, m, H-3). $^{13}$C NMR (101 MHz, CDCl$_3$): δ 67.36, 56.13, 45.34, 42.36, 40.30, 37.94, 36.86, 36.03, 35.45, 33.72, 30.40, 30.21, 28.01, 26.83, 26.64, 24.89, 24.11, 21.01, 13.99, 12.20. IR spectrum (CHCl$_3$): 3616, 1030 (OH); 1379 (CH$_3$). MS: ESI m/z 313.3 (100%, M+Na). HR-MS (ESI) m/z For C$_{20}$H$_{34}$ONa (M+Na) calcd. 313.25019, found 313.25046. For C$_{20}$H$_{34}$O (290.5) calcd: 82.69% C, 11.80% H; found: 82.53% C, 11.41% H.

Example 108: (3S,5R,8S,9S,10S,13R,14S,17S)-10,13,17-Trimethylhexadecahydro-1H-cyclopenta[a]phenanthren-3-yl 4-methylbenzenesulfonate (134)

Compound 134 was prepared according to General Procedure VIII—Tosylation from compound 133 (0.84 g, 2.89 mmol). Compound 134 (1.12 g, 87%): mp 112.6-113.8° C. (diethyl ether/n-heptane), [α]$_D^{20}$ +10.1 (c 0.30, CHCl$_3$). $^1$H NMR (400 MHz, CDCl$_3$): δ 0.51 (3H, s, H-18), 0.81 (3H, d, J=6.8, H-20), 0.95 (3H, s, H-19), 2.44 (3H, s, CH$_3$-tosylate), 4.83 (1H, m, H-3), 7.32 (2H, d, J=8.2, tosylate), 7.78 (2H, d, J=8.2, tosylate). $^{13}$C NMR (101 MHz, CDCl$_3$): δ 144.39 (C-1', tosylate), 134.92 (C-4', tosylate), 129.83 (C-1', C-5', tosylate), 127.75 (C-2', C-6', tosylate), 81.08 (C-3), 56.05, 45.30, 42.32, 40.61, 37.85, 36.98, 35.95, 34.95, 31.49, 30.35, 30.24, 26.43, 26.37, 25.95, 24.83, 23.79, 21.77, 20.95, 13.96, 12.17. IR spectrum (CHCl$_3$): 1175 (SO$_2$); 903 (C-OTs). MS: ESI m/z 467.3 (60%, M+Na), 911.7 (100%, 2M+Na). HR-MS (ESI) m/z for C$_{27}$H$_{40}$O$_3$NaS (M+Na) calcd: 467.25904, found 467.25907. For C$_{27}$H$_{40}$O$_3$S (444.67) calcd: 72.53% C, 9.07% H; found: 73.08% C, 9.33% H.

Example 109: (3R,5R,8S,9S,10S,13R,14S,17S)-3-Azido-10,13,17-trimethylhexadecahydro-1H-cyclopenta[a]phenanthrene (135)

Compound 135 was prepared according to General Procedure IX—Substitution of Tosylate Protecting Group with Alkali Azide from compound 134 (2.05 g, 4.62 mmol). Compound 135 (1.32 g, 91%): mp 59-59.5° C. (chloroform/methanol), [α]$_D^{20}$ +33.5 (c 0.31, CHCl$_3$). $^1$H NMR (400 MHz, CDCl$_3$): δ 0.52 (3H, s, H-18), 0.82 (3H, d, J=6.8, H-20), 0.94 (3H, s, H-19), 3.31 (1H, m, H-3). $^{13}$C NMR (101 MHz, CDCl$_3$): δ 61.45 (C-3), 55.88, 45.26, 42.65, 42.32, 41.02, 37.78, 36.19, 35.84, 34.95, 32.65, 30.38, 27.27, 26.90, 26.70, 24.88, 23.65, 20.73, 13.99, 12.18. IR spectrum (CHCl$_3$): 2942, 2869 (CH$_3$); 2094 (N$_3$). MS: CI m/z 316.3 (15%, M+1), 273.3 (100%, M−N$_3$), 287.3 (80%, M−N$_2$). HR-MS (CI) m/z for C$_{20}$H$_{33}$ (M−N$_3$) calcd. 273.2584, found 273.2582. For C$_{20}$H$_{33}$N$_3$ (315.3) calcd: 76.14% C, 10.54% H, 13.32% N; found: 76.48% C, 10.72% H, 13.05% N.

Example 109: (3R,5R,8S,9S,10S,13R,14S,17S)-10,13,17-Trimethylhexadecahydro-1H-cyclopenta[a]phenanthren-3-amine hydrochloride (136)

Azide 135 (693 mg, 2.20 mmol) was dissolved in methanol (25 ml) and EtOAc (12 ml) and 5% palladium on CaCO$_3$ (80 mg) was added to the reaction mixture. The mixture was hydrogenated for 18 h under a slight overpressure of hydrogen. The catalyst was then filtered off, the solvent was evaporated in vacuo and the residue was dissolved in min. amount of ethanol and poured into 5% aqueous HCl (100 ml). The product was extracted with chloroform (3×20 ml), combined organic extracts were dried, the solvent was evaporated in vacuo affording 432 mg (60%) of compound 136: mp 284-287° C. (chloroform/diethyl ether), [α]$_D^{20}$ +24.3 (c 0.30, CHCl$_3$). $^1$H NMR (400 MHz, CDCl$_3$): δ 0.51 (3H, s, H-18), 0.82 (3H, d, J=6.8, H-20), 0.95 (3H, s, H-19), 3.04 (1H, m, H-3). $^{13}$C NMR (101 MHz, CDCl$_3$) δ 55.45, 52.12, 45.09, 42.52, 42.27, 40.86, 37.55, 36.24, 35.42, 34.88, 31.86, 30.37, 27.00, 26.65, 26.37, 24.89, 23.61, 20.78, 13.97, 12.15. IR spectrum (CHCl$_3$): 2978 (CH$_3$), 2940 (N$^+$H$_3$ and CH$_2$). MS: ESI m/z 290.3 (100%, M−Cl). HR-MS (ESI) m/z for C$_{20}$H$_{36}$N (M−Cl) calcd: 290.28423, found 290.28425. For C$_{20}$H$_{36}$NCl (325.3) calcd: 73.69% C, 11.13% H, 4.30% N; found: 72.42% C, 11.13% H, 4.03% N.

Example 110: Ethyl 2-oxo-2-(((3R,5R,8S,9S,10S,13R,14S,17S)-10,13,17-trimethylhexadecahydro-1H-cyclopenta[a]phenanthren-3-yl)amino)acetate (137)

Compound 137 was prepared according to General Procedure XI—Reaction of C-3 Amino Group with Ethyl Chlorooxoacetate from compound 136 (210 mg, 0.64 mmol). Chromatography on silica gel (5% ethyl acetate in petroleum ether) afforded 93 mg (37%) of oily compound 137: $[\alpha]_D^{20}$ +41.7 (c 0.31, CHCl$_3$). $^1$H NMR (400 MHz, CDCl$_3$): δ 0.53 (3H, s, H-18), 0.82 (3H, d, J=6.8, H-20), 0.95 (3H, s, H-19), 1.38 (3H, t, J=7.1, CH$_3$-ethyl), 3.75-3.87 (1H, m, H-3), 4.34 (2H, q, J=7.1, CH$_2$-ethyl), 6.96 (1H, d, J=8.5, N—H). $^{13}$C NMR (101 MHz, CDCl$_3$) δ 161.22, 155.77, 63.30, 56.06, 50.22, 45.33, 42.51, 42.34, 41.12, 37.87, 36.18, 35.93, 34.85, 33.27, 30.38, 27.56, 27.12, 26.73, 24.88, 23.71, 20.73, 14.16, 13.99, 12.18. IR spectrum (CHCl$_3$): 2868 (CH$_3$); 1696 (C=O). MS: ESI m/z 412.4 (55%, M+Na), 801.9 (100%, 2M+Na). HR-MS (ESI) m/z for C$_{24}$H$_{39}$O$_3$NNa (M+Na) calcd: 412.28222, found 48.28233. For C$_{24}$H$_{39}$O$_3$N (389.3) calcd: 73.99% C, 10.09% H, 3.60% N; found: 74.41% C, 10.13% H, 3.21% N.

Example 111: Sodium 2-oxo-2-(((3R,5R,8S,9S,10S, 13R,14S,17S)-10,13,17-trimethylhexadecahydro-1H-cyclopenta[a]phenanthren-3-yl)amino)acetate (138)

A solution of NaOH (130 mg, 3.25 mmol) in MeOH (2 ml) was added dropwise at 0° C. to a stirred solution of protected amide 137 (93 mg, 0.24 mmol) in MeOH (3 ml). Stirring was continued at 10° C. for 2 h and then the reaction mixture was poured into water, the precipitated white solid was collected by filtration, washed with water and dried to afford 72 mg (79%) of amide 138: mp 330-334.6° C. (water), $[\alpha]_D^{20}$ insoluble in chloroform. $^1$H NMR (400 MHz, DMSO-d$_6$): δ 0.50 (3H, s, H-18), 0.80 (3H, d, J=6.8, H-20), 0.90 (3H, s, H-19), signal of C-3 is overlapped by the signal of DMSO. $^{13}$C NMR (101 MHz, DMSO-d$_6$): δ 165.10, 163.23, 55.25, 48.57, 44.70, 42.19, 41.85, 37.23, 36.02, 35.66, 34.42, 32.78, 29.90, 27.00, 26.84, 26.26, 24.46, 23.37, 20.22, 13.93, 11.95. IR spectrum (KBr): 1668 (C=O); 1522 (amide). MS: ESI m/z 360.3 (100%, M–Na). HR-MS (ESI) m/z for C$_{22}$H$_{34}$O$_3$N (M–Na) calcd: 360.25442, found 360.25392. For C$_{22}$H$_{34}$O$_3$NNa (383.2) calcd: 68.90% C, 8.94% H, 3.65% N; found: 67.85% C, 9.17% H, 3.24% N.

Example 112: Methyl 3-oxo-3-(3R,5R,8S,9S,10S, 13R,14S,17S)-10,13,17-Trimethylhexadecahydro-1H-cyclopenta[a]phenanthren-3-yl)amino)propanoate (139)

Compound 139 was prepared according to General Procedure X—Reaction of C-3 Amino Group with Methyl 3-Chloro-oxopropionate from compound 136 (202 mg, 0.52 mmol). Chromatography on silica gel (8% acetone in petroleum ether) afforded 258 mg (95%) of oily compound 139: mp >240° C. (acetone/n-heptane), $[\alpha]_D^{20}$ +33.7 (c 0.35, CHCl$_3$). $^1$H NMR (400 MHz, CHCl$_3$): δ 0.52 (3H, s, H-18), 0.81 (3H, d, J=6.8, H-20), 0.94 (3H, s, H-19), 3.30 (2H, s, COCH$_2$CO), 3.75 (3H, s, OCH$_3$), 3.80 (1H, m, H-3). $^{13}$C NMR (101 MHz, CHCl$_3$): δ 170.33 (COOMe), 163.72 (NHCO), 55.87, 52.36, 49.58, 45.17, 42.47, 42.18, 40.96, 40.92, 37.70, 36.04, 35.93, 34.72, 33.48, 30.24, 27.73, 27.01, 26.58, 24.72, 23.57, 20.57, 13.83, 12.00. IR spectrum (CHCl$_3$): 2939 (CH$_2$); 1723 (C=O); 1538, 1282 (amide and ester); 1344 (CH$_3$). MS: ESI m/z 388.3 (100%, M–1). BR-MS (ESI) m/z for C$_{24}$H$_{38}$O$_3$N (M–H) calcd: 388.28572, found 388.28503. For C$_{24}$H$_{39}$O$_3$N (389.3) calcd: 73.99% C, 10.09% H, 3.60% N; found: 73.58% C, 10.13% H, 3.28% N.

Example 113: 3-Oxo-3-(((3R,5R,8S,9S,10S,13R, 14S,17S)-10,13,17-trimethylhexadecahydro-1H-cyclopenta[a]phenanthren-3-yl)amino)propanoic acid (140)

A solution of NaOH (36 mg, 0.90 mmol) in H$_2$O (1.5 ml) was added at 0° C. to a stirred solution of amide 139 (250 mg, 0.64 mmol) in EtOH (15 ml). Stirring was continued at room temperature for 2 h and then the reaction mixture was poured into water, acidified with 5% aqueous HCl to pH-2 and precipitated amide 140 was filtered off, washed with water and dried. Compound 140 (32 mg, 92%): mp 147.8-149.4° C. (acetone/n-heptane), $[\alpha]_D^{20}$ +41.4 (c 0.30, CHCl$_3$: MeOH, 1.795:0.043). $^1$H NMR (400 MHz, CHCl$_3$): δ 0.51 (3H, s, H-18), 0.81 (3H, d, J=6.8, H-20), 0.93 (3H, s, H-19), 3.23 (2H, s, COCH$_2$CO), 3.77 (1H, m, H-3). $^{13}$C NMR (101 MHz, CDCl$_3$): δ 170.32 (COOH, CONH), 56.04, 50.07, 50.00, 45.30, 42.54, 42.29, 41.08, 37.85, 36.14, 35.96, 34.82, 33.31, 30.33, 27.56, 27.11, 26.71, 24.83, 23.67, 20.68, 13.93, 12.12. IR spectrum (KBr): 3500, 3436 (OH+ NH); 2936 (CH$_2$); 1736, 1727 (COOH). MS: ESI m/z 374.2 (85%, M–1), (100%, M–COOH). HR-MS (ESI) m/z for C$_{23}$H$_{36}$O$_3$N (M–H) calcd: 374.27007, found 374.26954. For C$_{23}$H$_{37}$O$_3$N (375.2) calcd: 73.56% C, 9.93% H, 3.73% N; found: 73.41% C, 10.17% H, 3.23% N.

Example 114: (3S,5R,8R,9S,10S,13R,14S)-17-((R)-Sec-butyl)-10,13-dimethylhexadecahydro-1H-cyclopenta[a]phenanthren-3-ol (143)

L-Selectride (1M in THF, 2.16 ml) was added dropwise under inert atmosphere to a cooled solution (–78° C.) of R-sec-butyl-5beta-androstan-3-one 142 (600 mg, 1.8 mmol) in anhydrous THF (50 ml). After 1 hr stirring at –78° C., water (5 ml) was added and the mixture was allowed to attain room temperature. Then, an aqueous solution of sodium hydroxide (6M, 5 ml) and an aqueous H$_2$O$_2$ solution (5 ml, 30%) were added, and the reaction mixture was stirred for 30 min. The mixture was poured into cold water, the product was extracted with EtOAc (2×50 ml) and water phase was extracted again with ethyl acetate (30 ml). Combined extracts were washed with an aqueous solution of hydrochloric acid (5%), saturated solution of sodium hydrogen carbonate, and brine. Solvent was dried over anhydrous sodium sulfate and evaporated. Column chromatography (10% EtOAc in petroleum ether) gave compound 143 (520 mg, 87%): mp 151-153° C. (acetone/n-heptane), $[\alpha]_D^{20}$ +17 (c 0.20, CHCl$_3$). $^1$H NMR (400 MHz, CDCl$_3$): δ 0.65 (3H, s, H-18), 0.81 (3H, t, J=7.4, H-23), 0.89 (3H, d, J=6.6, H-21), 0.97 (3H, s, H-19), 4.10 (1H, m, H-3). $^{13}$C NMR (101 MHz, CDCl$_3$): δ 67.36 (C-3), 56.82, 56.01, 42.84, 40.42, 39.92, 37.15, 36.76, 35.82, 35.33, 33.63, 30.03, 28.44, 28.34, 27.96, 26.83, 26.46, 24.43, 24.08, 21.27, 18.21, 12.23, 10.48. IR spectrum (CHCl$_3$): 3616, 1029 (OH); 1381 (CH$_3$). MS: ESI m/z 332.3 (100%, M), 3153 (78%, M–17), 313.3 (71%, M–19), 299.3 (24%, M–33). HR-MS (ESI) m/z for C$_{23}$H$_{40}$O (M) calcd: 332.3079, found 332.3082.

Example 115: (3S,5R,8R,9S,10S,13R,14S)-17-((R)-Sec-butyl)-10,13-dimethylhexadecahydro-1H-cyclopenta[a]phenanthren-3-yl 4-methylbenzenesulfonate (144)

Compound 144 was prepared according to General Procedure VIII—Tosylation from compound 143 (827 mg, 2.5 mmol). Compound 144 (1.1 g, 87%): mp 103-105° C. (benzene, decomposition), $[\alpha]_D^{20}$ +19.3 (c 0.32, CHCl$_3$). $^1$H NMR (400 MHz, CDCl$_3$): δ 0.62 (3H, s, H-18), 0.80 (3H, t, J=7.4, H-23), 0.87 (3H, d, J=6.5, H-21), 0.93 (3H, s, H-19), 2.44 (3H, s, CH$_3$-tosylate), 4.82 (1H, m, H-3), 7.32 (2H, m, tosylate), 7.78 (2H, d, J=8.3, tosylate). $^{13}$C NMR (101 MHz, CDCl$_3$): δ 144.40 (C-1', tosylate), 134.81 (C-4', tosylate), 129.83 (C-1', C-5'), 127.74 (C-2', C-6', tosylate), 81.10 (C-3), 56.69, 55.91, 42.79, 40.47, 40.19, 37.09, 36.84, 35.68, 34.77, 31.41, 30.08, 28.39, 28.28, 26.34, 26.22, 25.91, 24.32, 23.75, 21.79, 21.18, 18.17, 12.18, 10.46. IR spectrum (CHCl$_3$): 2940 (CH$_3$); 1175 (SO$_2$); 905 (C—OTs). ESI m/z 314.3 (100%, M–p-TsOH). HR-MS (ESI) m/z for C$_{30}$H$_{46}$O$_3$NaS (M+Na) calcd: 509.2590, found 509.2591.

Example 116: (3R,5R,8R,9S,10S,13R,14S)-3-Azido-17-((R)-sec-butyl)-10,13-dimethylhexadecahydro-1H-cyclopenta[a]phenanthrene (145)

Compound 145 was prepared according to General Procedure IX—Substitution of Tosylate Protecting Group with Alkali Azide from compound 144 (1.1 g, 2.3 mmol). Compound 145 (770 mg, 95%): mp 99-101° C. (benzene), [α]$_D^{20}$ +45.2 (c 0.10, CHCl$_3$). $^1$H NMR (400 MHz, CDCl$_3$): δ 0.64 (3H, s, H-18), 0.82 (3H, t, J=7.4, H-23), 0.89 (3H, d, J=6.5, H-21), 0.93 (3H, s, H-19), 3.31 (1H, tt, J=11.8, J=4.5, H-3). $^{13}$C NMR (101 MHz, CDCl$_3$): δ 61.44, 56.56, 55.91, 42.78, 42.55, 40.66, 40.24, 37.15, 35.96, 35.71, 34.80, 32.61, 28.42, 28.31, 27.26, 26.89, 26.51, 24.37, 23.61, 20.99, 18.19, 12.19, 10.48. IR spectrum (CHCl$_3$): 2942, 2868 (CH$_3$) 2094 (N$_3$). MS: CI m/z 330.3 (100%, M–N$_2$). FIR-MS (CI) m/z for C$_{23}$H$_{40}$N (M–N$_2$) calcd: 330.3155, found 330.3156.

Example 117: (3R,5R,8R,9S,10S,13R,14S)-17-((R)-Sec-butyl)-10,13-dimethylhexadecahydro-1H-cyclopenta[a]phenanthren-3-amine hydrochloride (146)

Compound 146 was prepared from compound 145 (770 mg, 2.2 mmol) analogously to the preparation of compound 136 affording 790 mg (98%) of 146: mp 301-302° C. (ethanol, decomposition), [α]$_D^{20}$ +30.8c (c 0.10, CHCl$_3$). $^1$H NMR (400 MHz, CDCl$_3$): δ 0.61 (3H, s, H-18), 0.78 (3H, t, J=7.4, H-23), 0.86 (3H, d, J=6.5, H-21), 0.91 (3H, s, H-19), 3.00 (1H, ddt, J=11.8, J=8.5, J=4.3, H-3). $^{13}$C NMR (101 MHz, CDCl$_3$): δ 56.48, 55.84, 51.50, 42.70, 42.25, 40.46, 40.16, 37.10, 35.89, 35.37, 34.62, 32.47, 28.35, 28.24, 26.98, 26.83, 26.42, 24.32, 23.47, 20.93, 18.10, 12.10, 10.41. IR spectrum (CHCl$_3$): 3437 (NH$_2$); 3192, 3011, 2786 (NH$_3^+$). MS: ESI m/z 330.3 (100%, M–HCl—H). HR-MS (ESI) m/z for C$_{23}$H$_{42}$N (M–Cl) calcd: 332.3317, found 332.3318. For C$_{23}$H$_{42}$NCl (368.0) calcd: 75.06% C, 11.50% H, 3.81% N; found: 74.77% C, 11.56% H, 3.67% N.

Example 118: Ethyl 2-(((3R,5R,8R,9S,10S,13R,14S)-17-((R)-sec-butyl)-10,13-dimethylhexadecahydro-1H-cyclopenta[a]phenanthren-3-yl)amino)-2-oxoacetate (147)

Compound 147 was prepared according to General Procedure XI—Reaction of C-3 Amino Group with Ethyl Chlorooxoacetate from compound 146 (178 mg, 0.48 mmol). Chromatography on silica gel (1-5% ethyl acetate in petroleum ether) afforded 107 mg (51%) of oily compound 147: [α]$_D^{20}$ +49.5 (c 0.34, CHCl$_3$). $^1$H NMR (400 MHz, CDCl$_3$): δ 0.64 (3H, s, H-18), 0.82 (3H, t, J=7.1, H-23), 0.89 (3H, d, J=6.5, H-21), 0.94 (3H, s, H-19), 1.38 (3H, t, J=7.1, CH$_3$-ethyl), 3.70-3.91 (1H, m, H-3), 4.34 (2H, q, J=7.1, CH$_2$-ethyl), 6.96 (1H, d, J=8.3, N—H). $^{13}$C NMR (101 MHz, CDCl$_3$): δ 161.21 (COOMe), 155.77 (CONH), 63.30 (C-3), 56.74, 56.01, 50.23, 42.81, 42.42, 40.74, 40.34, 37.15, 35.96, 35.80, 34.70, 33.25, 28.43, 28.32, 27.57, 27.12, 26.54, 24.37, 23.68, 21.00, 18.20, 14.16, 12.20, 10.49. IR (CHCl$_3$): 3539 (OH); 3405 (NH); 2935 (CH); 2867 (CH$_3$); 1696 (C=O). MS: ESI m/z 432.4 (11%, M+1), 454.4 (100%, M+Na), 885.8 (85%, 2M+Na). HR-MS (ESI) m/z for C$_{27}$H$_{46}$O$_3$N (M+H) calcd: 432.34722, found 432.34730.

Example 118: Sodium 2-(((3R,5R,8R,9S,10S,13R,14S)-17-((R)-sec-butyl)-10,13-dimethylhexadecahydro-1H-cyclopenta[a]phenanthren-3-yl)amino)-2-oxoacetate (148)

Compound 148 was prepared from compound 147 (95 mg, 0.22 mmol) analogously to the preparation of compound 138 affording 42 mg (45%) of 148: mp 182-184° C. (water, decomposition), [α]$_D^{20}$ +47.5 (c 0.14, DMSO). $^1$H NMR (400 MHz, DMSO-d$_6$): δ 0.61 (3H, s, H-18), 0.79 (3H, t, J=7.3, H-23), 0.87 (3H, d, J=6.9, H-21), 0.88 (3H, s, H-19), signal for H-3 is overlapped by the peak of DMSO. $^{13}$C NMR (101 MHz, DMSO-d$_6$): δ 167.01 (COONa), 16238 (CONH), 56.23, 55.49, 49.12, 42.29, 41.85, 39.85, 36.52, 35.63, 35.27, 34.18, 31.97, 27.89, 27.80, 26.66, 26.27, 26.05, 25.54, 23.89, 23.16, 20.47, 18.01, 11.94, 10.25. IR spectrum (KBr): 3425, 3415 (NH); 1760 (C=O); 1640 (CO$_2$). MS: ESI m/z 402.3 (100%, M–Na). HR-MS (ESI) m/z for C$_{25}$H$_{40}$O$_3$N (M–Na) calcd: 402.30137, found 402.30106.

Example 119: 3-(((3R,5R,8R,9S,10S,13R,14S)-17-((R)-Sec-butyl)-10,13-dimethylhexadecahydro-1H-cyclopenta[a]phenanthren-3-yl)amino)-3-oxopropanoic acid (149)

Compound 149 was prepared according to General Procedure X—Reaction of C-3 Amino Group with Methyl 3-Chloro-oxopropionate (affording the mixture of amides in an inseparable mixture of keto and enol forms), followed by the deprotection reaction analogously to the procedure for compound 140, from compound 146 (190 mg, 0.52 mmol). Compound 149 (65 mg, 30% after 2 steps): mp 163-165° C. (acetone/n-heptane), [α]$_D^{20}$ +53.3 (c 0.30, CHCl$_3$). $^1$H NMR (400 MHz, CHCl$_3$): δ 0.64 (3H, s, H-18), 0.82 (3H, t, J=7.4, H-23), 0.89 (3H, d, J=6.5, H-21), 0.94 (3H, s, H-19), 3.28 (2H, s, H-2'), 3.83 (H, tdt, J=12.1, J=8.5, J=4.4, H-3), 6.13 (d, H, J=7.8, NH). $^{13}$C NMR (101 MHz, CDCl$_3$): δ 168.32 (COO), 168.08 (CONH), 56.76, 56.03, 50.61, 42.80, 42.45, 40.75, 40.34, 38.43, 37.14, 35.93, 35.79, 34.70, 33.33, 28.43, 28.32, 27.64, 27.10, 26.55, 24.3, 23.65, 20.98, 18.20, 12.20, 10.50. IR spectrum (far): 3435, 1631 (NH); 1730, (C=O). MS: ESI m/z 833.6 (77%, 2M–1), 416.3 (100%, M–1), 372.3 (11%, M–COOH). HR-MS (ESI) m/z for C$_{26}$H$_{42}$O$_3$N (M–H) calcd: 416.31702, found 416.31619.

Example 120: (3S,5R,8R,9S,10S,13S,14S,Z)-17-ethylidene-10,13-dimethylhexadecahydro-1H-cyclopenta[a]phenanthren-3-ol and (3S,5R,8R,9S,10S,13S,14S,E)-17-ethylidene-10,13-dimethylhexadecahydro-1H-cyclopenta[a]phenanthren-3-ol, mixture of E/Z isomers (150)

A solution of Ph$_3$PEtBr (6.386 g, 17.2 mmol) in dimethyl sulfoxide (30 ml) was stirred at rt for 20 min under inert atmosphere and then NaH (50% in parafine oil, 688 mg, 17.2 mmol) was added. Stirring continued for 1 h, then a solution of 3beta-hydroxy-5beta-androstan-17-one (1.0 g, 2.9 mmol) in dimethyl sulfoxide (18 ml) was added and after 15 h of stirring at 60° C., aqueous solution of ammonium chloride was added. The product was extracted with chloroform; combined organic extracts were washed with brine, and dried. Solvents were evaporated and the residue was purified by chromatography on silica gel (5-10% ethyl acetate in petroleum ether) to afford 810 mg (78%) of compound 150 as mixture of E and Z isomers (1.5:8.5). Z-isomer: mp 157-158° C. (acetone/n-heptane), $[\alpha]_D^{20}$ +30.6 (c 0.32, CHCl$_3$).

$^1$H NMR (400 MHz, CDCl$_3$): δ 0.86 (3H, s, H-18), 0.97 (3H, s, H-19), 1.65 (3H, dt, $J_1$=7.2, $J_2$=2.0, H-21), 4.11 (1H, m, H-3), 5.11 (1H, qt, $J_1$=7.1, $J_2$=2.0, H-20). $^{13}$C NMR (101 MHz, CDCl$_3$): δ 150.64 (CH=CH—CH$_3$), 113.33 (CH=CH—CH$_3$), 67.31, 56.59, 44.63, 39.98, 37.61, 36.73, 35.34, 33.68, 31.66, 30.06, 28.01, 26.76, 26.30, 24.55, 24.02, 21.43, 17.04, 13.25. IR spectrum (CHCl$_3$): 3036 (=CH); 1673 (C=C); 995 (C—OH). MS: CI m/z 302.3 (50%, M). HR-MS (CI) m/z for C$_{21}$H$_{34}$O (M) calcd: 302.2610, found 302.2608.

Example 121: 2-((3R,5R,8R,9S,10S,13S,14S,Z)-17-ethylidene-10,13-dimethylhexadecahydro-1H-cyclopenta[a]phenanthren-3-yl)isoindoline-1,3-dione (151)

A mixture of triphenylphosphine (409 mg, 1.56 mmol), phathalimide (230 mg, 1.56 mmol) and compound 150 (360 mg, 1.2 mmol) in anhydrous THF (10 ml) was stirred under inert atmosphere in ice bath for 1 h. Then, diisopropyl azodicarboxylate (DIAD, 0.31 ml, 1.56 mmol) was added and stirring continued for 18 h at rt. Distilled water was added to quench the reaction, THF was evaporated and the reaction mixture was extracted with chloroform, washed with water, and dried. The solvent was evaporated and the residue was purified by chromatography on silica gel (3-5% ethyl acetate in petroleum ether) to afford 320 mg (63%) of phtalimide 151: mp 196-198° C. (methanol/dichlormethane) $[\alpha]_D^{20}$ +80.7 (c 0.24, CHCl$_3$). $^1$H NMR (400 MHz, CDCl$_3$): δ 0.88 (3H, s, H-18), 0.97 (3H, s, H-19), 1.66 (3H, dt, $J_1$=7.2, $J_2$=2.0, H-21), 4.19 (1H, m, H-3), 5.12 (1H, qt, $J_1$=7.2, $J_2$=2.0, H-20), 7.68-7.70 (2H, m), 7.79-7.82 (2H, m). $^{13}$C NMR (101 MHz, CDCl$_3$): δ 168.55 (2×C), 150.43 (CH=CH—CH$_3$), 133.78 (2×C), 132.12 (2×C), 122.95 (2×C), 113.16 (CH=CH—CH$_3$), 56.09, 51.28, 44.47, 43.09, 40.56, 37.31, 36.62, 35.36, 34.68, 31.50, 29.78, 27.07, 26.23, 24.41, 24.26, 23.40, 21.09, 16.95, 13.14. IR (CHCl$_3$): 3030 (=CH); 1678 (C=C). MS: CI m/z 431.3 (90%, M), 432.3 (100%, M+1). HR-MS (CI) m/z for C$_{29}$H$_{38}$O$_2$N (M+H) calcd: 432.2903, found 432.2904.

Example 121: (3R,5R,8R,9S,10S,13S,14S,Z)-17-Ethylidene-10,13-dimethylhexadecahydro-1H-cyclopenta[a]phenanthren-3-amine hydrochloride (152)

To a stirring solution of phtalimide 151 (115 mg, 0.26 mmol) in methanol (20 ml), hydrazine hydrate (85%, 3 ml) was added and reaction mixture was refluxed for 2 h. Then, aqueous solution of NaOH (6 N, 20 ml) was added and stirred for 0.5 h, extracted with dichloromethane, washed with water and dried. The residue was dissolved in min. amount of EtOH and poured into 5% aqueous HCl (50 ml). The hydrochloride amine was extracted with chloroform, combined organic extracts were dried and solvent was evaporated under reduced pressure to obtain oily amine 152 (85 mg, 94%): $[\alpha]_D^2$+47.8 (c 0.33, MeOH). $^1$H NMR (400 MHz, CDCl$_3$): δ 0.89 (3H, s, H-18), 1.01 (3H, s, H-19), 1.65 (3H, dt, $J_1$=7.2, $J_2$=2.0, H-21), 3.11 (1H, m, H-3), 5.11 (1H, qt, $J_1$=7.2, $J_2$=2.1 H-20). $^{13}$C NMR (101 MHz, MeOD): δ 151.25 (CH=CH—CH$_3$), 114.45 (CH=CH—CH$_3$), 57.74, 52.32, 45.58, 43.24, 41.86, 38.69, 36.63, 36.01, 35.64, 32.44, 32.37, 27.88, 27.32, 26.73, 25.38, 23.68, 22.07, 17.25, 13.40. IR spectrum (CHCl$_3$): 3436, 1617 (amine); 3013 (=CH); 1673 (C=C); 995 (C—OH). MS: ESI m/z 302.3 (80%, M–Cl). HR-MS (ESI) m/z for C$_{21}$H$_{36}$N (M–Cl) calcd: 302.28423, found 302.28433.

Example 121: Ethyl 2-(((3R,5R,8R,9S,10S,13S,14S,Z)-17-ethylidene-10,13-dimethylhexadecahydro-1H-cyclopenta[a]phenanthren-3-yl)amino)-2-oxoacetate (153)

Compound 153 was prepared according to General Procedure XI—Reaction of C-3 Amino Group with Ethyl Chlorooxoacetate from compound 152 (100 mg, 034 mmol). Chromatography on silica gel (3-5% ethyl acetate in petroleum ether) to afford of protected amide 153 (105 mg, 88%) as an inseparable mixture of keto and enol forms: $^1$H NMR (400 MHz, CDCl$_3$): δ 0.86 (3H, s, H-18), 0.96 (3H, s, H-19), 1.38 (3H, t, J=7.1, H-ethyl), 1.65 (3H, dt, $J_1$=7.2, $J_2$=2.0, H-21), 3.81 (1H, m, H-3), 4.34 (2H, q, J=7.1, H-ethyl), 5.12 (1H, qt, $J_1$=7.2, $J_2$=2.1, H-20), 6.96 (1H, d, J=6.9, H—NH).

Example 122: 2-(((3R,5R,8R,9S,10S,13S,14S,Z)-17-Ethylidene-10,13-dimethylhexadecahydro-1H-cyclopenta[a]phenanthren-3-yl)amino)-2-oxoacetic acid (154)

A solution of NaOH (110 mg, 2.75 mmol) in MeOH (2 ml) was added dropwise at 0° C. to a stirred solution of protected amide 153 (110 mg, 0.27 mmol) in MeOH (3 ml). Stirring was continued at 10° C. for 2 h and then the reaction mixture was poured into water, acidified with 5% aqueous HCl to pH-2 and extracted with ethyl acetate. The combined organic extracts were washed with brine, dried and the solvents were evaporated in vacuo to afford 90 mg (88%) of amide (E/Z, 2:8) 154: $^1$H NMR (400 MHz, CDCl$_3$): δ 0.86 (3H, s, H-18), 0.97 (3H, s, H-19), 1.65 (3H, dt, $J_1$=7.1, $J_2$=2.0, H-21), 3.76 (1H, m, H-3), 5.12 (1H, qt, $J_1$=7.2, $J_2$=2.1, H-20), 7.14 (1H, d, J=6.9, H—NH). $^{13}$C NMR (101 MHz, CDCl$_3$): δ 160.05 (COOH), 156.65 (CONH), 150.35 (CH=CH—CH$_3$), 113.50 (CH=CH—CH$_3$), 56.44, 51.27, 44.56, 42.43, 40.81, 37.48, 35.68, 35.48, 34.77, 33.06, 31.63, 27.40, 27.03, 26.37, 24.55, 23.61, 21.16, 17.02, 13.26. IR spectrum (CHCl$_3$): 3422, 1690 (amide); 3013 (=CH); 1669 (C=C); 1763 (C=O). MS: ESI m/z 396.4 (100%, M+Na). HR-MS (ESI) m/z for C$_{23}$H$_{36}$NO$_3$ (M+H) calcd: 374.26897, found 374.26910.

Example 122: 3-(((3R,5R,8R,9S,10S,13S,14S,Z)-17-Ethylidene-10,13-dimethylhexadecahydro-1H-cyclopenta[a]phenanthren-3-yl)amino)-3-oxopropanoic acid (155)

Compound 155 was prepared according to General Procedure X—Reaction of C-3 Amino Group with Methyl 3-Chloro-oxopropionate from compound 152 (150 mg, 0.44 mmol). Purification by column chromatography (3-5% ethyl acetate in petroleum ether) afforded the mixture of amides in an inseparable mixture of keto and enol forms (130 mg, 73%). A solution of NaOH (28 mg, 0.69 mmol) in H$_2$O (1.5 ml) was added at 0° C. to a stirred solution of protected amides (130 mg, 0.34 mmol) in THF (1.5 ml). Stirring was continued at room temperature for 2 h and then the reaction mixture was poured into water, acidified with 5% aqueous HCl to pH-2 and extracted with ethyl acetate. The combined organic extracts were washed with brine, dried and the solvents were evaporated in vacuo. The residue was chromatographed on silica gel (30% acetone in petroleum ether with 1% of TEA) to afford 69 mg (46%) of amide (E/Z, 2:8) 155: $^1$H NMR (400 MHz, CDCl$_3$): δ 0.85 (3H, s, H-18), 0.94 (3H, s, H-19), 1.64 (3H, dt, J$_1$=7.3, J$_2$=2.0, H-21), 3.23 (2H, s, COCH$_2$CO), 3.78 (1H, m, H-3), 5.11 (1H, qt, J$_1$=7.2, J$_2$=2.1, H-20), 7.14 (1H, d, J=6.9, H—NH). $^{13}$C NMR (101 MHz, CDCl$_3$): δ 167.91, 167.86, 150.48, 113.42, 56.47, 49.99, 45.32, 44.55, 42.46, 40.72, 37.51, 35.90, 35.46, 34.78, 33.39, 31.64, 27.67, 27.12, 26.42, 24.55, 23.65, 21.14, 16.99, 13.27. IR spectrum (CHCl$_3$): 1743 (C=O); 1662 (C=C); 1646, 1636, 1540 (amide). MS: ESI m/z 386.4 (20%, M−1), 342.4 (100%, M-COOH). HR-MS (ESI) m/z for C$_{24}$H$_{36}$NO$_3$ (M−H) calcd: 386.27007, found 386.26989.

The method used for the preparation of compound 8 was used in order to prepare additional compounds listed in Table 1:

TABLE 1

| Compound | Melting Point (° C.) | Optical Rotation [α]$_D$ (20° C.) | $^1$H-NMR peaks: H-18; H-19; H-3 | MS (m/z), Molecular ion without pyridinium (m/z = 80.1), Relative Intensity |
|---|---|---|---|---|
| Pyridinium (3R,5R,8R,9S,10S,13S,14S)-10,13-dimethyl-17-methylenehexadecahydro-1H-cyclopenta[a]phenanthren-3-yl 3-sulfate (116) | 155-157 | +41.6 | 0.73; 0.91; 4.44 | 311.3; 100% |
| Pyridinium (3R,5R,8S,9S,10S,13R,14S,17S)-10,13,17-trimethylhexadecahydro-1H-cyclopenta[a]phenanthren-3-yl 3-sulfate (117) | 174-175 | −21.6 | 0.51; 0.91; 4.46 | 369.2; 100% |
| Pyridinium (3R,5R,8S,9S,10S,13S,14R,17R)-10,17-dimethylhexadecahydro-1H-cyclopenta[a]phenanthren-3-yl 3-sulfate (118) | 152-155 | −0.5 | N/A; 0.85; 4.46 0.75 (17α-Me) | 355.2; 100% |
| Pyridinium (3R,5R,8S,9S,10S,13R,14R,17S)-10,17-dimethylhexadecahydro-1H-cyclopenta[a]phenanthren-3-yl 3-sulfate (119) | 155-158 | +26.9 | N/A; 0.85; 4.45 0.90 (17β-Me) | 355.2; 100% |
| Pyridinium (3R,5R,8S,9S,10S,13R,14S,17S)-17-ethyl-10,13-dimethylhexadecahydro-1H-cyclopenta[a]phenanthren-3-yl 3-sulfate (120) | 182-184 | +61.5 | 0.53; 0.86; 4.47 | 383.1; 100% |
| Pyridinium (3R,5R,8R,9S,10S,13S,14S,17R)-10,13-dimethyl-17-(prop-1-en-2-yl)hexadecahydro-1H-cyclopenta[a]phenanthren-3-yl 3-sulfate (121) | 169-172 | +42.0 | 0.52; 0.90; 4.45 | 395.2; 100% |
| Pyridinium (3R,5R,8R,9S,10S,13R,14S,17R)-17-isopropyl-10,13-dimethylhexadecahydro-1H-cyclopenta[a]phenanthren-3-yl 3-sulfate (122) | 190-194 | +26.2 | 0.62; 0.82; 4.46 | 397.2; 100% |
| Pyridinium (3R,5R,8R,9S,10S,13R,14S,17R)-17-((R)-sec-butyl)-10,13-dimethylhexadecahydro-1H-cyclopenta[a]phenanthren-3-yl 3-sulfate (123) | 186-188 | +13.8 | 0.62; 0.81; 4.46 | 411.4; 100% |
| Pyridinium (3S,3aS,5bR,7aR,9R,11aS,11bS,13aR)-3,11a-dimethylhexadecahydro-1H,3H-naphtho[2',1':4,5]indeno[1,7a-c]furan-9-yl 9-sulfate (124) | 118-121 | +30.5 | 3.37 a 3.63; 0.84; 4.47 | 397.1; 100% |
| Pyridinium (2R,4aS,4bS,6aS,10bR,12aR)-4a,6a-dimethyl-7-oxooctadecahydrochrysen-2-yl 2-sulfate (125) | 177-179 | −13.8 | 0.89; 1.05; 4.45 | 383.3; 100% |
| Pyridinium (3R,5R,8R,9R,10S,13S,14S)-13-methylhexadecahydro-1H-cyclopenta[a]phenanthren-3-yl 3-sulfate (126) | 192-194 | +19.0 | 0.66; N/A; 4.42 | 341.2; 100% |

TABLE 1-continued

| Compound | Melting Point (° C.) | Optical Rotation $[\alpha]_D$ (20° C.) | $^1$H-NMR peaks: H-18; H-19; H-3 | MS (m/z), Molecular ion without pyridinium (m/z = 80.1), Relative Intensity |
|---|---|---|---|---|
| Pyridinium (3R,5S,8R,9R,10S,13S,14S)-10,13-dimethylhexadecahydro-1H-cycopenta[a]phenanthren-3-yl 3-sulfate (127) | 167-169 | +8.2 | 0.66; 0.77; 4.74 | 458.3; 50% (M + Na − pyridinium) |
| Pyridinium (2S,4aR,4bR,8aS,10aS)-4a-methyltetradecahydrophenanthren-2-yl 2-sulfate (128) | 147-149 | −24.1 | N/A; 0.86; 4.47 | 301.0; 100% |

Biological Activity—Cell Cultures

Degree of inhibition of activated NMDA receptor by amphiphilic compounds was measured in vitro electrophysiologically on cultivated HEK293 cells (Human Embryonic Kidney 293 cells) 24-48 h after the transfection with DNA plasmids, coding NR1-1a and NR2B subunit of NMDA receptor. Transfected cells were identified by means of fluorescent green protein (GFP) fluorescence. Its genus was transfected together with the both receptor subunit genes.

Steroid-containing solutions were prepared from fresh solution (20 mmol·l$^{-1}$, of steroid dissolved in dimethyl sulfoxide, DMSO), which was added to the extracellular solution containing 1 mmol·l$^{-1}$ glutamic acid and 10 μmol·l$^{-1}$ of glycine. Identical concentrations of DMSO were added to all other extracellular solutions.

Current responses produced by extracellular application of glutamic acid solution (1 mmol·l$^{-1}$) were measured from the whole cell by patch-clamp technique, which is used for the study of transport of charged particles through model and also natural biological membranes. The currents were measured at membrane potential maintained at −60 mV and +60 mV. Steroid compounds studied lowered response amplitude elicited by glutamic acid. Application of 10 μmol·l$^{-1}$ steroid solution the mean inhibition effect reached 65-70%. It can be compared with 100 μmol·l$^{-1}$ of endogenous neurosteroid 5beta-pregnanolon-3alpha-yl 3-sulfate, which inhibited responses elicited by NMDA receptor to 67%.

Effect of Amphiphilic Compounds on Recombinant NMDA Receptors

HEK293 cells (American Type Culture Collection, ATTC No. CRL1573, Rockville, Md.) were cultivated in Opti-MEM® I media (Invitrogen) with addition of 5% fetal bovine serum at 37° C. and transfected with NR1-1a/NR2B/GFP plasmids, as described in the scientific literature (Neuroscience 151, 428-438, 2008). Same amounts (0.3 μg) of cDNA coding NR1, NR2 and GFP (green fluorescent protein) (pQBI 25, Takara, Japan) were mixed with 0.9 μl of Matra-A Reagent (IBA, Göttingen, Germany) and added to confluent HEK293 cells cultivated in v 24-pit cultivating plate. After trypsination, the cells were re-suspended in Opti-MEM® I containing 1% fetal bovine serum. Subsequently, 20 mmol·l$^{-1}$ MgCl$_2$, 1 mmol l$^{-1}$ D,L-2-amino-5-phosphonopentanoic acid, 3 mmol·l$^{-1}$ kynurenic acid was added to the mixture and cells were inoculated on the polylysine-coated glass plates having 25 mm in diameter. The following genes coding NMDA receptor subunits were used for transfection: NR1-1 a (GenBank accession No. U08261) and NR2B (GenBank accession No. M91562).

HEK293 Cultured cells were used for electrophysiological investigations with a latency of 16-40 h after transfection. Whole-cell currents were measured by patch-clamp amplifier (Axopatch 1D; Axon Instruments, Inc. Foster City, USA) after capacitance and serial resistance (<10 MΩ) compensation to 80-90%. Agonist-induced responses were filtered to 1 kHz (8-pole Bessel filter; Frequency Devices, Haverhill, USA), digitized with sampling frequency of 5 kHz and analyzed by pClamp version 9 software (Axon Instruments, USA). Micropipettes made of borosilicate glass were filled with intracellular solution, containing 125 mmol·l$^{-1}$ D-gluconic acid, 15 mmol·l$^{-1}$ cesium chloride, 5 mmol·l$^{-1}$ EGTA, 10 mmol·l$^{-1}$ HEPES buffer, 3 mmol·l$^{-1}$ magnesium chloride, 0.5 mmol·l$^{-1}$ calcium chloride and 2 mmol·l$^{-1}$ magnesium-salt of ATP (pH adjusted to 7.2 by cesium hydroxide solution). Extracellular solution (ECS) contained 160 mmol·l$^{-1}$ sodium chloride, 2.5 mmol·l$^{-1}$ potassium chloride, 10 mmol·l$^{-1}$ HEPES, 10 mmol·l$^{-1}$ glucose, 0.2 mmol·l$^{-1}$ EDTA a 0.7 mmol·l$^{-1}$ calcium chloride (pH adjusted to 7.3 by sodium hydroxide solution). Glycine was added to both testing and control solution. Moreover, bicuculline (10 μmol·l$^{-1}$) and tetrodotoxin (0.5 μmol·l$^{-1}$) was added to hippocampal cultures. Steroid-containing solutions were prepared from fresh solution (20 mmol·l$^{-1}$) of steroid dissolved in dimethyl sulfoxide (DMSO). Same concentrations of DMSO were used in all extracellular solutions. Control and experimental solutions were applied via microprocessor-controlled perfusion system with approx. rate of solution exchange in areas adjacent to cells reaching ~10 ms.

Current responses produced by 100 μmol·l$^{-1}$ of NMDA (in the case of hipocampal neurones), or by 1 mmol·l$^{-1}$ of glutamate (on recombinant NMDA receptors) were measured at membrane potential maintained at −60 mV. Similarly as described before, pregnanolone sulfate decreased the amplitude of responses elicited by NMDA. After application of 100 μmol·l$^{-1}$ of pregnanolone sulfate the mean inhibition effect reached 71.3±5.0% (n=5) on hipocampal neurones, and 67.2±8.2% (n=5) on recombinant NR1/NR2B receptors (J. Neurosci., 25, 8439-50, 2005). Our synthetic analogs of pregnanolone sulfate exhibited inhibitory effect (so that the level of inhibition was in the range of 30-70% maximum inhibition). Relative effect of steroid-induced inhibition was used for calculating IC$_{50}$. IC$_{50}$ value was calculated using formula RI=1−(1/1+([steroid]/IC$_{50}$)$^h$), where RI denotes relative effect of steroid-induced inhibition and h is a parameter of Hill's coefficient (1.2). IC$_{50}$ values are stated in the following table.

Newly synthesized analogs (8, 18, 19, 21, 22, 34, 35, 40, 49, 50, 51, 59, 61, 62, 64, 65, 67, 68, 69, 74, 76, 83, 85, 88, 93, 95, 97, 101, 106, 114, 116-124, 126, 127, 128, 130) have the same mechanism of action at the NMDA receptor as pregnanolone sulfate, but differ in their relative affinities for the NMDA receptor (see Table 2).

TABLE 2

| Compound | Mean % change ± SD | IC$_{50}$ (μmol) | Concentration (μmol · l$^{-1}$) |
|---|---|---|---|
| 3alfa,5beta-Pregnanolone sulfate Reference Compound | 67.2 ± 8.2 | 55 | 100 |
| Pyridinium (2R,4aS,4bS,8aR,10aR)-4a-methyltetradecahydrophenanthren-2-yl 2-sulfate (8) | 78.3 ± 5.5 | 28.3 | 100 |
| Pyridinium (2R,4aS,4bS,7S,8S,8aS,10aR)-7-(methoxymethyl)-4a,7,8-trimethyltetradecahydrophenanthren-2-yl 2-sulfate (18) | 60.5 ± 4.6 | 33 | 50 |
| 4-(((2R,4aS,4bS,7S,8S,8aS,10aR)-7-(Methoxymethyl)-4a,7,8-trimethyltetradecahydrophenanthren-2-yl)oxy)-4-oxobutanoic acid (19) | 47.4 ± 4.3 | 55 | 50 |
| Pyridinium (2R,4aS,7S,8S,10aR)-7-(methoxycarbonyl)-4a,7,8-trimethyltetradecahydrophenanthren-2-yl 2-sulfate (22) | 40.9 ± 6.1 | 74.6 | 100 |
| 4-(((2R,4aS,4bS,7R,8aS,10aR)-4a,7-Dimethyltetradecahydrophenanthren-2-yl)oxy)-4-oxobutanoic acid (34) | 27.0 ± 10 | 23.2 | 10 |
| Pyridinium (2R,4aS,4bS,7R,8aS,10aR)-4a,7-dimethyltetradecahydrophenanthren-2-yl 2-sulfate (35) | 85.0 ± 1.2 | 12 | 50 |
| Methyl (2S,4aS,4bS,7R,8aR,10aS)-2,4b-dimethyl-7-(sulfooxy)tetradecahydrophenanthren-2-carboxylate (40) | 14.4 ± 1.8 | 224 | 50 |
| Pyridinium (3R,5R,8S,9S,10S,13S,14S)-10,13-dimethylhexadecahydro-1H-cyclopenta[a]phenanthren-3-yl 3-sulfate (49) | 49.2 ± 6.6 | 2.1 | 2 |
| 2-(((3R,5R,8S,9S,10S,13S,14S)-10,13-Dimethylhexadecahydro-1H-cyclopenta[a]phenanthren-3-yl)oxy)-2-oxoethanoic acid (50) | 64.0 ± 7.0 | 6.3 | 10 |
| 2-(((3R,5R,8S,9S,10S,13S,14S)-10,13-Dimethylhexadecahydro-1H-cyclopenta[a]phenanthren-3-yl)oxy)-2-oxopropanoic acid (51) | 42.0 ± 14.0 | 15.5 | 10 |
| 2-(((3R,5R,10S,13S,14S)-10,13-Dimethylhexadecahydro-1H-cyclopenta[a]phenanthren-3-yl)amino)-2-oxoacetic acid (59) | 32.0 ± 5.0 | 23.2 | 10 |
| ((3R,5R,8S,9S,10S,13S,14S)-10,13-Dimethylhexadecahydro-1H-cyclopenta[a]phenanthren-3-yl)amino)-3-oxopropanoic acid (61) | 40.0 ± 5.7 | 15.4 | 10 |
| 4-(((3R,5R,8S,9S,10S,13S,14S)-10,13-Dimethylhexadecahydro-1H-cyclopenta[a]phenanthren-3-yl)oxy)-N,N,N-trimethyl-4-oxobutan-1-amonium chloride (62) | 34.0 ± 5.0 | 1.7 | 1 |
| 4-(((3R,5R,8R,9S,10S,13R,14S)-10,13-Dimethyl-2,3,4,5,6,7,8,9,10,11,12,13,14,15-tetradecahydro-1H-cyclopenta[a]phenanthren-3-yl)oxy)-4-oxobutanoic acid (64) | 45.9 ± 11.7 | 12.9 | 10 |
| 3-(((3R,5R,8R,9S,10S,13R,14S)-10,13-Dimethyl-2,3,4,5,6,7,8,9,10,11,12,13,14,15-tetradecahydro-1H-cyclopenta[a]phenanthren-3-yl)oxy)-3-oxopropanoic acid (65) | 44.0 ± 11.0 | 13.5 | 10 |
| 3-(((3R,5R,8R,10S,13S,14S)-10,13-Dimethyl-17-methylenehexadecahydro-1H-cyclopenta[a]phenanthren-3-yl)oxy)-3-oxopropanoic acid (67) | 53.0 ± 10.2 | 18.9 | 20 |
| 4-(((3R,5R,8R,9S,10S,13S,14S)-10,13-Dimethyl-17-methylenehexadecahydro-1H-cyclopenta[a]phenanthren-3-yl)oxy)-4-oxobutanoic acid (68) | 24.2 ± 14.3 | 18.8 | 5 |
| 4-(((3R,5R,8R,9S,10S,13S,14S)-10,13-Dimethyl-17-methylenehexadecahydro-1H-cyclopenta[a]phenanthren-3-yl)oxy)-4-oxopentanoic acid (69) | 62.9 ± 5.1 | 11.6 | 20 |
| 2-((3R,5R,8R,9S,10S,13S,14S)-10,13-Dimethyl-17-oxohexadecahydro-1H-cyclopenta[a]phenanthren-3-yl)acetic acid (74) | 58.6 ± 9.3 | 38.7 | 50 |
| 2-(((3R,5R,8R,9S,10S,13S,14S)-10,13-Dimethyl-17-methylenehexadecahydro-1H-cyclopenta[a]phenanthren-3-yl)oxy)-N,N,N-trimethyl-2-oxoethan-1-ammonium chloride (76) | 50.0 ± 10.0 | 51.7 | 50 |
| 3-(((3R,5R,8R,9S,10S,13S,14S,Z)-17-Ethylidene-10,13-dimethylhexadecahydro-1H-cyclopenta[a]phenanthren-3-yl)oxy)-3-oxopropanoic acid (83) | 60.5 ± 10.1 | 20.7 | 30 |
| 5-(((3R,5R,8R,9S,10S,13S,14S,Z)-17-Ethylidene-10,13-dimethylhexadecahydro-1H-cyclopenta[a]phenanthren-3-yl)oxy)-5-oxopentanoic acid (85) | 59.4 ± 7.8 | 38.4 | 50 |
| 3-(((3R,5R,8R,9S,10S,13S,14S,17R)-10,13-Dimethyl-17-(prop-1-en-2-yl)hexadecahydro-1H-cyclopenta[a]phenanthren-3-yl)oxy)-3-oxopropanoic acid (88) | 46.0 ± 0.9 | 11.8 | 10 |
| Pyridinium (3R,5R,8R,9S,10S,13S,14S,17S)-17-iodo-10,13-dimethylhexadecahydro-1H-cyclopenta[a]phenanthren-3-yl 3-sulfate (93) | 90.5 ± 2.2 | 0.8 | 5 |
| Pyridinium (3R,5R,8R,9S,10S,13S,14S)-17,17-difluoro-10,13-dimethylhexadecahydro-1H-cyclopenta[a]phenanthren-3-yl 3-sulfate (95) | 61.2 ± 5.1 | 7.0 | 10 |

TABLE 2-continued

| Compound | Mean % change ± SD | IC$_{50}$ (µmol) | Concentration (µmol · l$^{-1}$) |
| --- | --- | --- | --- |
| Pyridinium (3R,5R,8R,9S,10S,13S,14S,17S)-10,13-dimethylhexadecahydrospiro[cyclopenta-[a]phenanthren-17,2'-oxiran]-3-yl 3-sulfate (97) | 78.0 ± 8.9 | 45 | 100 |
| Pyridinium (2R,4aS,4bS,6aS,10bS,6aS,12aR)-4a,6a-dimethyloctadecahydrochrysen-2-yl 2-sulfate (101) | 69.1 ± 5.9 | 2.3 | 5 |
| (4S)-4-Amino-5-(((2R,4aS,4bS,6aS,10bS,12aR)-4a,6a-dimethyloctadecahydrochrysen-2-yl)oxy)-5-oxopentanoic acid (106) | 48.7 ± 6.3 | 10.6 | 10 |
| Pyridinium (3R,5R,8S,9S,10S,13R,14S)-10,13-dimethyl-16-methylenhexadecahydro-1H-cyclopenta[a]phenanthren-3-yl 3-sulfate (114) | 59.1 ± 3.8 | 2.1 | 3 |
| Pyridinium (3R,5R,8R,9S,10S,13S,14S)-10,13-dimethyl-17-methylenehexadecahydro-1H-cyclopenta[a]phenanthren-3-yl 3-sulfate (116) | 68.3 ± 4.3 | 1.4 | 3 |
| Pyridinium (3R,5R,8S,9S,10S,13R,14S,17S)-10,13,17-trimethylhexadecahydro-1H-cyclopenta[a]phenanthren-3-yl 3-sulfate (117) | 73.1 ± 6.7 | 1.1 | 3 |
| Pyridinium (3R,5R,8S,9S,10S,13S,14R,17R)-10,17-dimethylhexadecahydro-1H-cyclopenta[a]phenanthren-3-yl 3-sulfate (118) | 68.0 ± 7.8 | 1.5 | 3 |
| Pyridinium (3R,5R,8S,9S,10S,13R,14R,17S)-10,17-dimethylhexadecahydro-1H-cyclopenta[a]phenanthren-3-yl 3-sulfate (119) | 81.1 ± 2.1 | 0.7 | 3 |
| Pyridinium (3R,5R,8S,9S,10S,13R,14S,17S)-17-ethyl-10,13-dimethylhexadecahydro-1H-cyclopenta[a]phenanthren-3-yl 3-sulfate (120) | 84.9 ± 3..6 | 0.5 | 3 |
| Pyridinium (3R,5R,8R,9S,10S,13S,14S,17R)-10,13-dimethyl-17-(prop-1-en-2-yl)hexadecahydro-1H-cyclopenta[a]phenanthren-3-yl 3-sulfate (121) | 71.7 ± 8.0 | 0.4 | 1 |
| Pyridinium (3R,5R,8R,9S,10S,13R,14S,17R)-17-isopropyl-10,13-dimethylhexadecahydro-1H-cyclopenta[a]phenanthren-3-yl 3-sulfate (122) | 59.6 ± 18.8 | 2.0 | 3 |
| Pyridinium (3R,5R,8R,9S,10S,13R,14S,17R)-17-((R)-sec-butyl)-10,13-dimethylhexadecahydro-1H-cyclopenta[a]phenanthren-3-yl 3-sulfate (123) | 46.2 ± 2.3 | 11.7 | 10 |
| Pyridinium (3S,3aS,5bR,7aR,9R,11aS,11bS,13aR)-3,11a-dimethylhexadecahydro-1H,3H-naphtho[2',1':4,5]indeno[1,7a-c]furan-9-yl 9-sulfate (124) | 69.1 ± 4.0 | 51 | 100 |
| Pyridinium (3R,5R,8R,9R,10S,13S,14S)-13-methylhexadecahydro-1H-cyclopenta[a]phenanthren-3-yl 3-sulfate (126) | 68.3 ± 7.4 | 5.4 | 10 |
| Pyridinium (3R,5S,8R,9R,10S,13S,14S)-10,13-dimethylhexadecahydro-1H-cyclopenta[a]phenanthren-3-yl 3-sulfate (127) | 34.0 ± 5.0 | 1.7 | 3 |
| Pyridinium (2S,4aR,4bR,8aS,10aS)-4a-methyltetradecahydrophenanthren-2-yl 2-sulfate (128) | 58.0 ± 2.0 | 36.3 | 50 |
| (4S)-4-Amino-5-(((3R,5R,8S,9S,10S,13S,14S)-10,13-dimethylhexadecahydro-1H-cyclopenta[a]phenanthren-3-yl)oxy)-5-oxopentanoic acid (130) | 36.7 ± 7.0 | 1.6 | 1 |
| 1-(3R,5R,8S,9S,10S,13S,14S)-10,13-Dimethylhexadecahydro-1H-cyclopenta[a]phenanthren-3-yl)-5-oxopyrrolidine-3-carboxylic acid (131) | 34.7 ± 7.2 | 17.7 | 10 |
| Sodium 2-oxo-2-(((3R,5R,8S,9S,10S,13R,14S,17S)-10,13,17-trimethylhexadecahydro-1H-cyclopenta[a]phenanthren-3-yl)amino)acetate (138) | 17.5 ± 1.8 | 3.7 | 1 |
| 3-Oxo-3-(((3R,5R,8S,9S,10S,13R,14S,17S)-10,13,17-trimethylhexadecahydro-1H-cyclopenta[a]phenanthren-3-yl)amino)propanoic acid (140) | 17.8 ± 6.5 | 3.9 | 1 |
| Sodium 2-(((3R,5R,8R,9S,10S,13R,14S)-17-((R)-sec-butyl)-10,13-dimethylhexadecahydro-1H-cyclopenta[a]phenanthren-3-yl)amino)-2-oxoacetate (148) | 7.3 ± 3.0 | 9.4 | 1 |
| 3-(((3R,5R,8R,9S,10S,13R,14S)-17-((R)-Sec-butyl)-10,13-dimethylhexadecahydro-1H-cyclopenta[a]phenanthren-3-yl)amino)-3-oxopropanoic acid (149) | 33.6 ± 6.1 | 18.3 | 10 |
| 2-(((3R,5R,8R,9S,10S,13S,14S,Z)-17-Ethylidene-10,13-dimethylhexadecahydro-1H-cyclopenta[a]phenanthren-3-yl)amino)-2-oxoacetic acid (153) | 5.7 ± 2.3 | 11.7 | 1 |
| 3-(((3R,5R,8R,9S,10S,13S,14S,Z)-17-Ethylidene-10,13-dimethylhexadecahydro-1H-cyclopenta[a]phenanthren-3-yl)amino)-3-oxopropanoic acid (154) | 54.4 ± 5.0 | 8.7 | 10 |

Experiments In Vivo

In the Experimental Part 1 were used adults (30-35 g) male laboratory mice, strain CD-1 from Velaz facility, Czech Republic. Mice were housed in plastic boxes with a 12-hour light cycle (lights on at 7:00 pm). Mice had free access to food and water.

In the Experimental Part 2 were used adult (3 months old, 300-400 g) male rat Long-Evans strain. The animals come from herds Institute of Physiology ASCR. The rats were housed in clear plastic boxes with the same light cycle as in mice. Animals had free access to food and water. All experiments were carried out in the light of clay. All experiments were carried out in accordance with the Law on protection of animals against cruelty.

Used Chemicals

Amphiphilic steroid compounds were dissolved in a solution of 3 g (2-hydroxypropyl)-β-cyclodextrin (CDX, Sigma-Aldrich) and 157 mg of citric acid (3-hydroxy-penta-1,3,5-tricarboxylic acid, Sigma-Aldrich) in 30 ml of distilled water, the pH was adjusted to 7.4 using sodium hydroxide (NaOH, Sigma-Aldrich). Thus there were prepared solutions of the four steroids for application rates of 0.1, 1, 10 and 100 mg/kg.

The efficacy of the studied compounds was compared to known NMDA antagonist is memantine (Sigma-Aldrich) at a dose of 5 mg/kg in rats, ketamine (Vétoquinol) at 10 mg/kg and dizocilpine (MK-801) (Sigma-Aldrich) at a dose of 0.3 mg/kg in mice. These three compounds were dissolved in saline (B Braun).

The anesthetized rats were used in operations isoflurane (3.5%, Baxter). To recall excitotoxic lesion of the dorsal hippocampus was applied 0.05 mol·l$^{-1}$ solution of NMDA (Sigma-Aldrich) in 0.4 mol·l$^{-1}$ phosphate buffer solution prepared by mixing 356 g $Na_2HPO_4 \cdot 12H_2O$ ($M_w$ 358.14) in 4.2 l of distilled water and a solution of 62.4 g $NaHPO_4 \cdot 2H_2O$ ($M_w$ 156.01) in 0.8 l of distilled water. The pH of the resulting solution of NMDA was adjusted to 7.4 with NaOH.

Devices

In operations were used two-arm stereotactic apparatus (Kopf Instruments) and microinfusion pump (TSE Systems). The anesthesia was used vaporizer for isoflurane (AE Services & Supplies) and inhalation mask for rats.

Special apparatus used in behavioral tasks will together with the procedure in the experiment are described below.

Experimental Part 1

Laboratory mouse was chosen as a model organism for this experiment. The following experiments were performed as described in Front Behav. Neurosci. 8, 130 (2014).

Primary Behavioral Testing

The purpose of the primary behavioral testing was quickly determined the effect of compounds on CNS dependent functions and any signs of toxicity. A simplified modification Irwin test was selected with respect to the behavioral profile of NMDA receptor antagonists. Mice were tested individually. The study drug was administered intraperitoneally (Table 3) at a dose of 1 mg/kg. The control group consisted of individuals that received the CDX solution or saline.

Elevated Plus Maze

The elevated plus maze (EPM) experiment was used to determine the effect of compounds on anxiety of animals at a dose of 1 mg/kg. Two control groups of animals were used to which was applied physiological saline and CDX solution, respectively. A noncompetitive NMDA receptor antagonist—ketamine (10 mg/kg) was given to a comparative group. The compounds were administered to mice intraperitoneally 30 minutes before testing in the EPM.

Open Field

The substances at dose 0.1-100 mg/kg were administered before the test to mice intraperitoneally. As controls were used intact mice and mice that received CDX solution. Also, MK-801 (0.3 mg/kg) was used for comparison of effects of noncompetitive antagonist of NMDA receptors. From the experiment was evaluated overall track anywhere in the arena as an indicator of locomotor activity. In addition, it was judged a ten-minute segments track during each experiment. Based on these values, it was possible to determine the latency time of onset of action and changes in locomotor activity over time.

In this arrangement, the sedative effect of the studied compounds at the highest dose was evaluated. Mice were administered the relevant substance at dose 100 mg/kg to demonstrate the sedative effect, or vice versa and unexpected toxic effects of high doses of the studied compounds. Over time was monitored locomotor activity and possible changes characterized by tremor, ataxia, restlessness, or sedation or general anesthesia (absence of response to stimuli, decreased muscle tone).

Forced Swimming

This assay was used to monitor the antidepressant effect. Animals float 6 minutes in acrylic cylinder in water at 24° C. A period of immobility is evaluated. The reduction is a manifestation of anti-depressant properties of drugs.

Passive Avoidance Test

Aversive motivated memory test was evaluated on the basis of latency input into the preferred, but unpleasant sensation associated with delivery device.

Experimental Part 2

In this experiment, the neuroprotective effects were evaluated for amphiphilic steroid compounds. The procedure was performed according to Neuropharmacology 61, 61-68 (2011)

Bilateral Excitotoxic Lession of Dorsal Hippocampus

The rats were randomly divided into eleven groups. The control group included operated animals, which were injected by phosphate buffer pH 4.7 into the hippocampus. In the second group, the animals had NMDA lesions of the hippocampus. The animals of the third group were applied clinically used NMDA antagonist memantine at a dose of 5 mg/kg after NMDA lesion. The other groups were administered the compounds at a dose of 1 mg/kg.

Aloletické Active Place Avoidance (AAPA)

The test was performed in rotating arena with prohibited sector in the form of a circular sector (60°). If the rat entered the sector, its limbs received weak electrical impulse. If the animal did not left the sector, the pulse was repeated every 1200 ms.

Test memory and spatial cognition in rats using AAPA was evaluated over four sessions, which are in healthy rats sufficient to achieve asymptotic level (Behav. Brain. Res. 189, 139-144 (2008)). To evaluate memory and spatial cognition was used data from the fourth session, and the number of entries into the forbidden sector and the maximum avoidance sector. These data were analyzed off-line (using TrackAnalysis, Biosignals Group) and then statistically evaluated. After the experiment, the localization of the lesion was histologically verified.

Statistical Evaluation

Data were analyzed using the non parametric test of Maim Whitney criteria using the GraphPad. The difference was considered significant for $p<0.05$, for a non-significant tendency then for $0.05<p<0.075$. The graph shows averages, error bars represent standard error of the mean (SEM).

Results of In Vivo Experiments
Experimental Part 1

The primary behavioral screening did not reveal any abnormal behavior after administration of the studied compounds (1 mg/kg), see Table 3. Reflexes of mice and their balance and motor coordination were normal. We did not observed statistically significant differences between groups.

The anxiety rate was evaluated based on the number of entries into the open arms and the total time spent in the open arms of the maze. It has been showed that after administration androstane glutamate at 1 mg/kg significantly increased both parameters as compared with both control groups (saline and CDX solution, respectively), which demonstrates the anxiolytic effects of androstane glutamate. The highest values of both monitored parameters of all the test compounds were achieved after administration androstane glutamate at 1 mg/kg.

Application of androstane glutamate at dose 10 mg/kg induced a significant increase in total time spent in the open arms as compared to animals of both EPM control groups, number of entries into the open arms was not significantly altered as compared to the control groups (saline, CDX). There was no significant difference between the two control groups at any of studied parameters.

The antidepressant effect was studied similarly in a forced swimming test. The efficacy was evaluated as a decrease flotation in mice after administration of the studied compounds, as reference substance was used ketamine, which in accordance with the literature showed antidepressant effect. Similarly as in the previous screenings was demonstrated significant decrease of flotation and longer latency to the first flotation by androstane glutamate after administration at a dose of 1 mg/kg.

Effect of studied compounds on spontaneous locomotor activity of animals was evaluated by the total path in the open field test over a period of 50 minutes. There was not a significant difference among the overall pathway of mice in both control groups (intact animals and CDX).

Administration of dizocilpine (0.3 mg/kg) resulted in significant increases in overall pathway as compared with the control group that was administered with a solution of CDX. There was observed a tendency to increasement as compared with intact animals (p=0.0653).

Application of substances 67, 68, 69, 81, 84, 106, 124 and 130 at a dose 10 and 100 mg/kg resulted in a significant reduction of pathway as compared with intact mice. At lower doses it was not (unlike groups with dizocilpine) observed hyperlocomotion. These results suggest a low risk of induction of side effects typical for the NMDA antagonist upon administration of the above mentioned controlled substances. The values of pathway in each ten-minute-sections experiment are in direct connection with the changes in locomotor activity over time. For statistical comparison of these changes, we used the calculation of area under the curve, which is a direct expression of the time course of changes in the foregone track. Calculation of the area under the curve was always done for each observation, and then the resulting data were statistically compared between the groups.

The results indicate that locomotion of intact animal was gradually reduced. The trend was similar in the group of mice after the administration of CDX. There was no significant difference of the locomotor activity of the intact animals and animals injected with CDX solution. In the case of dizocilpine (0.3 mg/kg) on the other hand there has been a gradual increase in locomotor activity. The level of locomotion (at the highest and relatively stable level) kept between the 20th and 50th minutes after administration. The total locomotor activity after administration of dizocilpine was also significantly higher as compared with two control groups.

Application of compounds 67, 68, 69, 81, 84, 106, 124 and 130 in the higher dose of 10 resp. 100 mg/kg induced a significant decrease in locomotor activity. The slight decrease in locomotion was observed already after 10 min after administration. Between the 20th and 40th minute, the locomotor activity was minimal, the animals showed significant signs of sleepiness and overall sedation, the effect was most pronounced for androstan glutamate.

Mild memory impairment in the passive avoidance test was observed only for the substance 84 used in a dose of 1 mg/kg. For other substances, no adverse effects on the formation of memory traces was observed, which is described in the literature for a number of NMDA antagonists.

Experimental Part 2

For reasons of ethical imperative to reduce the number of laboratory animals used in the experiment, only the substances with the largest result were selected to the next phase.

Active Allotetic Place Avoidance:

NMDA lesion of the dorsal hippocampus in rats induced cognitive deficit, manifested as a significant increase in the number of entries into the forbidden areas and a significant reduction of the maximum time avoiding sector in the fourth session of AAPA compared with the control group. In rats, which were administered after surgery of compound 67 and 130 at a dose of 1 mg/kg, there was a significant reduction in the number of inputs into the forbidden sector during the fourth session of the AAPA group compared to NMDA. Both drugs also significantly increased the maximum time avoiding the sector during the fourth session due to NMDA. These findings point to mitigate cognitive deficits and therefore neuroprotective activity of the compounds 67 and 130. Furthermore, we observed a tendency to increase the maximum time avoidance and a reduced number of entries into the forbidden areas in rats with application of compounds 68, 81 and 84 and clinically used memantine. Cognitive deficit was most pronounced in the group of NMDA. Conversely, the best test cognitive results showed controlling animals.

TABLE 3

Summarized Results

| Compound | Sedative Effect The Rapid Onset of Sedation at a Dose of 100 mg/kg | Behavioural Test No Evidence of Toxicity | Open Field Test No Evidence of Hyperlocomotion | Passive Avoidance Test No Memory Violation | NMDA lession Improvement in Cognition in AAPA after NMDA Lession | Forced Swimming Test Reduced Floating |
|---|---|---|---|---|---|---|
| 67 | + | + | + |  | ++++ |  |
| 68 | + | + | + | + | +++ |  |
| 69 | + | + | + |  | −/+ |  |
| 81 | + | + | + | + | ++ | − |
| 84 | + | + | + | −/+ | ++ |  |
| 106 | − | + | + | + | − | − |
| 124 | − | + | + | −/+ | − | − |
| 130 | + | + | + | + | +++++ | + |

− the desired effect was not observed,
−/+ the desired effect was insufficient,
+ the desired effect was observed

INDUSTRIAL APPLICABILITY

The compounds of the present invention are industrially manufacturable and usable for the treatment of many diseases of the central nervous system such as: hypoxic and ischemic damage of CNS, stroke and other pathological changes caused hyperexcitation; neurodegenerative changes and disorders; affective disorders, depression, post-traumatic stress disorder, and diseases related to stress; schizophrenia and other psychotic disorders; pain, hyperalgesia, disturbance in the perception of pain; addiction; multiple sclerosis and other autoimmune diseases; epilepsy and other disorders manifesting hyperplazic seizures and changes in the central nervous system, tumors of the central nervous system, including gliomas.

The invention claimed is:
1. An amphiphilic compound with tetradecahydrophenanthrene skeleton of general formula I,

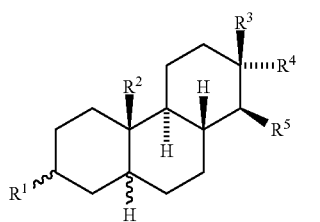

(I)

wherein
$R^1$ is selected from the group comprising (—$OSO_3pyH$), (—$OSO_3Na$), (—$OSO_3H$), NaOOC—$R^6$—C($R^7$)—$R^8$—, HOOC—$R^6$—C($R^7$)—$R^8$—, HOOC—C($R^7$)—$R^8$—, or $R^9$—$R^{10}$—C(R)—$R^{12}$—, where
$R^6$ represents straight or branched $C_1$ to $C_6$ alkylene or $C_2$ to $C_6$ alkenylene chain, unsubstituted or substituted with one or more halogen atoms or amino group or amino group protected by protecting groups,
or $R^6$ means trivalent —CH($CH_2$-$)_2$ alkylene that forms with the carbon carrying $R^7$ and with $R^8$ being nitrogen a five-membered ring;

$R^7$ represents atom of oxygen, nitrogen or sulphur bound by double bond, or two atoms of hydrogen,
$R^8$ represents an at least divalent atom,
$R^9$ represents a cationic group selected from guanidinyl derivatives of formula (a),

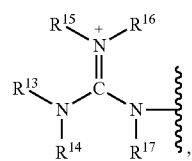

(a)

and quaternary ammonium groups of formula (b)

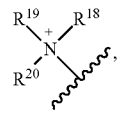

(b)

wherein $R^{13}$ to $R^{20}$ are selected from hydrogen atoms, linear or branched $C_1$ to $C_6$ alkyl, linear or branched $C_2$ to $C_6$ alkenyl,
$R^{10}$ represents straight or branched $C_1$ to $C_6$ alkylene or $C_2$ to $C_6$ alkenylene, wherein the alkylene and alkenylene are unsubstituted or substituted by 1 to 10 halogen atoms or by amino group which is primary or substituted by linear or branched $C_1$ to $C_4$ alkyl;
$R^{11}$ represents atom of oxygen, nitrogen or sulphur bound by double bond, or two atoms of hydrogen, and
$R^{12}$ is selected from the group comprising oxygen, nitrogen and carbon atoms, and when $R^{12}$ is carbon or nitrogen, its further valences are occupied by hydrogen or hydrogens, while any of hydrogen is optionally replaced by $C_1$ to $C_4$ alkyl or $C_2$ to $C_4$ alkenyl;
$R^2$ represents hydrogen atom or methyl;

R³ represents a) hydrogen atom, and then
  i) R⁴ and R⁵ are hydrogen atoms, or
  ii) one of R⁴ and R⁵ represents hydrogen atom and the other one represents a straight or branched $C_1$ to $C_6$ alkyl or $C_2$ to $C_6$ alkenyl chain, optionally substituted by 1 to 13 halogen atoms in case of said alkyl and by 1 to 9 halogen atoms in case of said alkenyl, or by atom of oxygen or sulphur bound by a double bond, while one of the methylene groups in the chain is optionally replaced by oxygen or sulphur atom; or
  b) straight or branched $C_1$ to $C_6$ alkyl or $C_2$ to $C_6$ alkenyl, optionally substituted by 1 to 13 halogen atoms in case of alkyl or by 1 to 9 halogen atoms in case of alkenyl, or by atom of oxygen or sulphur bound by a double bond, while one of the methylene groups in the chain is optionally replaced by oxygen or sulphur atom, and then R⁴ and R⁵ are hydrogen atoms, or
  c) $C_5$ or $C_6$ alicyclic or aromatic ring, while carbon atoms are optionally substituted by 1 to 8 atoms of halogen in case of $C_5$ alicyclic ring, or 1 to 10 halogen atoms in case of $C_6$ alicyclic ring or by 1 to 4 halogen atoms in case of $C_5$ aromatic ring or 1 to 5 halogen atoms in case of $C_6$ aromatic ring; and then
    i) R⁵ is selected from the group comprising hydrogen atom, linear or branched $C_1$ to $C_6$ alkyl, linear or branched $C_2$ to $C_6$ alkenyl, wherein said alkyl or alkenyl is optionally substituted by 1 to 13 halogen atoms in case of said alkyl and by 1 to 9 halogen atoms in case of said alkenyl, or by double-bond-bound atom of oxygen or sulphur, while one of the methylene groups in the chain is optionally replaced by oxygen or sulphur atom, or
    ii) R⁴ and R⁵ represent alkylene or alkenylene substituent —(CH$_m$)$_n$—, where n=3-4, m=1-2, forming with the parent carbon atoms of the skeleton at position 7 and 8 a saturated or unsaturated 5- or 6-membered cycle, wherein the hydrogen atoms of the alkylene or alkenylene substituent are optionally substituted at least by one halogen atom or linear or branched $C_1$ to $C_4$ alkyl or $C_2$ to $C_4$ alkenyl chain, wherein optionally one methylene group of the alkylene substituent forming the cycle is replaced by carbonyl group and the carbon atom at the adjoining position is optionally substituted by another methylene group, or one methylene group of the alkylene substituent forming the cycle is optionally replaced by oxygen or sulphur atom, while the sulphur atom is optionally functionalized by oxygen atom; or the hydrogens of one methylene group of the alkylene substituent are optionally replaced by —O—CH₂—, thereby forming oxirane ring,
  d) substituent —CH₂—O—CH(CH₃)— bound to the first carbon of an alkylene group —(CH₂)₃— which is formed by R⁴ and R⁵; and enantiomers of compounds of general formula I,
with the proviso that compounds wherein R¹ represents HO₂C—R⁶CR⁷—R⁸—, R⁶ is —(CH₂)₂—, R⁷ is oxygen atom bound by double bond and R⁸ is oxygen atom, while R² and R³ are methyl groups, R⁴ and R⁵ together form group-(CH₂)₃— forming with parent carbon atoms of tetradecahydrophenanthrene skeleton at position 7 and 8 a saturated five-membered ring; with absolute configuration 3R,5S,8S,9S,10S,13S,14S are excluded from formula I.

2. The amphiphilic compound of general formula I according to claim 1, selected from:

pyridinium (2R,4aS,4bS,8aR,10aR)-4a-methyltetradecahydrophenanthren-2-yl 2-sulfate (8),
pyridinium (2R,4aS,4bS,7S,8S,8aS,10aR)-7-(methoxymethyl)-4a,7,8-trimethyltetradecahydrophenanthren-2-yl 2-sulfate (18),
4-(((2R,4aS,4bS,7S,8aS,10aR)-7-(methoxymethyl)-4a,7,8-trimethyltetradecahydrophenanthren-2-yl)oxy)-4-oxobutanoic acid (19),
pyridinium (2R,4aS,7S,8S,10aR)-7-(methoxycarbonyl)-4a,7,8-trimethyltetradecahydrophenanthren-2-yl 2-sulfate (22),
4-(((2R,4aS,4bS,7R,8aS,10aR)-4a,7-dimethyltetradecahydrophenanthren-2-yl)oxy)-4-oxobutanoic acid (34),
pyridinium (2R,4aS,4bS,7R,8aS,10aR)-4a,7-dimethyltetradecahydrophenanthren-2-yl 2-sulfate (35),
methyl (2S,4aS,4bS,7R,8aR,10aS)-2,4b-dimethyl-7-(sulfooxy)tetradecahydrophenanthren-2-carboxylate (40),
pyridinium (3R,5R,8S,9S,10S,13S,14S)-10,13-dimethylhexadecahydro-1H-cyclopenta[a]phenanthren-3-yl 3-sulfate (49),
2-(((3R,5R,8S,9S,10S,13S,14S)-10,13-dimethylhexadecahydro-1H-cyclopenta[a]phenanthren-3-yl)oxy)-2-oxoethanoic acid (50),
2-(((3R,5R,8S,9S,10S,13S,14S)-10,13-dimethylhexadecahydro-1H-cyclopenta[a]phenanthren-3-yl)oxy)-2-oxopropanoic acid (51),
2-(((3R,5R,10S,13S,14S)-10,13-dimethylhexadecahydro-1H-cyclopenta[a]phenanthren-3-yl)amino)-2-oxoacetic acid (59),
((3R,5R,8S,9S,10S,13S,14S)-10,13-dimethylhexadecahydro-1H-cyclopenta[a]fenanthren-3-yl)amino)-3-oxopropanoic acid (61),
4-(((3R,5R,8S,9S,10S,13S,14S)-10,13-dimethylhexadecahydro-1H-cyclopenta[a]phenanthren-3-yl)oxy)-N,N,N-trimethyl-4-oxobutan-1-ammonium chloride (62),
4-(((3R,5R,8R,9S,10S,13R,14S)-10,13-dimethyl-2,3,4,5,6,7,8,9,10,11,12,13,14,15-tetradecahydro-1H-cyclopenta[a]phenanthren-3-yl)oxy)-4-oxobutanoic acid (64),
3-(((3R,5R,8R,9S,10S,13R,14S)-10,13-dimethyl-2,3,4,5,6,7,8,9,10,11,12,13,14,15-tetradecahydro-1H-cyclopenta[a]phenanthren-3-yl)oxy)-3-oxopropanoic acid (65),
3-(((3R,5R,8R,10S,13S,14S)-10,13-dimethyl-17-methylenehexadecahydro-1H-cyclopenta[a]phenanthren-3-yl)oxy)-3-oxopropanoic acid (67),
4-(((3R,5R,8R,9S,10S,13S,14S)-10,13-dimethyl-17-methylenehexadecahydro-1H-cyclopenta[a]phenanthren-3-yl)oxy)-4-oxobutanoic acid (68),
4-(((3R,5R,8R,9S,10S,13S,14S)-10,13-dimethyl-17-methylenehexadecahydro-1H-cyclopenta[a]phenanthren-3-yl)oxy)-4-oxopentanoic acid (69),
2-((3R,5R,8R,9S,10S,13S,14S)-10,13-dimethyl-17-oxohexadecahydro-1H-cyclopenta[a]phenanthren-3-yl) acetic acid (74),
2-(((3R,5R,8R,9S,10S,13S,14S)-10,13-dimethyl-17-methylenehexadecahydro-1H-cyclopenta[a]phenanthren-3-yl)oxy)-N,N,N-trimethyl-2-oxoethan-1-ammonium chloride (76),
3-(((3R,5R,8R,9S,10S,13S,14S,Z)-17-ethylidene-10,13-dimethylhexadecahydro-1H-cyclopenta[a]phenanthren-3-yl)oxy)-3-oxopropanoic acid (83),
5-(((3R,5R,8R,9S,10S,13S,14S,Z)-17-ethylidene-10,13-dimethylhexadecahydro-1H-cyclopenta[a]phenanthren-3-yl)oxy)-5-oxopentanoic acid (85), 3-(((3R,5R,8R,9S,10S,13S,14S,17R)-10,13-dimethyl-17-(prop-1-en-2-yl)hexadecahydro-1H-cyclopenta[a]phenanthren-3-yl)oxy)-3-oxopropanoic acid (88),
pyridinium (3R,5R,8R,9S,10S,13S,14S,17S)-17-iodo-10,13-dimethylhexadecahydro-1H-cyclopenta[a]phenanthren-3-yl 3-sulfate (93),
pyridinium (3R,5R,8R,9S,10S,13S,14S)-17,17-difluoro-10,13-dimethylhexadecahydro-1H-cyclopenta[a]phenanthren-3-yl 3-sulfate (95),
pyridinium (3R,5R,8R,9S,10S,13S,14S,17S)-10,13-dimethylhexadecahydrospiro[cyclopenta-[a]phenanthren-17,2'-oxirane]-3-yl 3-sulfate (97),
pyridinium (2R,4aS,4bS,6aS,10bS,6aS,12aR)-4a,6a-dimethyloctadecahydrochrysen-2-yl 2-sulfate (101), (4S)-4-amino-5-(((2R,4aS,4bS,6aS,10bS,12aR)-4a,6a-dimethyloctadecahydrochrysen-2-yl)oxy)-5-oxopentanoic acid (106),
pyridinium (3R,5R,8S,9S,10S,13R,14S)-10,13-dimethyl-16-methylenehexadecahydro-1H-cyclopenta[a]phenanthren-3-yl 3-sulfate (114),
pyridinium (3R,5R,8R,9S,10S,13S,14S)-10,13-dimethyl-17-methylenehexadecahydro-1H-cyclopenta[a]phenanthren-3-yl 3-sulfate (116),
pyridinium (3R,5R,8S,9S,10S,13R,14S,17S)-10,13,17-trimethylhexadecahydro-1H-cyclopenta[a]phenanthren-3-yl 3-sulfate (117),
pyridinium (3R,5R,8S,9S,10S,13R,14R,17R)-10,17-dimethylhexadecahydro-1H-cyclopenta[a]phenanthren-3-yl 3-sulfate (118),
pyridinium (3R,5R,8S,9S,10S,13R,14R,17S)-10,17-dimethylhexadecahydro-1H-cyclopenta[a]phenanthren-3-yl 3-sulfate (119),
pyridinium (3R,5R,8S,9S,10S,13R,14S,17S)-17-ethyl-10,13-dimethylhexadecahydro-1H-cyclopenta[a]phenanthren-3-yl 3-sulfate (120),
pyridinium (3R,5R,8R,9S,10S,13S,14S,17R)-10,13-dimethyl-17-(prop-1-en-2-yl)hexadecahydro-1H-cyclopenta[a]phenanthren-3-yl 3-sulfate (121),
pyridinium (3R,5R,8R,9S,10S,13R,14S,17R)-17-isopropyl-10,13-dimethylhexadecahydro-1H-cyclopenta[a]phenanthren-3-yl 3-sulfate (122),
pyridinium (3R,5R,8R,9S,10S,13R,14S,17R)-17-((R)-sec-butyl)-10,13-dimethylhexadecahydro-1H-cyclopenta[a]phenanthren-3-yl 3-sulfate (123),
pyridinium (3S,3aS,5bR,7aR,9R,11aS,11bS,13aR)-3,11a-dimethylhexadecahydro-1H,3H-naphtho[2',1':4,5]indeno[1,7a-c]furan-9-yl 9-sulfate (124),
pyridinium (3R,5R,8R,9R,10S,13S,14S)-13-methylhexadecahydro-1H-cyclopenta[a]phenanthren-3-yl 3-sulfate (126),
pyridinium (3R,5S,8R,9R,10S,13S,14S)-10,13-dimethylhexadecahydro-1H-cyclopenta[a]phenanthren-3-yl 3-sulfate (127),
pyridinium (2S,4aR,4bR,8aS,10aS)-4a-methyltetradecahydrophenanthren-2-yl 2-sulfate (128),
(4S)-4-amino-5-(((3R,5R,8S,9S,10S,13S,14S)-10,13-dimethylhexadecahydro-1H-cyclopenta[a]phenanthren-3-yl)oxy)-5-oxopentanoic acid (130),
1-((3R,5R,8S,9S,10S,13S,14S)-10,13-Dimethylhexadecahydro-1H-cyclopenta[a]phenanthren-3-yl)-5-oxopyrrolidine-3-carboxylic acid (131), mixture of isomers
sodium 2-oxo-2-(((3R,5R,8S,9S,10S,13R,14S,17S)-10,13,17-trimethylhexadecahydro-1H-cyclopenta[a]phenanthren-3-yl)amino)acetate (138),
3-oxo-3-(((3R,5R,8S,9S,10S,13R,14S,17S)-10,13,17-trimethylhexadecahydro-1H-cyclopenta[a]phenanthren-3-yl)amino)propanoic acid (140),
sodium 2-(((3R,5R,8R,9S,10S,13R,14S)-17-((R)-sec-butyl)-10,13-dimethylhexadecahydro-1H-cyclopenta[a]phenanthren-3-yl)amino)-2-oxoacetate (148),
3-(((3R,5R,8R,9S,10S,13R,14S)-17-((R)-sec-butyl)-10,13-dimethylhexadecahydro-1H-cyclopenta[a]phenanthren-3-yl)amino)-3-oxopropanoic acid (149),
2-(((3R,5R,8R,9S,10S,13S,14S,Z)-17-ethylidene-10,13-dimethylhexadecahydro-1H-cyclopenta[a]phenanthren-3-yl)amino)-2-oxoacetic acid (154),
3-(((3R,5R,8R,9S,10S,13S,14S,Z)-17-ethylidene-10,13-dimethylhexadecahydro-1H-cyclopenta[a]phenanthren-3-yl)amino)-3-oxopropanoic acid (155).

3. The amphiphilic compound of general formula I according to claim 1, wherein the compound is 3-oxo-3-(((3R,5R,8S,9S,10S,13R,14S,17S)-10,13,17-trimethylhexadecahydro-1H-cyclopenta[a]phenanthren-3-yl)amino)propanoic acid (140).

4. The amphiphilic compound of general formula I according to claim 1, wherein $R^6$ represents straight or branched $C_1$ to $C_6$ alkylene or $C_2$ to $C_6$ alkenylene chain, unsubstituted or substituted with one or more halogen atoms or amino group or amino group protected by tert-butylcarbonyl.

5. The amphiphilic compound of general formula I according to claim 1, wherein $R^8$ represents an at least divalent atom selected from the group consisting of nitrogen, oxygen and carbon.

6. A method of treatment of at least one disorder, the disorder being selected from imbalance in glutamatergic neurotransmitter system, ischemic damage of CNS, neurodegenerative changes and disorders of CNS, affective disorders, depression, post-traumatic stress disorder, diseases related to stress, anxiety, schizophrenia and psychotic disorders, pain, addiction, multiple sclerosis, epilepsy, and glioma;
the method comprising administering a compound according to claim 1 to a subject in need thereof.

* * * * *

UNITED STATES PATENT AND TRADEMARK OFFICE
CERTIFICATE OF CORRECTION

PATENT NO. : 10,017,535 B2
APPLICATION NO. : 15/506318
DATED : July 10, 2018
INVENTOR(S) : Eva Kudova et al.

It is certified that error appears in the above-identified patent and that said Letters Patent is hereby corrected as shown below:

In the Claims

Column 77, Lines 66-67, in Claim 2, delete "of general formula I according to claim 1".

Column 80, Lines 28-29, in Claim 3, delete "of general formula I according to claim 1" and insert --according to claim 2-- therefor.

Signed and Sealed this
Nineteenth Day of November, 2019

Andrei Iancu
*Director of the United States Patent and Trademark Office*